US012233059B2

(12) United States Patent
Etkin et al.

(10) Patent No.: US 12,233,059 B2
(45) Date of Patent: *Feb. 25, 2025

(54) EFFECTIVE TREATMENT OF DEPRESSION IN PATIENTS HAVING IMPAIRED LEARNING AND/OR MEMORY OR CERTAIN EEG CHARACTERISTICS WITH A BENZYLPIPERAZINE-AMINOPYRIDINE AGENT

(71) Applicant: Alto Neuroscience, Inc., Los Altos, CA (US)

(72) Inventors: Amit Etkin, Los Altos, CA (US); Wei Wu, Los Altos, CA (US); Chao Wang, Los Altos, CA (US); Nicholas Cooper, Los Altos, CA (US); Joshua Jordan, Los Altos, CA (US); Adam Savitz, Los Altos, CA (US)

(73) Assignee: Alto Neuroscience, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/670,637

(22) Filed: May 21, 2024

(65) Prior Publication Data

US 2024/0307380 A1   Sep. 19, 2024

Related U.S. Application Data

(63) Continuation-in-part of application No. 18/528,486, filed on Dec. 4, 2023.

(60) Provisional application No. 63/579,547, filed on Aug. 30, 2023, provisional application No. 63/386,137, filed on Dec. 5, 2022.

(51) Int. Cl.
| | |
|---|---|
| A61K 31/496 | (2006.01) |
| A61K 9/00 | (2006.01) |
| A61K 31/19 | (2006.01) |
| A61K 31/53 | (2006.01) |
| A61K 33/00 | (2006.01) |
| A61P 25/24 | (2006.01) |
| A61B 5/16 | (2006.01) |
| A61B 5/374 | (2021.01) |

(52) U.S. Cl.
CPC .......... *A61K 31/496* (2013.01); *A61K 9/0053* (2013.01); *A61K 31/19* (2013.01); *A61K 31/53* (2013.01); *A61K 33/00* (2013.01); *A61P 25/24* (2018.01); *A61B 5/165* (2013.01); *A61B 5/374* (2021.01)

(58) Field of Classification Search
CPC .................................................. A61K 31/496
See application file for complete search history.

(56) References Cited

U.S. PATENT DOCUMENTS

| | | | |
|---|---|---|---|
| 7,560,553 B1 | 7/2009 | Kelleher-Andersson et al. | |
| 7,858,628 B2 | 12/2010 | Kelleher-Andersson et al. | |
| 9,278,933 B2 | 3/2016 | Venkatraman et al. | |
| 9,399,039 B1 | 7/2016 | Sabbagh et al. | |
| 9,572,807 B2 * | 2/2017 | Johe ..................... | A61K 31/444 |
| 10,413,534 B2 | 9/2019 | Johe | |
| 2006/0105394 A1 | 5/2006 | Pomara | |
| 2015/0359792 A1 | 12/2015 | Johe | |
| 2019/0142829 A1 | 5/2019 | Johe | |
| 2022/0387424 A1 | 12/2022 | Etkin et al. | |

FOREIGN PATENT DOCUMENTS

| | | |
|---|---|---|
| WO | 2018048927 A1 | 3/2018 |
| WO | 2019222629 A1 | 11/2019 |

OTHER PUBLICATIONS

International Search Report and Written Opinion issued in PCT/US2023/082341 on Mar. 13, 2024.
"Multiple-Dose Pharmacokinetics (PK), and Pharmacodynamic (PD) Effect of NSI-189 Phosphate in Depression Patient Subjects,", ClinicalTrials.gov, Dec. 18, 2013 (Dec. 18, 2013), pp. 1-3, XP055246032, Retrieved from the Internet: URL: https://web.archive.org/web/20131218064538/http:/clinicaltrials.gov/ct2/show/record/NCT01520649 [retrieved on Jan. 29, 2016] the whole document.
English , et al., "Abstract P-32-003, Abstracts from the 29th CINP World Congress of Neuropsychopharmacology,", Vancouver, Canada, Jun. 26, 2024, Int'l J. Neuropsychopharmacology, vol. 17, No. Suppl. 1, Jun. 1, 2014, XP055592721, Cambridge ISSN: 1461-1457, DOI: 10.1017/SI461145714000741, p. 119.
Jolival, T Corinne G, et al., "Effects of the Neurogenic Molecule NSI-189 on Indices of Cognition in an App/Tau Mouse Model of Alzheimer's Disease, Alzheimer's & Dementia,", Elsevier, New York, NY, US, vol. 15, No. 7, Jul. 1, 2019 (Jul. 1, 2019), XP085868734, ISSN: 1552-5260, DOI: 10.1016/J.JALZ.2019.06.2474 [retrieved on Oct. 18, 2019] paragraph p. 2-067.
Liu, Yan , et al., "Enhancement of synaptic plasticity and reversal of impairments in motor and cognitive functions in a mouse model of Angelman Syndrome by a small neurogenic molecule,", NSI-189, Neuropharmacology, vol. 144, Nov. 5, 2018 (Nov. 5, 2018), pp. 337-344, XP055901515, Amsterdam, NL ISSN: 0028-3908, DOI:10.1016/j.neuropharm.2018.10.038 results, discussion.

(Continued)

*Primary Examiner* — Rei Tsang Shiao
(74) *Attorney, Agent, or Firm* — Blank Rome LLP

(57) ABSTRACT

This invention relates to the use of (4-benzylpiperazin-1-yl)-[2-(3-methylbutylamino)pyridin-3-yl]methanone (NSI-189) or a pharmaceutically acceptable salt thereof in the treatment of a psychiatric condition in which depressive symptoms are prominent, including major depressive disorder (MDD), bipolar disorder, post-traumatic stress disorder, substance use disorder, and depression-related aspects of schizophrenia (e.g. negative symptoms) in select patients who exhibit impaired learning and/or memory. The invention also relates to the use of NSI-189 or a pharmaceutically acceptable salt thereof in the treatment of a psychiatric condition in which depressive symptoms are prominent, including major depressive disorder (MDD), in select patients who exhibit impaired learning and/or memory or certain EEG characteristics.

20 Claims, 13 Drawing Sheets

(56) References Cited

OTHER PUBLICATIONS

McIntyre, Rogers, et al., "The neurogenic compound, NSI-189 phosphate: a novel multi-domain treatment capable of pro-cognitive and antidepressant effects", Expert Opinion on Investigational Drugs, vol. 26, No. 6, May 8, 2017 (May 8, 2017), pp. 767-770, XP055421667, UK ISSN: 1354-3784, DOI: 10.1080/13543784.2017.1324847 the whole document.

Papakostas, GI, et al., "A phase 2, double-blind, placebo-controlled study of NSI-189 phosphate, a neurogenic compound, among outpatients with major depressive disorder", Molecular Psychiatry, Nature Publishing Group UK, London, vol. 25, No. 7, Jan. 9, 2019 (Jan. 9, 2019), pp. 1569-1579, XP037173336, ISSN: 1359-4184, DOI: 10.1038/S41380-018-0334-8 [retrieved on Jan. 9, 2019] cited in the application the whole document.

Alto Neuroscience press release, "Alto Neuroscience Reports Topline Results from a Phase 2b Trial Evaluating ALTO-100 as a Treatment for Major Depressive Disorder", Oct. 22, 2024.

"Anxiety in Angelman Syndrome", Anxiety in Angelman Syndrome I Angel man Syndrome News Angelman Syndrome (last updated Sep. 22, 2019). (Year: 2019).

Fava, M, et al., "A Phase 1 B, randomized, double blind, placebo controlled, multiple-dose escalation study of NSI-189 phosphate, a neurogenic compound, in depressed patients", Molecular Psychiatry (2016) 21, 1372-1380. (Year: 2016).

Hanzlik, Emily, et al., "Mirtazapine for sleep disturbances in Angelman syndrome: a retrospective chart review of 8 pediatric cases", J Clin Sleep Med. Apr. 1, 20205; 16(4):591-595. (Year: 2020).

\* cited by examiner

| Test | good verbal memory | | poor verbal memory | | p-value |
| --- | --- | --- | --- | --- | --- |
| | mean | SEM | mean | SEM | |
| Verbal fluency (animals cue) | -0.26 | 0.10 | -0.86 | 0.14 | 0.0007 |
| Verbal fluency (letters cue) | -0.18 | 0.11 | -0.71 | 0.12 | 0.002 |
| Corsi block span | -0.14 | 0.14 | -1.06 | 0.17 | 0.0001 |
| DSST correct rate | 0.08 | 0.11 | -0.79 | 0.14 | 0.000004 |
| Flanker congruent RT | -0.49 | 0.12 | -0.89 | 0.17 | 0.05 |
| Flanker incongruent RT | -0.50 | 0.11 | -0.97 | 0.19 | 0.024 |
| Choice RT | -0.30 | 0.13 | -0.84 | 0.18 | 0.02 |
| Simple RT | 0.65 | 0.15 | -0.09 | 0.23 | 0.007 |
| Trails A time | -0.23 | 0.10 | -0.91 | 0.14 | 0.0001 |
| Trails B time | -0.14 | 0.12 | -1.00 | 0.14 | 0.00002 |
| Accuracy FERT | -0.08 | 0.15 | -0.79 | 0.19 | 0.004 |
| Anger accuracy FERT | -0.03 | 0.14 | -0.66 | 0.18 | 0.006 |
| Fear accuracy FERT | -0.25 | 0.15 | -0.74 | 0.18 | 0.041 |
| Happy accuracy FERT | 0.27 | 0.14 | -0.22 | 0.21 | 0.048 |

Figure 7

EFFECTIVE TREATMENT OF DEPRESSION IN PATIENTS HAVING IMPAIRED LEARNING AND/OR MEMORY OR CERTAIN EEG CHARACTERISTICS WITH A BENZYLPIPERAZINE-AMINOPYRIDINE AGENT

This application is a continuation-in-part of U.S. patent application Ser. No. 18/528,486, filed Dec. 4, 2023, claims the benefit of U.S. Provisional Application No. 63/386,137, filed Dec. 5, 2022, and U.S. Provisional Application No. 63/579,547, filed Aug. 30, 2023, each of which is hereby incorporated by reference.

FIELD OF THE INVENTION

This invention relates to the use of (4-benzylpiperazin-1-yl)-[2-(3-methylbutylamino)pyridin-3-yl]methanone (NSI-189) or a pharmaceutically acceptable salt thereof in the treatment of a psychiatric condition in which depressive symptoms are prominent (such as, e.g., major depressive disorder (MDD) and/or post-traumatic stress disorder (PTSD)) in select patients who, for instance, exhibit impaired learning and/or memory.

BACKGROUND OF THE INVENTION

Clinical care for depression involves assessment and diagnosis based on a set of clinician-assessed and patient-reported symptoms such as depressed mood, anhedonia, diminished ability to think or concentrate, appetite changes, sleep and psychomotor changes but notably not based on biological or quantitative behavioral variables. When an assessment such as a magnetic resonance imaging (MRI) scan or a blood test is performed, it is to rule out non-psychiatric causes of depression which may necessitate treatments other than an antidepressant medication, including causes such as a tumor, hypothyroidism, dementia or metabolic disruptions. After diagnosing a patient with depression such as in major depressive disorder (MDD), a clinician may then prescribe one of multiple antidepressant treatments, which primarily includes drugs such as selective serotonin reuptake inhibitors (SSRIs), serotonin norepinephrine reuptake inhibitors (SNRIs), and norepinephrine dopamine reuptake inhibitors (NDRIs), or atypical antidepressants.

Notably, selection of antidepressant medication is done by trial-and-error, with no symptom profile or biological or quantitative behavioral measures to inform medication choice. Typically, SSRIs are selected as the first line treatment based on their generally better tolerability, but not because they are known to be more effective generally, nor more effective for a particular patient. Most patients, however, fail to respond adequately to the first medication, at which point selection of the next medication again follows a trial-and-error process. The next medication may be a switch (stopping one antidepressant and starting another) or adjunctive treatment (a new medication is added to the ongoing antidepressant). It has been found that on average, failing one SSRI does not necessarily predict a different response to another SSRI versus an SNRI or NDRI (29). As such, typical clinical assessments do not provide information useful for selection of subsequent medication trials, and therefore external information not available to the clinician is required for improving medication selection.

A similar situation exists for bipolar depression (including both bipolar I and bipolar II disorders). The only approved medications are atypical antipsychotic drugs, which have limited efficacy, a high rate of discontinuation due to intolerability, operate via the same mechanisms, and are selected between based on trial-and-error (41). Conventional antidepressant medications are ineffective and not approved by the US FDA for the treatment of bipolar depression, and carry concerns about increasing susceptibility for induction of mania.

The economic, societal and personal cost of depression is very large, with depression being the leading cause of disability worldwide. This is even more pronounced for treatment-resistant depression (28) thus suggesting that finding the best medication for an individual early in the course of treatment would provide many downstream benefits to the patient and society at large.

Similar clinical needs exist in other related conditions in which depressive symptoms exist. Such symptoms include low mood, lack of experience of pleasure (anhedonia), impairments in motivation, and impairments in attention, cognition or decision making. These conditions include major depressive disorder, bipolar depression (such as bipolar I or bipolar II disorders), post-traumatic stress disorder, substance use disorder and depression-related aspects of schizophrenia (e.g., negative symptoms). Importantly, these different depression-related symptoms or areas of dysfunction co-occur and may be functionally related. For example, a patient with major depression may report depressed mood and lack of motivation. Likewise, the same symptoms may be reported by patients diagnosed with other conditions in which similar impairments may co-occur, such as bipolar depression, post-traumatic stress disorder or substance use disorder. Though schizophrenia is often thought of with respect to prominent hallucinations and delusions, the depression-like negative symptoms are often the greater source of long-term disability and functional impairment. Hence, a treatment approach that encompasses these multiple and related functional systems would be both of importance to any one of these clinical conditions, and equally may be applicable across them.

It has been proposed that depression and depressive symptoms (e.g. in PTSD) arise at least in part from impairments in neuronal proliferation in the adult brain, neuronal growth and differentiation, elaboration of neuronal substructures important in neural communication, and impairments in neural plasticity (1-7). Moreover, it has been theorized that medications that reverse one or multiple of these dysfunctions would be effective antidepressants (1-7). It has been demonstrated, for example, that medications that have been clinically proven to be effective antidepressants in humans with depression also induce the growth and differentiation of neurons in the brains of adult animals (1, 3, 4).

Prior work has found that certain benzylpiperazine-aminopyridines or open chain forms thereof can induce proliferation and maturation of neurons in the adult brains of animals (8,9). One such benzylpiperazine-aminopyridine, NSI-189, was discovered by screening a chemical library against an in vitro model for hippocampal neurogenesis. Unlike most recently United States Food and Drug Administration (FDA) approved antidepressants (such as SSRIs), the precise mechanism of action of NSI-189 is not understood. There are no members of its class that have received FDA approval. An initial small-scale Phase 1b clinical study in patients with major depression found promising evidence for potential antidepressant efficacy of NSI-189 dosed at total daily doses of 40 mg, 80 mg or 120 mg (10). However, this study was conducted on a small sample of patients and had as its goal to establish safety and tolerability, and thus did not yield definitive efficacy data, with only 18 patients across all active dose condition (and 6 on placebo).

A subsequent Phase 2 study was then performed on 220 patients with major depression (11). In that study, patients were randomized to receive a total daily dose of 40 mg or 80 mg of NSI-189 or placebo in stage 1 of the clinical trial design. Patients receiving placebo and who failed to respond to placebo were then re-randomized to 40 mg, 80 mg or placebo in stage 2 of the trial. Treatment in either stage was given for six weeks. This design is termed a Sequential Parallel Clinical Design (SPCD) and is analyzed statistically by combining results in a pre-defined manner for outcomes differences between relevant groups (e.g., drug vs. placebo) in each of the stages individually. There are two depression outcome measures accepted by the FDA for the evaluation of adults. See the June 2018 FDA draft guidance entitled "Major Depressive Disorder: Developing Drugs for Treatment." These are the Montgomery-Asberg Depression Rating Scale (MADRS), which was the primary outcome in this study, as well as the Hamilton Depression Rating Scale (HDRS) which was a key secondary outcome measure. However, despite the promise of animal work and early human studies, results from this 220-patient study failed to demonstrate any evidence of antidepressant efficacy on the MADRS primary outcome measure or the HDRS key secondary measure (11) across either the full SPCD analysis or analyses of each stage alone. The 80 mg daily dose did not demonstrate efficacy on any study measure (11). It was reported that any benefits of NSI-189 on depression and cognition are independent effects (27).

While nominally significant effects were observed for the 40 mg dose compared to placebo (but not the 80 mg dose) on several secondary measures, these results were not corrected for multiple comparisons (nor would have survived correction) and do not reflect measures acceptable to the US FDA in support of antidepressant efficacy for a medication. Thus, NSI-189 was not found to be an effective antidepressant. Moreover, inasmuch as uncorrected results on secondary measures can even be used to draw positive conclusions regarding efficacy of the compound, these point to potential efficacy for 40 mg and not 80 mg. This would be surprising as it would reflect an inverted dose-response curve, while the typical expectation is that a higher dose would be more effective than a lower dose. Together, these results led to discontinuance of the development of NSI-189.

There is a continuing need for improved treatments for depression, such as antidepressants which have a different mechanism of action than those currently used for treatment.

SUMMARY OF THE INVENTION

The inventors discovered that (4-benzylpiperazin-1-yl)-[2-(3-methylbutylamino)pyridin-3-yl]methanone (NSI-189) (such as 80 mg NSI-189) is effective in treating depression (e.g., improving depressive symptoms) in patients (i) having objectively determined impaired learning and/or memory (e.g., impaired verbal memory, for instance as determined by VM-REACT (Verbal Memory REcAll Computerized Test)), (ii) exhibiting an electroencephalogram (EEG) with (A) a low aperiodic exponent, (B) a high power in the low gamma range (e.g., 31-50 Hz, 31-60 Hz, or 35-45 Hz), (C) a low power in the alpha frequency (8-12 Hz), or (D) any combination of any of (A), (B), and (C), or (iii) both (i) and (ii). This is surprising since NSI-189 was previously reported to be ineffective in treating major depressive disorder, and that the 80 mg dose did not demonstrate efficacy on any study measure for the entire study population (including all secondary measures).

One embodiment of the invention is a method of treating major depressive disorder or one or more symptoms thereof in a human patient having objectively determined impaired learning and/or memory (e.g., impaired verbal memory) by orally administering to the patient from about 40 to about 240 mg of NSI-189 or a pharmaceutically acceptable salt thereof daily. In one embodiment, the patient exhibits an electroencephalogram (EEG) with (i) a low aperiodic exponent, (ii) a high power in the low gamma range, (iii) a low power in the alpha frequency, or (iv) any combination of any of (i), (ii), and (iii).

Another embodiment is a method of treating major depressive disorder or one or more symptoms thereof in a human patient exhibiting an electroencephalogram (EEG) with (i) a low aperiodic exponent, (ii) a high power in the low gamma range (31-50 Hz), (iii) a low power in the alpha frequency, or (iv) any combination of any of the foregoing. The method comprises orally administering to the patient from about 40 to about 240 mg of NSI-189 or a pharmaceutically acceptable salt thereof daily. In one embodiment, about 60 to about 100 mg of NSI-189 or a pharmaceutically acceptable salt thereof is administered daily. In one preferred embodiment, about 80 mg of NSI-189 or a pharmaceutically acceptable salt thereof is administered daily.

Yet another embodiment is a method of treating bipolar depression or one or more symptoms thereof in a human patient having objectively determined impaired learning and/or memory (e.g., impaired verbal memory) by orally administering to the patient from about 40 to about 240 mg of NSI-189 or a pharmaceutically acceptable salt thereof daily. In one embodiment, the patient exhibits an electroencephalogram (EEG) with (i) a low aperiodic exponent, (ii) a high power in the low gamma range, (iii) a low power in the alpha frequency, or (iv) any combination of any of (i), (ii), and (iii).

Yet another embodiment is a method of treating a major depressive episode in a human patient having bipolar disorder with depression and objectively determined impaired learning and/or memory (e.g., impaired verbal memory) by orally administering to the patient from about 40 to about 240 mg of NSI-189 or a pharmaceutically acceptable salt thereof daily. In one preferred embodiment, about 40 mg of (4-benzylpiperazin-1-yl)-[2-(3-methylbutylamino)pyridin-3-yl]methanone or a pharmaceutically acceptable salt thereof is administered twice daily. In one embodiment, the patient is concurrently treated with a mood stabilizer in addition to (4-benzylpiperazin-1-yl)-[2-(3-methylbutylamino)pyridin-3-yl]methanone or a pharmaceutically acceptable salt thereof. In one embodiment, the mood stabilizer is selected from lithium, lamotrigine, valproic acid, and any combination of any of the foregoing. In another embodiment, the mood stabilizer is selected from lithium, lamotrigine, or valproic acid. In yet another embodiment, the bipolar disorder is bipolar I disorder. In yet another embodiment, the bipolar disorder is bipolar II disorder.

Another embodiment is a method of treating bipolar depression or one or more symptoms thereof in a human patient exhibiting an electroencephalogram (EEG) with (i) a low aperiodic exponent, (ii) a high power in the low gamma range (31-50 Hz), (iii) a low power in the alpha frequency, or (iv) any combination of any of the foregoing. The method comprises orally administering to the patient from about 40 to about 240 mg of NSI-189 or a pharmaceutically acceptable salt thereof daily. In one embodiment, about 60 to about 100 mg of NSI-189 or a pharmaceutically acceptable salt thereof is administered daily. In one preferred embodiment, about 80 mg of NSI-189 or a pharmaceutically acceptable salt thereof is administered daily.

Yet another embodiment is a method for selecting a treatment for major depressive disorder, post-traumatic stress disorder, both major depressive disorder and post-traumatic stress disorder, a major depressive episode, bipolar depression, or one or more symptoms thereof in a human patient and treating the patient. The method comprises:
  (a) objectively assessing whether the patient has impaired learning and/or memory (e.g., impaired verbal memory) for the purpose of selecting a treatment for the patient; and
  (b) upon an assessment from step (a) that the patient has impaired learning and/or memory, initiating oral administration to the patient of from about 40 to about 240 mg of NSI-189 or a pharmaceutically acceptable salt thereof daily. In one embodiment, the method further comprises the step (c) of, upon an assessment from step (a) that the patient does not have impaired learning and/or memory, not initiating oral administration to the patient of from about 40 to about 240 mg of NSI-189 or a pharmaceutically acceptable salt thereof daily.

Yet another embodiment is a method for treating a major depressive episode in a human patient with bipolar disorder with depression, where the method comprises:
  (a) objectively assessing whether the patient has impaired learning and/or memory (e.g., impaired verbal memory); and
  (b) upon an assessment from step (a) that the patient has impaired learning and/or memory, initiating oral administration to the patient of from about 40 to about 240 mg of NSI-189 or a pharmaceutically acceptable salt thereof daily. In one embodiment, the method further comprises the step (c) of, upon an assessment from step (a) that the patient does not have impaired learning and/or memory, not initiating oral administration to the patient of from about 40 to about 240 mg of NSI-189 or a pharmaceutically acceptable salt thereof daily. In one embodiment, the patient prior to initiation of treatment with NSI-189 or a pharmaceutically acceptable salt thereof was being treated with a mood stabilizer, and step (b) comprises upon an assessment from step (a) that the patient has impaired learning and/or memory, (i) initiating oral administration to the patient of from about 40 to about 240 mg of NSI-189 or a pharmaceutically acceptable salt thereof daily, and (ii) continuing administration of the mood stabilizer. In one preferred embodiment, about 40 mg of (4-benzylpiperazin-1-yl)-[2-(3-methylbutylamino)pyridin-3-yl]methanone or a pharmaceutically acceptable salt thereof is administered twice daily. In one embodiment, the mood stabilizer is selected from lithium, lamotrigine, valproic acid, and any combination of any of the foregoing. In another embodiment, the mood stabilizer is selected from lithium, lamotrigine, or valproic acid. In yet another embodiment, the bipolar disorder is bipolar I disorder. In yet another embodiment, the bipolar disorder is bipolar II disorder.

Yet another embodiment is a method for selecting a treatment for major depressive disorder, post-traumatic stress disorder, both major depressive disorder and post-traumatic stress disorder, a major depressive episode, bipolar depression, or one or more symptoms thereof in a human patient and treating the patient comprising:
  (a) diagnosing a patient as suffering from major depressive disorder, post-traumatic stress disorder, both major depressive disorder and post-traumatic stress disorder, a major depressive episode, or bipolar depression;
  (b) objectively assessing whether the patient has impaired learning and/or memory (e.g., impaired verbal memory, for instance as determined by VM-REACT) for the purpose of selecting a treatment for the patient;
  (c) selectively prescribing NSI-189 or a pharmaceutically acceptable salt thereof to the patient in view of the diagnosis of the patient and an objective assessment that the patient has impaired learning and/or memory; and
  (d) upon selectively prescribing NSI-189 or a pharmaceutically acceptable salt thereof, initiating oral administration to the patient of from about 40 to about 240 mg of NSI-189 or a pharmaceutically acceptable salt thereof daily.

Yet another embodiment is a method for determining whether a patient suffering from major depressive disorder, post-traumatic stress disorder, both major depressive disorder and post-traumatic stress disorder, a major depressive episode, or bipolar depression can effectively be treated with NSI-189 and treating a human patient receptive to such treatment. The method comprises:
  (a) objectively determining whether the patient has impaired learning and/or memory (e.g., impaired verbal memory); and
  (b) upon a determination from step (a) that the patient has impaired learning and/or memory, initiating oral administration to the patient of from about 40 to about 240 mg of NSI-189 or a pharmaceutically acceptable salt thereof daily. In one embodiment, the method further comprises the step (c) of, upon a determination from step (a) that the patient does not have impaired learning and/or memory, not initiating oral administration to the patient of from about 40 to about 240 mg of NSI-189 or a pharmaceutically acceptable salt thereof daily.

Yet another embodiment is a method of treating major depressive disorder, post-traumatic stress disorder, both major depressive disorder and post-traumatic stress disorder, a major depressive episode, bipolar depression, or one or more symptoms thereof in a human patient comprising the steps of:
  (a) prescribing to the patient from about 40 to about 240 mg of NSI-189 or a pharmaceutically acceptable salt thereof daily, the prescribing being performed in response to (i) marketing of the NSI-189 or a pharmaceutically acceptable salt thereof as providing effective treatment of major depressive disorder, post-traumatic stress disorder, both major depressive disorder and post-traumatic stress disorder, a major depressive episode, bipolar depression, or one or more symptoms thereof in patients having objectively determined impaired learning and/or memory and (ii) an objective determination that the patient has impaired learning and/or memory (e.g., impaired verbal memory); and
  (b) orally administering the prescribed NSI-189 or a pharmaceutically acceptable salt thereof to the patient.

Yet another embodiment is a method of treating major depressive disorder, post-traumatic stress disorder, both major depressive disorder and post-traumatic stress disorder, a major depressive episode, bipolar depression, or one or more symptoms thereof in a human patient comprising the steps of:

(a) diagnosing a patient as suffering from major depressive disorder, post-traumatic stress disorder, both major depressive disorder and post-traumatic stress disorder, a major depressive episode, bipolar depression, or one or more symptoms thereof;
(b) prescribing to the patient from about 40 to about 240 mg of NSI-189 or a pharmaceutically acceptable salt thereof daily, the prescribing being performed in response to (i) marketing of the NSI-189 or a pharmaceutically acceptable salt thereof as providing effective treatment of major depressive disorder, post-traumatic stress disorder, both major depressive disorder and post-traumatic stress disorder, a major depressive episode, bipolar depression, or one or more symptoms thereof in patients having objectively determined impaired learning and/or memory (e.g., impaired verbal memory) and (ii) an objective determination that the patient has impaired learning and/or memory; and
(c) orally administering the prescribed NSI-189 or a pharmaceutically acceptable salt thereof to the patient.

Yet another embodiment is a method of treating major depressive disorder, post-traumatic stress disorder, both major depressive disorder and post-traumatic stress disorder, a major depressive episode, bipolar depression, or one or more symptoms thereof in a human patient comprising the steps of:
(a) analyzing one or more indicators of the responsiveness of the patient to NSI-189 or a pharmaceutically acceptable salt thereof as a treatment, wherein the one or more indicators include objectively determined impaired learning and/or memory; and
(b) where the patient is determined to be response to NSI-189 or a pharmaceutically acceptable salt thereof based on the one or more indicators, orally administering to the patient an effective amount of NSI-189 or a pharmaceutically acceptable salt thereof.

Yet another embodiment is a method for selecting a treatment for major depressive disorder or one or more symptoms thereof in a human patient and treating the patient comprising:
(a) assessing, for the purpose of selecting a treatment for the patient, whether the patient (i) has objectively determined impaired learning and/or memory (e.g., impaired verbal memory), (ii) exhibits an electroencephalogram (EEG) with (A) a low aperiodic exponent, (B) a high power in the low gamma range (31-50 Hz), (C) a low power in the alpha frequency, or (D) any combination of any of (A), (B), and (C), or (iii) both (i) and (ii); and
(b) upon an assessment from step (a) that the patient meets (i), (ii), or (iii), initiating oral administration to the patient of from about 40 to about 240 mg of NSI-189 or a pharmaceutically acceptable salt thereof daily. In one embodiment, the method further comprises the step (c) upon an assessment from step (a) that the patient does not meet (i) or (ii), not initiating oral administration to the patient of from about 40 to about 240 mg of NSI-189 or a pharmaceutically acceptable salt thereof daily.

Yet another embodiment is a method for selecting a treatment for major depressive disorder or one or more symptoms thereof in a human patient and treating the patient comprising:
(a) diagnosing a patient as suffering from major depressive disorder;
(b) assessing, for the purpose of selecting a treatment for the patient, whether the patient (i) has objectively determined impaired learning and/or memory (e.g., impaired verbal memory), (ii) exhibits an electroencephalogram (EEG) with (A) a low aperiodic exponent, (B) a high power in the low gamma range (31-50 Hz), (C) a low power in the alpha frequency, or (D) any combination of any of (A), (B), and (C), or (iii) both (i) and (ii);
(c) selectively prescribing NSI-189 or a pharmaceutically acceptable salt thereof to the patient in view of the diagnosis of the patient and an assessment that the patient meets (i), (ii), or (iii); and
(d) upon selectively prescribing NSI-189 or a pharmaceutically acceptable salt thereof, initiating oral administration to the patient of from about 40 to about 240 mg of NSI-189 or a pharmaceutically acceptable salt thereof daily.

Yet another embodiment is a method for determining whether a patient suffering from major depressive disorder can effectively be treated with NSI-189 and treating a human patient receptive to such treatment. The method comprises:
(a) assessing, for the purpose of selecting a treatment for the patient, whether the patient (i) has objectively determined impaired learning and/or memory (e.g., impaired verbal memory), (ii) exhibits an electroencephalogram (EEG) with (A) a low aperiodic exponent, (B) a high power in the low gamma range (31-50 Hz), (C) a low power in the alpha frequency, or (D) any combination of any of (A), (B), and (C), or (iii) both (i) and (ii); and
(b) upon a determination from step (a) that the patient meets (i), (ii), or (iii), initiating oral administration to the patient of from about 40 to about 240 mg of NSI-189 or a pharmaceutically acceptable salt thereof daily. In one embodiment, the method further comprises the step (c) upon a determination from step (a) that the patient does not meet (i), (ii), or (iii), not initiating oral administration to the patient of from about 40 to about 240 mg of NSI-189 or a pharmaceutically acceptable salt thereof daily.

Yet another embodiment is a method of treating major depressive disorder or one or more symptoms thereof in a human patient comprising the steps of:
(a) prescribing to the patient from about 40 to about 240 mg of NSI-189 or a pharmaceutically acceptable salt thereof daily, the prescribing being performed in response to (I) marketing of the NSI-189 or a pharmaceutically acceptable salt thereof as providing effective treatment of major depressive disorder or a symptom thereof in patients (i) having objectively determined impaired learning and/or memory (e.g., impaired verbal memory), (ii) that exhibit an electroencephalogram (EEG) with (A) a low aperiodic exponent, (B) a high power in the low gamma range (31-50 Hz), (C) a low power in the alpha frequency, or (D) any combination of any of (A), (B), and (C), or (iii) both (i) and (ii), and (II) a determination that the patient meets (i), (ii) or (iii); and
(b) orally administering the prescribed NSI-189 or a pharmaceutically acceptable salt thereof to the patient.

Yet another embodiment is a method of treating major depressive disorder or one or more symptoms thereof in a human patient comprising the steps of:
(a) diagnosing a patient as suffering from major depressive disorder;
(b) prescribing to the patient from about 40 to about 240 mg of NSI-189 or a pharmaceutically acceptable salt thereof daily, the prescribing being performed in response to (I) marketing of the NSI-189 or a pharmaceutically acceptable salt thereof as providing effective treatment of major depressive disorder or a symptom thereof in patients (i) having objectively determined impaired learning and/or memory (e.g., impaired verbal memory), (ii) that exhibit an electroencephalogram (EEG) with (A) a low aperiodic exponent, (B) a high power in the low gamma range (31-50 Hz), (C) a low power in the alpha frequency, or (D) any combination of any of (A), (B), and (C), or (iii) both (i) and (ii), and (II) a determination that the patient meets (i), (ii) or (iii); and (c) orally administering the prescribed (4-benzylpiperazin-1-yl)-[2-(3-methylbutylamino)pyridin-3-yl]methanone or a pharmaceutically acceptable salt thereof to the patient.

Yet another embodiment is a method of treating major depressive disorder or one or more symptoms thereof in a human patient comprising the steps of:

(a) analyzing one or more indicators of the responsiveness of the patient to NSI-189 or a pharmaceutically acceptable salt thereof as a treatment, wherein the one or more indicators include (i) objectively determined impaired learning and/or memory (e.g., impaired verbal memory), (ii) an electroencephalogram (EEG) with (A) a low aperiodic exponent, (B) a high power in the low gamma range (31-50 Hz), (C) a low power in the alpha frequency, or (D) any combination of any of (A), (B), and (C), or (iii) both (i) and (ii); and (b) where the patient is determined to be response to NSI-189 or a pharmaceutically acceptable salt thereof based on the one or more indicators, orally administering to the patient an effective amount of NSI-189 or a pharmaceutically acceptable salt thereof.

Yet another embodiment is a method of treating a major depressive episode in a human patient having objectively determined impaired learning and/or memory (e.g., impaired verbal memory) by orally administering to the patient from about 40 to about 240 mg of NSI-189 or a pharmaceutically acceptable salt thereof daily. In one embodiment, about 60 to about 100 mg of NSI-189 or a pharmaceutically acceptable salt thereof is administered daily. In one preferred embodiment, about 80 mg of NSI-189 or a pharmaceutically acceptable salt thereof is administered daily.

Yet another embodiment is a method for selecting a treatment for a major depressive episode in a human patient in need thereof and treating the patient. The method comprises:

(a) objectively assessing whether the patient has impaired learning and/or memory (e.g., impaired verbal memory) for the purpose of selecting a treatment for the patient; and (b) upon an assessment from step (a) that the patient has impaired learning and/or memory, initiating oral administration to the patient of from about 40 to about 240 mg of NSI-189 or a pharmaceutically acceptable salt thereof daily. In one embodiment, the method further comprises the step (c) of, upon an assessment from step (a) that the patient does not have impaired learning and/or memory, not initiating oral administration to the patient of from about 40 to about 240 mg of NSI-189 or a pharmaceutically acceptable salt thereof daily.

Yet another embodiment is a method for selecting a treatment for a major depressive episode in a human patient and treating the patient comprising:

(a) diagnosing a patient as suffering from a major depressive episode;

(b) objectively assessing whether the patient has impaired learning and/or memory (e.g., impaired verbal memory, for instance as determined by VM-REACT) for the purpose of selecting a treatment for the patient;

(c) selectively prescribing NSI-189 or a pharmaceutically acceptable salt thereof to the patient in view of the diagnosis of the patient and an objective assessment that the patient has impaired learning and/or memory; and (d) upon selectively prescribing NSI-189 or a pharmaceutically acceptable salt thereof, initiating oral administration to the patient of from about 40 to about 240 mg of NSI-189 or a pharmaceutically acceptable salt thereof daily.

Yet another embodiment is a method for determining whether a patient suffering from a major depressive episode can effectively be treated with NSI-189 and treating a human patient receptive to such treatment. The method comprises:

(a) objectively determining whether the patient has impaired learning and/or memory (e.g., impaired verbal memory); and (b) upon a determination from step (a) that the patient has impaired learning and/or memory, initiating oral administration to the patient of from about 40 to about 240 mg of NSI-189 or a pharmaceutically acceptable salt thereof daily. In one embodiment, the method further comprises the step (c) of, upon a determination from step (a) that the patient does not have impaired learning and/or memory, not initiating oral administration to the patient of from about 40 to about 240 mg of NSI-189 or a pharmaceutically acceptable salt thereof daily.

Yet another embodiment is a method of treating a major depressive episode in a human patient comprising the steps of:

(a) prescribing to the patient from about 40 to about 240 mg of NSI-189 or a pharmaceutically acceptable salt thereof daily, the prescribing being performed in response to (i) marketing of the NSI-189 or a pharmaceutically acceptable salt thereof as providing effective treatment of a major depressive episode in patients having objectively determined impaired learning and/or memory and (ii) an objective determination that the patient has impaired learning and/or memory (e.g., impaired verbal memory); and (b) orally administering the prescribed NSI-189 or a pharmaceutically acceptable salt thereof to the patient.

Yet another embodiment is a method of treating a major depressive episode in a human patient comprising the steps of:

(a) diagnosing a patient as suffering from a major depressive episode;

(b) prescribing to the patient from about 40 to about 240 mg of NSI-189 or a pharmaceutically acceptable salt thereof daily, the prescribing being performed in response to (i) marketing of the NSI-189 or a pharmaceutically acceptable salt thereof as providing effective treatment of a major depressive episode in patients having objectively determined impaired learning and/or memory (e.g., impaired verbal memory) and (ii) an objective determination that the patient has impaired learning and/or memory; and (c) orally administering the prescribed NSI-189 or a pharmaceutically acceptable salt thereof to the patient.

Yet another embodiment is a method of treating a major depressive episode in a human patient comprising the steps of:
  (a) analyzing one or more indicators of the responsiveness of the patient to NSI-189 or a pharmaceutically acceptable salt thereof as a treatment, wherein the one or more indicators include objectively determined impaired learning and/or memory; and
  (b) where the patient is determined to be response to NSI-189 or a pharmaceutically acceptable salt thereof based on the one or more indicators, orally administering to the patient an effective amount of NSI-189 or a pharmaceutically acceptable salt thereof.

Yet another embodiment is a method for selecting and initiating a treatment for a major depressive episode in a human patient and treating the patient comprising:
  (a) assessing, for the purpose of selecting a treatment for the patient, whether the patient has objectively determined impaired learning and/or memory (e.g., impaired verbal memory); and
  (b) upon an assessment from step (a) that the patient has objectively determined impaired learning and/or memory, initiating oral administration to the patient of from about 40 to about 240 mg of NSI-189 or a pharmaceutically acceptable salt thereof daily. In one embodiment, the method further comprises the step (c) upon an assessment from step (a) that the patient does not have objectively determined impaired learning and/or memory, not initiating oral administration to the patient of from about 40 to about 240 mg of NSI-189 or a pharmaceutically acceptable salt thereof daily.

Yet another embodiment is a method for selecting a treatment for a major depressive episode in a human patient and treating the patient comprising:
  (a) diagnosing a patient as suffering from a major depressive episode;
  (b) assessing, for the purpose of selecting a treatment for the patient, whether the patient has objectively determined impaired learning and/or memory (e.g., impaired verbal memory);
  (c) selectively prescribing NSI-189 or a pharmaceutically acceptable salt thereof to the patient in view of the diagnosis of the patient and an assessment that the patient has objectively determined impaired learning and/or memory; and
  (d) upon selectively prescribing NSI-189 or a pharmaceutically acceptable salt thereof, initiating oral administration to the patient of from about 40 to about 240 mg of NSI-189 or a pharmaceutically acceptable salt thereof daily.

Yet another embodiment is a method for determining whether a patient suffering from a major depressive episode can effectively be treated with NSI-189 and treating a human patient receptive to such treatment. The method comprises:
  (a) assessing, for the purpose of selecting a treatment for the patient, whether the patient has objectively determined impaired learning and/or memory (e.g., impaired verbal memory); and
  (b) upon a determination from step (a) that the patient has objectively determined impaired learning and/or memory, initiating oral administration to the patient of from about 40 to about 240 mg of NSI-189 or a pharmaceutically acceptable salt thereof daily. In one embodiment, the method further comprises the step (c) upon a determination from step (a) that the patient does not have objectively determined impaired learning and/or memory, not initiating oral administration to the patient of from about 40 to about 240 mg of NSI-189 or a pharmaceutically acceptable salt thereof daily.

Yet another embodiment is a method of treating a major depressive episode in a human patient comprising the steps of:
  (a) prescribing to the patient from about 40 to about 240 mg of NSI-189 or a pharmaceutically acceptable salt thereof daily, the prescribing being performed in response to marketing of the NSI-189 or a pharmaceutically acceptable salt thereof as providing effective treatment of a major depressive episode in patients having objectively determined impaired learning and/or memory (e.g., impaired verbal memory); and
  (b) orally administering the prescribed NSI-189 or a pharmaceutically acceptable salt thereof to the patient.

Yet another embodiment is a method of treating a major depressive episode in a human patient comprising the steps of:
  (a) diagnosing a patient as suffering from a major depressive episode;
  (b) prescribing to the patient from about 40 to about 240 mg of NSI-189 or a pharmaceutically acceptable salt thereof daily, the prescribing being performed in response to marketing of the NSI-189 or a pharmaceutically acceptable salt thereof as providing effective treatment of a major depressive episode in patients having objectively determined impaired learning and/or memory (e.g., impaired verbal memory); and
  (c) orally administering the prescribed (4-benzylpiperazin-1-yl)-[2-(3-methylbutylamino)pyridin-3-yl] methanone or a pharmaceutically acceptable salt thereof to the patient.

Yet another embodiment is a method of treating a major depressive episode in a human patient comprising the steps of:
  (a) analyzing one or more indicators of the responsiveness of the patient to NSI-189 or a pharmaceutically acceptable salt thereof as a treatment, wherein the one or more indicators include objectively determined impaired learning and/or memory (e.g., impaired verbal memory); and
  (b) where the patient is determined to be response to NSI-189 or a pharmaceutically acceptable salt thereof based on the one or more indicators, orally administering to the patient an effective amount of NSI-189 or a pharmaceutically acceptable salt thereof.

In one embodiment of any of the methods for treating a major depressive episode described herein, the patient suffers from major depressive disorder.

In one embodiment of any of the methods for treating a major depressive episode described herein, the patient suffers from bipolar depression.

In one embodiment of any of the methods for treating a major depressive episode described herein, the patient suffers from bipolar I disorder.

In one embodiment of any of the methods for treating a major depressive episode described herein, the patient suffers from bipolar II disorder.

Yet another embodiment is a method of treating bipolar depression in a human patient having objectively determined impaired learning and/or memory (e.g., impaired verbal memory) by orally administering to the patient from about 40 to about 240 mg of NSI-189 or a pharmaceutically acceptable salt thereof daily. In one embodiment, about 60 to about 100 mg of NSI-189 or a pharmaceutically acceptable salt thereof is administered daily. In one preferred embodiment, about 80 mg of NSI-189 or a pharmaceutically acceptable salt thereof is administered daily. In one embodiment, NSI-189 is administered as a monotherapy. In another embodiment, the patient is concurrently treated with one or more antipsychotic medications, mood stabilizers, or any combination of any of the foregoing. In one embodiment, the patient exhibits an electroencephalogram (EEG) with (i) a low aperiodic exponent, (ii) a high power in the low gamma range, (iii) a low power in the alpha frequency, or (iv) any combination of any of (i), (ii), and (iii).

Yet another embodiment is a method for selecting a treatment for bipolar depression in a human patient in need thereof and treating the patient. The method comprises:
  (a) assessing, for the purpose of selecting a treatment for the patient, whether the patient (i) has objectively determined impaired learning and/or memory (e.g., impaired verbal memory), (ii) exhibits an electroencephalogram (EEG) with (A) a low aperiodic exponent, (B) a high power in the low gamma range (31-50 Hz), (C) a low power in the alpha frequency, or (D) any combination of any of (A), (B), and (C), or (iii) both (i) and (ii); and
  (b) upon an assessment from step (a) that the patient meets (i), (ii), or (iii), initiating oral administration to the patient of from about 40 to about 240 mg of NSI-189 or a pharmaceutically acceptable salt thereof daily. In one embodiment, the method further comprises the step (c) of, upon an assessment from step (a) that the patient does not meet (i) or (ii), not initiating oral administration to the patient of from about 40 to about 240 mg of NSI-189 or a pharmaceutically acceptable salt thereof daily. In one embodiment, NSI-189 is administered as a monotherapy. In another embodiment, the patient is concurrently treated with one or more antipsychotic medications, mood stabilizers, or any combination of any of the foregoing.

Yet another embodiment is a method for selecting a treatment for bipolar depression in a human patient and treating the patient comprising:
  (a) diagnosing a patient as suffering from bipolar depression;
  (b) assessing, for the purpose of selecting a treatment for the patient, whether the patient (i) has objectively determined impaired learning and/or memory (e.g., impaired verbal memory), (ii) exhibits an electroencephalogram (EEG) with (A) a low aperiodic exponent, (B) a high power in the low gamma range (31-50 Hz), (C) a low power in the alpha frequency, or (D) any combination of any of (A), (B), and (C), or (iii) both (i) and (ii);
  (c) selectively prescribing NSI-189 or a pharmaceutically acceptable salt thereof to the patient in view of the diagnosis of the patient and an objective assessment that the patient meets (i), (ii), or (iii); and
  (d) upon selectively prescribing NSI-189 or a pharmaceutically acceptable salt thereof, initiating oral administration to the patient of from about 40 to about 240 mg of NSI-189 or a pharmaceutically acceptable salt thereof daily. In one embodiment, NSI-189 is administered as a monotherapy. In another embodiment, the patient is concurrently treated with one or more antipsychotic medications, mood stabilizers, or any combination of any of the foregoing.

Yet another embodiment is a method for determining whether a patient suffering from bipolar depression can effectively be treated with NSI-189 and treating a human patient receptive to such treatment. The method comprises:
  (a) assessing, for the purpose of selecting a treatment for the patient, whether the patient (i) has objectively determined impaired learning and/or memory (e.g., impaired verbal memory), (ii) exhibits an electroencephalogram (EEG) with (A) a low aperiodic exponent, (B) a high power in the low gamma range (31-50 Hz), (C) a low power in the alpha frequency, or (D) any combination of any of (A), (B), and (C), or (iii) both (i) and (ii); and
  (b) upon a determination from step (a) that the patient meets (i), (ii), or (iii), initiating oral administration to the patient of from about 40 to about 240 mg of NSI-189 or a pharmaceutically acceptable salt thereof daily. In one embodiment, the method further comprises the step (c) of, upon a determination from step (a) that the patient does not have impaired learning and/or memory, not initiating oral administration to the patient of from about 40 to about 240 mg of NSI-189 or a pharmaceutically acceptable salt thereof daily. In one embodiment, NSI-189 is administered as a monotherapy. In another embodiment, the patient is concurrently treated with one or more antipsychotic medications, mood stabilizers, or any combination of any of the foregoing.

Yet another embodiment is a method of treating bipolar depression in a human patient comprising the steps of:
  (a) prescribing to the patient from about 40 to about 240 mg of NSI-189 or a pharmaceutically acceptable salt thereof daily, the prescribing being performed in response to (I) marketing of the NSI-189 or a pharmaceutically acceptable salt thereof as providing effective treatment of bipolar depression in patients (i) having objectively determined impaired learning and/or memory (e.g., impaired verbal memory), (ii) that exhibit an electroencephalogram (EEG) with (A) a low aperiodic exponent, (B) a high power in the low gamma range (31-50 Hz)), (C) a low power in the alpha frequency, or (D) any combination of any of (A), (B), and (C), or (iii) both (i) and (ii); and (II) a determination that the patient meets (i), (ii) or (iii)
  (b) orally administering the prescribed NSI-189 or a pharmaceutically acceptable salt thereof to the patient. In one embodiment, NSI-189 is administered as a monotherapy. In another embodiment, the patient is concurrently treated with one or more antipsychotic medications, mood stabilizers, or any combination of any of the foregoing.

Yet another embodiment is a method of treating bipolar depression in a human patient comprising the steps of:
  (a) diagnosing a patient as suffering from bipolar depression;
  (b) prescribing to the patient from about 40 to about 240 mg of NSI-189 or a pharmaceutically acceptable salt thereof daily, the prescribing being performed in response to (i) marketing of the NSI-189 or a pharmaceutically acceptable salt thereof as providing effective treatment of bipolar depression in patients (i) having objectively determined impaired learning and/or memory (e.g., impaired verbal memory), (ii) that exhibit an electroencephalogram (EEG) with (A) a low aperiodic exponent, (B) a high power in the low gamma range (31-50 Hz)), (C) a low power in the alpha frequency, or (D) any combination of any of (A), (B), and (C), or (iii) both (i) and (ii) and (II) a determination that the patient meets (i), (ii), or (iii); and
  (c) orally administering the prescribed NSI-189 or a pharmaceutically acceptable salt thereof to the patient.

In one embodiment, NSI-189 is administered as a monotherapy. In another embodiment, the patient is concurrently treated with one or more antipsychotic medications, mood stabilizers, or any combination of any of the foregoing.

Yet another embodiment is a method of treating bipolar depression in a human patient comprising the steps of:
  (a) analyzing one or more indicators of the responsiveness of the patient to NSI-189 or a pharmaceutically acceptable salt thereof as a treatment, wherein the one or more indicators include (i) objectively determined impaired learning and/or memory (e.g., impaired verbal memory), (ii) an electroencephalogram (EEG) with (A) a low aperiodic exponent, (B) a high power in the low gamma range (31-50 Hz)), (C) a low power in the alpha frequency, or (D) any combination of any of (A), (B), and (C), or (iii) both (i) and (ii); and
  (b) where the patient is determined to be response to NSI-189 or a pharmaceutically acceptable salt thereof based on the one or more indicators, orally administering to the patient an effective amount of NSI-189 or a pharmaceutically acceptable salt thereof. In one embodiment, NSI-189 is administered as a monotherapy. In another embodiment, the patient is concurrently treated with one or more antipsychotic medications, mood stabilizers, or any combination of any of the foregoing.

Yet another embodiment is a method for selecting a treatment for bipolar depression in a human patient and treating the patient comprising:
  (a) assessing, for the purpose of selecting a treatment for the patient, whether the patient has objectively determined impaired learning and/or memory (e.g., impaired verbal memory); and
  (b) upon an assessment from step (a) that the patient has objectively determined impaired learning and/or memory, initiating oral administration to the patient of from about 40 to about 240 mg of NSI-189 or a pharmaceutically acceptable salt thereof daily. In one embodiment, the method further comprises the step (c) upon an assessment from step (a) that the patient does not have objectively determined impaired learning and/or memory, not initiating oral administration to the patient of from about 40 to about 240 mg of NSI-189 or a pharmaceutically acceptable salt thereof daily. In one embodiment, NSI-189 is administered as a monotherapy. In another embodiment, the patient is concurrently treated with one or more antipsychotic medications, mood stabilizers, or any combination of any of the foregoing.

Yet another embodiment is a method for selecting a treatment for bipolar depression in a human patient and treating the patient comprising:
  (a) diagnosing a patient as suffering from bipolar depression;
  (b) assessing, for the purpose of selecting a treatment for the patient, whether the patient (i) has objectively determined impaired learning and/or memory (e.g., impaired verbal memory);
  (c) selectively prescribing NSI-189 or a pharmaceutically acceptable salt thereof to the patient in view of the diagnosis of the patient and an assessment that the patient has objectively determined impaired learning and/or memory; and
  (d) upon selectively prescribing NSI-189 or a pharmaceutically acceptable salt thereof, initiating oral administration to the patient of from about 40 to about 240 mg of NSI-189 or a pharmaceutically acceptable salt thereof daily. In one embodiment, NSI-189 is administered as a monotherapy. In another embodiment, the patient is concurrently treated with one or more antipsychotic medications, mood stabilizers, or any combination of any of the foregoing.

Yet another embodiment is a method for determining whether a patient suffering from bipolar depression can effectively be treated with NSI-189 and treating a human patient receptive to such treatment. The method comprises:
  (a) assessing, for the purpose of selecting a treatment for the patient, whether the patient has objectively determined impaired learning and/or memory (e.g., impaired verbal memory); and
  (b) upon a determination from step (a) that the patient has objectively determined impaired learning and/or memory, initiating oral administration to the patient of from about 40 to about 240 mg of NSI-189 or a pharmaceutically acceptable salt thereof daily. In one embodiment, the method further comprises the step (c) upon a determination from step (a) that the patient does not have objectively determined impaired learning and/or memory, not initiating oral administration to the patient of from about 40 to about 240 mg of NSI-189 or a pharmaceutically acceptable salt thereof daily. In one embodiment, NSI-189 is administered as a monotherapy. In another embodiment, the patient is concurrently treated with one or more antipsychotic medications, mood stabilizers, or any combination of any of the foregoing.

Yet another embodiment is a method of treating bipolar depression in a human patient comprising the steps of:
  (a) prescribing to the patient from about 40 to about 240 mg of NSI-189 or a pharmaceutically acceptable salt thereof daily, the prescribing being performed in response to marketing of the NSI-189 or a pharmaceutically acceptable salt thereof as providing effective treatment of bipolar depression in patients having objectively determined impaired learning and/or memory (e.g., impaired verbal memory); and
  (b) orally administering the prescribed NSI-189 or a pharmaceutically acceptable salt thereof to the patient. In one embodiment, NSI-189 is administered as a monotherapy. In another embodiment, the patient is concurrently treated with one or more antipsychotic medications, mood stabilizers, or any combination of any of the foregoing.

Yet another embodiment is a method of treating bipolar depression in a human patient comprising the steps of:
  (a) diagnosing a patient as suffering from bipolar depression;
  (b) prescribing to the patient from about 40 to about 240 mg of NSI-189 or a pharmaceutically acceptable salt thereof daily, the prescribing being performed in response to marketing of the NSI-189 or a pharmaceutically acceptable salt thereof as providing effective treatment of bipolar depression in patients having objectively determined impaired learning and/or memory (e.g., impaired verbal memory); and
  (c) orally administering the prescribed (4-benzylpiperazin-1-yl)-[2-(3-methylbutylamino)pyridin-3-yl]methanone or a pharmaceutically acceptable salt thereof to the patient. In one embodiment, NSI-189 is administered as a monotherapy. In another embodiment, the patient is concurrently treated with one or more antipsychotic medications, mood stabilizers, or any combination of any of the foregoing.

Yet another embodiment is a method of treating bipolar depression in a human patient comprising the steps of:
  (a) analyzing one or more indicators of the responsiveness of the patient to NSI-189 or a pharmaceutically acceptable salt thereof as a treatment, wherein the one or more indicators include objectively determined impaired learning and/or memory (e.g., impaired verbal memory); and
  (b) where the patient is determined to be response to NSI-189 or a pharmaceutically acceptable salt thereof based on the one or more indicators, orally administering to the patient an effective amount of NSI-189 or a pharmaceutically acceptable salt thereof. In one embodiment, NSI-189 is administered as a monotherapy. In another embodiment, the patient is concurrently treated with one or more antipsychotic medications, mood stabilizers, or any combination of any of the foregoing.

Yet another embodiment is a method of treating post-traumatic stress disorder (PTSD) or one or more symptoms thereof in a human patient having objectively determined impaired learning and/or memory (e.g., impaired verbal memory) by orally administering to the patient from about 40 to about 240 mg of NSI-189 or a pharmaceutically acceptable salt thereof daily. In one embodiment, about 60 to about 100 mg of NSI-189 or a pharmaceutically acceptable salt thereof is administered daily. In one preferred embodiment, about 80 mg of NSI-189 or a pharmaceutically acceptable salt thereof is administered daily.

Yet another embodiment is a method for selecting a treatment for post-traumatic stress disorder (PTSD) or one or more symptoms thereof in a human patient in need thereof and treating the patient. The method comprises:
  (a) objectively assessing whether the patient has impaired learning and/or memory (e.g., impaired verbal memory) for the purpose of selecting a treatment for the patient; and
  (b) upon an assessment from step (a) that the patient has impaired learning and/or memory, initiating oral administration to the patient of from about 40 to about 240 mg of NSI-189 or a pharmaceutically acceptable salt thereof daily. In one embodiment, the method further comprises the step (c) of, upon an assessment from step (a) that the patient does not have impaired learning and/or memory, not initiating oral administration to the patient of from about 40 to about 240 mg of NSI-189 or a pharmaceutically acceptable salt thereof daily.

Yet another embodiment is a method for selecting a treatment for post-traumatic stress disorder (PTSD) or one or more symptoms thereof in a human patient and treating the patient comprising:
  (a) diagnosing a patient as suffering from post-traumatic stress disorder (PTSD);
  (b) objectively assessing whether the patient has impaired learning and/or memory (e.g., impaired verbal memory, for instance as determined by VM-REACT) for the purpose of selecting a treatment for the patient;
  (c) selectively prescribing NSI-189 or a pharmaceutically acceptable salt thereof to the patient in view of the diagnosis of the patient and an objective assessment that the patient has impaired learning and/or memory; and
  (d) upon selectively prescribing NSI-189 or a pharmaceutically acceptable salt thereof, initiating oral administration to the patient of from about 40 to about 240 mg of NSI-189 or a pharmaceutically acceptable salt thereof daily.

Yet another embodiment is a method for determining whether a patient suffering from post-traumatic stress disorder (PTSD) can effectively be treated with NSI-189 and treating a human patient receptive to such treatment. The method comprises:
  (a) objectively determining whether the patient has impaired learning and/or memory (e.g., impaired verbal memory); and
  (b) upon a determination from step (a) that the patient has impaired learning and/or memory, initiating oral administration to the patient of from about 40 to about 240 mg of NSI-189 or a pharmaceutically acceptable salt thereof daily. In one embodiment, the method further comprises the step (c) of, upon a determination from step (a) that the patient does not have impaired learning and/or memory, not initiating oral administration to the patient of from about 40 to about 240 mg of NSI-189 or a pharmaceutically acceptable salt thereof daily.

Yet another embodiment is a method of treating post-traumatic stress disorder (PTSD) or one or more symptoms thereof in a human patient comprising the steps of:
  (a) prescribing to the patient from about 40 to about 240 mg of NSI-189 or a pharmaceutically acceptable salt thereof daily, the prescribing being performed in response to (i) marketing of the NSI-189 or a pharmaceutically acceptable salt thereof as providing effective treatment of PTSD or a symptom thereof in patients having objectively determined impaired learning and/or memory and (ii) an objective determination that the patient has impaired learning and/or memory (e.g., impaired verbal memory); and
  (b) orally administering the prescribed NSI-189 or a pharmaceutically acceptable salt thereof to the patient.

Yet another embodiment is a method of treating post-traumatic stress disorder (PTSD) or one or more symptoms thereof in a human patient comprising the steps of:
  (a) diagnosing a patient as suffering from post-traumatic stress disorder (PTSD);
  (b) prescribing to the patient from about 40 to about 240 mg of NSI-189 or a pharmaceutically acceptable salt thereof daily, the prescribing being performed in response to (i) marketing of the NSI-189 or a pharmaceutically acceptable salt thereof as providing effective treatment of PTSD or a symptom thereof in patients having objectively determined impaired learning and/or memory (e.g., impaired verbal memory) and (ii) an objective determination that the patient has impaired learning and/or memory; and
  (c) orally administering the prescribed NSI-189 or a pharmaceutically acceptable salt thereof to the patient.

Yet another embodiment is a method of treating post-traumatic stress disorder (PTSD) or one or more symptoms thereof in a human patient comprising the steps of:
  (a) analyzing one or more indicators of the responsiveness of the patient to NSI-189 or a pharmaceutically acceptable salt thereof as a treatment, wherein the one or more indicators include objectively determined impaired learning and/or memory; and
  (b) where the patient is determined to be response to NSI-189 or a pharmaceutically acceptable salt thereof based on the one or more indicators, orally administering to the patient an effective amount of NSI-189 or a pharmaceutically acceptable salt thereof.

Yet another embodiment is a method for selecting a treatment for post-traumatic stress disorder (PTSD) or one or more symptoms thereof in a human patient and treating the patient comprising:
(a) assessing, for the purpose of selecting a treatment for the patient, whether the patient has objectively determined impaired learning and/or memory (e.g., impaired verbal memory); and
(b) upon an assessment from step (a) that the patient has objectively determined impaired learning and/or memory, initiating oral administration to the patient of from about 40 to about 240 mg of NSI-189 or a pharmaceutically acceptable salt thereof daily. In one embodiment, the method further comprises the step (c) upon an assessment from step (a) that the patient does not have objectively determined impaired learning and/or memory, not initiating oral administration to the patient of from about 40 to about 240 mg of NSI-189 or a pharmaceutically acceptable salt thereof daily.

Yet another embodiment is a method for selecting a treatment for post-traumatic stress disorder (PTSD) or one or more symptoms thereof in a human patient and treating the patient comprising:
(a) diagnosing a patient as suffering from post-traumatic stress disorder (PTSD);
(b) assessing, for the purpose of selecting a treatment for the patient, whether the patient (i) has objectively determined impaired learning and/or memory (e.g., impaired verbal memory);
(c) selectively prescribing NSI-189 or a pharmaceutically acceptable salt thereof to the patient in view of the diagnosis of the patient and an assessment that the patient has objectively determined impaired learning and/or memory; and
(d) upon selectively prescribing NSI-189 or a pharmaceutically acceptable salt thereof, initiating oral administration to the patient of from about 40 to about 240 mg of NSI-189 or a pharmaceutically acceptable salt thereof daily.

Yet another embodiment is a method for determining whether a patient suffering from PTSD can effectively be treated with NSI-189 and treating a human patient receptive to such treatment. The method comprises:
(a) assessing, for the purpose of selecting a treatment for the patient, whether the patient has objectively determined impaired learning and/or memory (e.g., impaired verbal memory); and
(b) upon a determination from step (a) that the patient has objectively determined impaired learning and/or memory, initiating oral administration to the patient of from about 40 to about 240 mg of NSI-189 or a pharmaceutically acceptable salt thereof daily. In one embodiment, the method further comprises the step (c) upon a determination from step (a) that the patient does not have objectively determined impaired learning and/or memory, not initiating oral administration to the patient of from about 40 to about 240 mg of NSI-189 or a pharmaceutically acceptable salt thereof daily.

Yet another embodiment is a method of treating post-traumatic stress disorder (PTSD) or one or more symptoms thereof in a human patient comprising the steps of:
(a) prescribing to the patient from about 40 to about 240 mg of NSI-189 or a pharmaceutically acceptable salt thereof daily, the prescribing being performed in response to marketing of the NSI-189 or a pharmaceutically acceptable salt thereof as providing effective treatment of PTSD or a symptom thereof in patients having objectively determined impaired learning and/or memory (e.g., impaired verbal memory); and
(b) orally administering the prescribed NSI-189 or a pharmaceutically acceptable salt thereof to the patient.

Yet another embodiment is a method of treating post-traumatic stress disorder (PTSD) or one or more symptoms thereof in a human patient comprising the steps of:
(a) diagnosing a patient as suffering from post-traumatic stress disorder (PTSD);
(b) prescribing to the patient from about 40 to about 240 mg of NSI-189 or a pharmaceutically acceptable salt thereof daily, the prescribing being performed in response to marketing of the NSI-189 or a pharmaceutically acceptable salt thereof as providing effective treatment of PTSD or a symptom thereof in patients having objectively determined impaired learning and/or memory (e.g., impaired verbal memory); and
(c) orally administering the prescribed (4-benzylpiperazin-1-yl)-[2-(3-methylbutylamino)pyridin-3-yl]methanone or a pharmaceutically acceptable salt thereof to the patient.

Yet another embodiment is a method of treating post-traumatic stress disorder (PTSD) or one or more symptoms thereof in a human patient comprising the steps of:
(a) analyzing one or more indicators of the responsiveness of the patient to NSI-189 or a pharmaceutically acceptable salt thereof as a treatment, wherein the one or more indicators include objectively determined impaired learning and/or memory (e.g., impaired verbal memory); and
(b) where the patient is determined to be response to NSI-189 or a pharmaceutically acceptable salt thereof based on the one or more indicators, orally administering to the patient an effective amount of NSI-189 or a pharmaceutically acceptable salt thereof.

Yet another embodiment is a method of prescribing NSA-189 to a patient suffering from major depressive disorder, post-traumatic stress disorder, both major depressive disorder and post-traumatic stress disorder, a major depressive episode, bipolar depression, or one or more symptoms thereof in a human patient comprising the steps of:
(a) objectively assessing whether the patient has impaired learning and/or memory (e.g., impaired verbal memory) for the purpose of selecting a treatment for the patient; and
(b) upon an assessment from step (a) that the patient has impaired learning and/or memory, prescribing to the patient from about 40 to about 240 mg of NSI-189 or a pharmaceutically acceptable salt thereof daily. In one embodiment, the method further comprises the step (c) upon an assessment from step (a) that the patient does not meet (i) or (ii), not prescribing NSI-189 to the patient.

Yet another embodiment is a method of prescribing NSI-189 to a patient suffering from major depressive disorder, bipolar depression, or one or more symptoms thereof in a human patient and treating the patient comprising:
(a) assessing whether the patient (i) has objectively determined impaired learning and/or memory (e.g., impaired verbal memory), (ii) exhibits an electroencephalogram (EEG) with (A) a low aperiodic exponent, (B) a high power in the low gamma range (31-50 Hz)), (C) a low power in the alpha frequency, or (D) any combination of any of (A), (B), and (C), or (iii) both (i) and (ii); and
(b) upon an assessment from step (a) that the patient meets (i), (ii), or (iii), prescribing to the patient from about 40 to about 240 mg of NSI-189 or a pharmaceutically acceptable salt thereof daily. In one embodiment, the method further comprises the step (c) upon an assessment from step (a) that the patient does not meet (i) or (ii), not prescribing NSI-189 to the patient.

In any of the methods described herein, in one embodiment, the patient is treated with NSI-189 or a pharmaceutically acceptable salt thereof as a monotherapy.

In any of the methods described herein, in one embodiment, the patient is concurrently treated with a second antidepressant medication (e.g., an SSRI, SNRI, mirtazapine, or bupropion) in addition to NSI-189 or a pharmaceutically acceptable salt thereof. In one embodiment, the patient is concurrently treated with an SSRI, SNRI, mirtazapine, or bupropion. In another embodiment, the patient is concurrently treated with an SSRI. In yet another embodiment, the patient is concurrently treated with an SNRI. In yet another embodiment, the patient is concurrently treated with mirtazapine. In yet another embodiment, the patient is concurrently treated with bupropion.

In any of the methods described herein, in one embodiment, the patient is concurrently treated with an antipsychotic in addition to NSI-189 or a pharmaceutically acceptable salt thereof. In one embodiment, the antipsychotic is quetiapine, cariprazine, aripiprazole, brexpiprazole, lumateperone, or olanzapine. In another embodiment, the antipsychotic is quetiapine, lurasidone, cariprazine, or a combination of olanzapine and fluoxetine. In yet another embodiment, the antipsychotic is a combination of brexpiprazole and sertraline. In yet another embodiment, for the treatment of major depressive disorder, the patient is concurrently treated with an antipsychotic selected from quetiapine, cariprazine, aripiprazole, brexpiprazole, and olanzapine, in addition to NSI-189 or a pharmaceutically acceptable salt thereof. In yet another embodiment, for the treatment of bipolar depression, the patient is concurrently treated with an antipsychotic selected from quetiapine, lurasidone, cariprazine, lumateperone, or a combination of olanzapine and fluoxetine, in addition to NSI-189 or a pharmaceutically acceptable salt thereof. In yet another embodiment, for the treatment of PTSD, the patient is concurrently treated with an antipsychotic which is a combination of brexpiprazole and sertraline, in addition to NSI-189 or a pharmaceutically acceptable salt thereof.

In any of the methods described herein, in one embodiment, prior to treatment with NSI-189 or a pharmaceutically acceptable salt thereof, the patient had an insufficient response to an antidepressant (e.g., an SSRI, SNRI, mirtazapine, or bupropion) other than NSI-189 or a pharmaceutically acceptable salt thereof. Such a patient may be concurrently treated with (i) NSI-189 or a pharmaceutically acceptable salt thereof and (ii) the antidepressant to which the patient had previously had an insufficient response. Alternatively, the patient may receive NSI-189 or a pharmaceutically acceptable salt thereof as monotherapy.

In any of the methods described herein, in one embodiment, the objectively assessed impaired learning and/or memory is calculated as a standardized score (e.g., z-scores, T-scores, Standard Scores, Scaled Scores, Percentile rank, or Stanine scores) normalizing the patient against a healthy population.

In any of the methods described herein, in one embodiment, the patient who has objectively determined impaired learning and/or memory and/or the aforementioned EEG characteristic(s) is administered from about 60 to about 100 mg/day of NSI-189 or a pharmaceutically acceptable salt thereof, such as about 80 mg/day of NSI-189 or a pharmaceutically acceptable salt thereof is administered to the patient. In one embodiment, such a patient is administered about 40 mg of NSI-189 or a pharmaceutically acceptable salt thereof twice daily.

In any of the methods described herein, in one embodiment, the NSI-189 or a pharmaceutically acceptable salt thereof is administered as (4-benzylpiperazin-1-yl)-[2-(3-methylbutylamino)pyridin-3-yl]methanone phosphate.

In any of the methods described herein, impaired learning and/or memory may be shown by one or more of the VM-REACT (Verbal Memory REcAll Computerized Test), The Rey Auditory Verbal Learning Test, California Verbal Learning Test (including the CVLT-II and CVLT-3), California Verbal Learning Test—Short Form, California Verbal Learning Test—Children's Version, Hopkins Verbal Learning Test, Hopkins Verbal Learning Test—Revised, Philadelphia Verbal Learning Test, International Shopping List Test, Verbal section of the Repeatable Battery for the Assessment of Neuropsychological Status, Cerad Neuropsychological Assessment Battery Word List Task, Children's Auditory Verbal Learning Test, Children's Memory Scale, Bay Area Verbal Learning Test, Cogstate battery (which can include the following subtests: Behavioral Pattern Separation Object Test, Continuous Paired Associate Learning Test, Face Name Associative Memory Exam, Groton Maze Learning Test and its Delayed Recall and Delayed Reverse Recall versions, International Shopping List, One Card Learning Test), CANTAB (which can include the following subtests: Delayed Matching to Sample, Pattern Recognition Memory, Verbal Paired Associates, Paired Associates Learning, Verbal Recognition Memory), Penn Computerized Neurocognitive Battery (which can include the following subtests: Penn Word Memory Task, Penn Face Memory Task, Visual Object Learning Test), the NIH Toolbox and its subtests (Face Name Associative Memory Exam Test, Picture Sequence Memory Test, and Rey Auditory Verbal Learning Test), Neuropsychological Assessment Battery Memory Module (which can include the following subtests and their delayed recall and recognition components: List Learning, Shape Learning, Story Learning, and Daily Living Memory), WHO/UCLA Auditory Verbal Learning Test, Repeatable Battery for the Assessment of Neuropsychological Status (which includes the following subtests and their delayed recall and recognition components: List Learning, Story Memory, and Figure Recall), Wide Range Assessment of Memory and Learning (which includes the following subtests and their delayed recall and recognition components: Picture Memory, Design Learning, Story Memory, and Verbal Learning), Buschke Selective Reminding Test, Wechsler Memory Scale (which includes the following subtests and their delayed recall and recognition components: Logical Memory, Verbal Paired Associates, Designs, and Visual Reproduction), Woodcock-Johnson Long Term Retrieval factor (which includes the following subtests and their delayed recall and recognition components: Story Recall and Visual-Auditory Learning), Test of Memory and Learning (which includes the following subtests and their delayed recall and recognition components: Memory for Stories, Facial Memory, Word Selective Reminding, Visual Selective Reminding, Abstract Visual Memory, Object Recall, Visual Sequential Memory, Paired Recall, and Memory for Location), NEPSY (which includes the following subtests and their delayed recall and recognition components: List Memory, Memory for Designs, Memory for Faces, Memory for Names, Narrative Memory, Sentence Repetition, and Word List Interference), Brief Visuospatial Memory Test—Revised, Benton Visual Retention Test, Rey Osterreith Complex Figure Test, and any combination of any of the foregoing. In one preferred embodiment, impaired learning and/or memory is evaluated by the VM-REACT. In one embodiment, a composite of two or more scores regarding impaired learning and/or memory is used to access impaired learning and/or memory in a patient.

In any of the methods described herein, impaired learning and/or memory may be shown by poor immediate recall in a verbal memory test, such as the VM-REACT. In other words, the patient has impaired learning and/or memory as objectively determined by poor immediate recall in a verbal memory test, such as the VM-REACT.

In any of the methods described herein, impaired learning and/or memory may be shown by poor delayed recall in a verbal memory test, such as the VM-REACT. In other words, the patient has impaired learning and/or memory as objectively determined by poor delayed recall in a verbal memory test, such as the VM-REACT.

In one embodiment of any of the methods described herein, the patient is not concurrently treated with a second antidepressant medication.

In another embodiment of any of the methods described herein, the patient is concurrently treated with a second antidepressant medication (e.g., an SSRI, SNRI, mirtazapine, or bupropion).

In yet another embodiment of any of the methods described herein, prior to treatment with NSI-189 or a pharmaceutically acceptable salt thereof, the patient had an insufficient response to an antidepressant (e.g., an SSRI, SNRI, mirtazapine, or bupropion) other than NSI-189 or a pharmaceutically acceptable salt thereof (e.g., a standard-of-care antidepressant). In one embodiment, the patient exhibited an insufficient response to the antidepressant (e.g., an SSRI, SNRI, mirtazapine, or bupropion) in the current depressive episode. In another embodiment, the patient continues treatment with the prior antidepressant concurrently with administration of NSI-189 or a pharmaceutically acceptable salt thereof.

In another embodiment of any of the methods described herein, the patient is concurrently treated with an antipsychotic medication, mood stabilizer, or combination thereof in addition to NSI-189 or a pharmaceutically acceptable salt thereof.

In one embodiment of any of the methods described herein, NSI-189 or a pharmaceutically acceptable salt thereof is administered daily such that, at steady state (such as 28 days after initiating treatment with NSI-189), the $C_{max}$ for NSI-189 is about 230 to about 630 ng/ml (e.g., about 300 to about 550 ng/ml). In another embodiment, NSI-189 or a pharmaceutically acceptable salt thereof is administered daily such that, at steady state (such as 28 days after initiating treatment with NSI-189), the $AUC_{0-24}$ for NSI-189 is about 1400 to about 3200 hr·ng/ml (e.g., about 1500 to about 3100 hr·ng/mL, about 1600 to about 3000 hr·ng/ml, about 1700 to about 2900 hr·ng/mL, or about 1800 to about 2800 hr·ng/mL). In yet another embodiment, NSI-189 or a pharmaceutically acceptable salt thereof is administered daily such that, at steady state (such as 28 days after initiating treatment with NSI-189), the $AUC_{0-tau}$ for NSI-189 is about 1200 to about 2050 hr·ng/ml (e.g., about 1400 to about 1850 hr·ng/ml).

In one embodiment of any of the methods described herein, the method comprises orally administering 40 mg of NSI-189 or a pharmaceutically acceptable salt thereof twice daily (b.i.d.). In one embodiment, the 40 mg b.i.d. administration provides, at steady state (such as 28 days after initiating treatment with NSI-189), a $C_{max}$ for NSI-189 of about 230 to about 630 ng/ml (e.g., about 300 to about 550 ng/ml). In another embodiment, the 40 mg b.i.d. administration provides, at steady state (such as 28 days after initiating treatment with NSI-189), an $AUC_{0-24}$ for NSI-189 of about 1400 to about 3200 hr·ng/ml (e.g., about 1500 to about 3100 hr·ng/ml, about 1600 to about 3000 hr·ng/ml, about 1700 to about 2900 hr·ng/mL, or about 1800 to about 2800 hr·ng/mL). In yet another embodiment, the 40 mg b.i.d. administration provides, at steady state (such as 28 days after initiating treatment with NSI-189), an $AUC_{0-tau}$ for NSI-189 of about 1200 to about 2050 hr·ng/ml (e.g., about 1400 to about 1850 hr·ng/ml).

In a preferred embodiment, about 80 mg of NSI-189 or a pharmaceutically acceptable salt thereof (such as NSI-189 phosphate) is administered daily.

The methods described herein can also be used to treat late-life depression in patients at least 50 years of age (e.g., at least 60 or 65 years old) (such as those with late life onset depression (first episode of depression after the age of 60)) instead of major depressive disorder.

The aforementioned methods may be used for treating one or more symptoms including depressive symptoms, anhedonia, loss of interest, avolition, diminished emotional expression, inability to feel, amotivation, apathy, slow thinking, psychomotor retardation, lassitude, or any combination of any of the foregoing, in a human patient suffering from post-traumatic stress disorder (PTSD), bipolar depression, substance use disorder, or schizophrenia instead of major depressive disorder. For instance, in one embodiment, the methods described herein are used to treat depressive symptoms of major depressive disorder, bipolar depression (such as bipolar I or bipolar II disorders), post-traumatic stress disorder, substance use disorder and depression-related aspects of schizophrenia (e.g., negative symptoms) in patients in need thereof. For example, the methods can be used to treat depressive symptoms of bipolar I depression in a patient suffering from bipolar I depression (but not major depressive disorder).

In yet another embodiment, the patient is concurrently treated with one or more antidepressants (other than NSI-189 or a pharmaceutically acceptable salt thereof) (e.g., an SSRI, SNRI, mirtazapine, or bupropion). In yet another embodiment, the patient is concurrently treated with one or more antipsychotic medications, mood stabilizers, or any combination of any of the foregoing.

Yet another embodiment is a method of treating one or more symptoms including depressive symptoms, anhedonia, loss of interest, avolition, diminished emotional expression, inability to feel, amotivation, apathy, slow thinking, psychomotor retardation, lassitude, or any combination of any of the foregoing, in a human patient suffering from post-traumatic stress disorder (PTSD), bipolar depression, substance use disorder, or schizophrenia comprising (a) assessing, for the purpose of selecting a treatment for the patient, whether the patient (i) has objectively determined impaired learning and/or memory, (ii) exhibits an electroencephalogram (EEG) with (A) a low aperiodic exponent, (B) a high power in the low gamma range (31-50 Hz)), (C) a low power in the alpha frequency, or (D) any combination of any of (A), (B), and (C), or (iii) both (i) and (ii); and (b) upon the patient having objectively determined impaired learning and/or memory or exhibiting an electroencephalogram (EEG) with (A) a low aperiodic exponent, (B) a high power in the low gamma range (31-50 Hz)), (C) a low power in the alpha frequency, or (D) any combination of any of (A), (B), and (C), administering to the patient an effective amount of NSI-189 or a pharmaceutically acceptable salt thereof (e.g., oral administering from about 40 to about 120, 160, or 240 mg, such as about 40 to about 120 mg, from about 60 mg to about 100 mg, or about 80 mg of NSI-189 or a pharmaceutically acceptable salt thereof daily).

The aforementioned methods may be used for treating negative symptoms of schizophrenia in a human patient instead of major depressive disorder. In another embodiment, the patient is not concurrently treated with an antidepressant medication (other than NSI-189) (e.g., an SSRI, SNRI, mirtazapine, or bupropion). In yet another embodiment, the patient is concurrently treated with one or more antidepressants (other than NSI-189 or a pharmaceutically acceptable salt thereof), an antipsychotic, or mood stabilizer, or any combination of the foregoing.

One embodiment is a method of treating major depressive disorder, bipolar disorder, late-life depression, schizophrenia, posttraumatic stress disorder, substance use disorder, depressive symptoms (such as depressive symptoms of any of the foregoing disorders) or negative symptoms (such as negative symptoms of schizophrenia) in a patient comprising:
(a) receiving data comprised of one or more neurophysiological measures, including EEG measures (e.g., (A) an aperiodic exponent, (B) a high power in the low gamma range (31-50 Hz)), (C) a low power in the alpha frequency, or (D) any combination of any of (A), (B), and (C)), of the patient;
(b) optionally, receiving data comprised of one or more indicators of cognitive impairment, slow or poor cognition or difficulty making decisions in the patient (e.g., one or more indicators of impaired learning and/or memory, such as impaired verbal memory); and
(c) administering to the patient an effective amount of NSI-189 or a pharmaceutically acceptable salt thereof, where the patient is determined to be responsive to NSI-189 based on the data comprised of the one or more neurophysiological measures and optionally the one or more indicators of cognitive impairment, slow or poor cognition or difficulty making decisions (e.g., one or more indicators of impaired learning and/or memory). In one embodiment, the patient suffers from bipolar disorder, late-life depression, schizophrenia, posttraumatic stress disorder, or substance use disorder in which depressive symptoms are prominent. In another embodiment, the patient suffers from major depressive disorder. In one embodiment, the patient is concurrently treated with one or more antidepressants (other than NSI-189 or a pharmaceutically acceptable salt thereof), antipsychotics, mood stabilizers, or any combination of any of the foregoing. In another embodiment, the patient is not concurrently treated with an antidepressant medication (other than NSI-189).

The neurophysiological measure can be a measure of brain activity, such as with electroencephalogram (EEG) recordings. The electroencephalogram (EEG) recordings can measure power of one or more frequencies, relative power across frequencies, power ratios between frequencies (e.g. theta-gamma power ratio), cordance, power envelope connectivity, coherence, imaginary coherence, phase locking value, phase lag index, weighted phase lag index, spatial covariance, spectrally-normalized spatial covariance, cross-frequency coupling, aperiodic exponent, alpha peak frequency, alpha peak frequency proximity, or information theoretical indices and entropies. In one embodiment, the EEG recording of the patient exhibits low power at the centro-parietal electrodes in the theta frequencies, low power at the centro-parietal electrodes in the alpha frequencies, low power at the frontal electrodes in the alpha frequencies, high aperiodic exponent at one or more posterior electrodes, or any combination of any of the foregoing.

The one or more indicators of cognitive impairment, slow or poor cognition or difficulty making decisions can include impaired learning and/or memory (such as impaired verbal memory). The one or more indicators of cognitive impairment, slow or poor cognition or difficulty making decisions can include, e.g., one or more measurements from a simple reaction time task, a choice reaction time task, a one-back working memory task, verbal learning and/or memory task, and a visual learning task, and a self-report questionnaire. In a preferred embodiment, the one or more indicators include measurement of learning and/or memory (e.g., VM-REACT), such as verbal memory. The indicators can also include those for learning and/or memory described herein, including the learning and/or memory tests described herein (such as VM-REACT). In one preferred embodiment, the indicator is impaired learning and/or memory as assessed by VM-REACT. Other indicators include, e.g., one or more measurements from a Mini Mental Status Exam (MMSE), Montreal Cognitive Assessment (MoCA), Repeatable Battery for the Assessment of Neuropsychological Status (RBANS), Dementia Rating Scale (DRS), Cambridge Neuropsychological Test Automated Batteries (CANTAB) and its subtests (i.e., Motor Screening, Matching to Sample Visual Search, Delayed Matching to Sample, Pattern Recognition Memory Immediate/Delayed, Spatial Recognition Memory, Paired Associate Learning, Spatial Span, Spatial Working Memory, Big Little Circle, Intra/Extradimensional Shift, Rapid Visual Processing, Reating Time, and Stockings of Cambridge), TabCAT and its subtests (i.e., dot counting, flanker, match, Running Dots, Set Shifting, Tempo, Favorites, Animal Fluency, Rapid Naming, and Quick Tap), NIH Examiner and its subtests (Dot Counting, N-Back, Flanker, Continuous Performance Test, Dysexecutive Errors, Set Shifting, Phonemic Fluency, Category Fluency, Unstructured Task, and Insight), NIH Toolbox and its subtests (Dimensional Change Card Sort Test, Face Name Associative Memory Exam Test, Flanker Inhibitory Control and Attention Test, List Sorting Working Memory Test, Oral Reading Recognition Test, Oral Symbol Digit Test, Pattern Comparison Processing Speed Test, Picture Sequence Memory Test, Picture Vocabulary Test, Rey Auditory Verbal Learning Test, Speeded Matching Test, and Visual Reasoning Test), Penn Computerized Neuropsychological Neurocognitive Battery and its subtests (Penn Conditional Exclusion Test, Penn Continuous Performance Test, Letter N-Back Task, Penn Word Memory Task, Penn Face Memory Task, Visual Object Learning Test, Penn Verbal Reasoning Test, Penn Matrix Reasoning Test, Penn Line Orientation Test, Penn Emotion Identification Test, Penn Emotion Differentiation Test, and Penn Age Differentiation Test), Cogstate battery and its subtests (Behavioral Pattern Separation Object Test, Continuous Paired Associate Learning Test, Detection Test, Face Name Associative Memory Exam, Finger Tapping Test, Groton Maze Learning Test, Identification Test, International Daily Symbol Substitution Test—Medicines, International Digit Symbol Substitution Test—Symbols, International Shopping List Test, One Back Test, One Card Learning Test, Psychomotor Vigilance Test, Social-Emotional Cognition Test, Sustained Attention Test, Sustained Attention to Response Test, and Two Back Test), Digit symbol substitution task, Oddball task, Flanker task, Wisconsin card sort task, Modified (Wisconsin) Card Sort task, Delis-Kaplan Executive Function System (D-KEFS) Sorting task, Category Test, Trail making task, D-KEFS Trail-Making Test, Spatial/Corsi Block task, Digit Span task, Backwards Digit Span task, Verbal Fluency task, D-KEFS Verbal Fluency Test, Figural/Design Fluency task, D-KEFS design fluency Test, symbol digit modalities test, Continuous Performance Test (CPT), Wechsler Adult Intelligence Scale (WAIS) coding subtest, digit vigilance test, d2 test of attention, WAIS symbol search subtest, WAIS cancellation subtest, Neuropsychological Assessment Battery (NAB) Numbers and letters subtest, NAB Digit Span subtest, Ruff 2&7 selective attention test, Stroop Color/Word test, NAB mazes and other maze tests, Spatial planning/Tower tests, Stroop test, D-KEFS Color-Word Interference Test, or Repeatable Battery for the Assessment of Neuropsychological Status (RBANS) coding subtest. In one embodiment, the indicators include one or more measurements from a typing fluency test, a verbal fluency test (such as Verbal Fluency task or D-KEFS Verbal Fluency Test), simple reaction time, choice reaction time, digit symbol substitution task, Trail-making task test (parts A and B), Wisconsin card sort task, and Flanker task. The one or more indicators of cognitive impairment can be calculated as standardized scores (e.g., z-scores, T-scores, Standard Scores, Scaled Scores, Percentile rank, Stanine scores) normalizing the patient against a healthy population. In one embodiment, the one or more indicators of cognitive impairment, slow or poor cognition (e.g., impaired memory and/or learning), and/or difficulty making decisions are merged into a composite cognitive task performance score.

In one embodiment, machine learning or multivariate modeling (such as described in International Publication No. WO 2020/081609 and U.S. Patent Publication Nos. 2021/0038150, 2019/126055, 2020/054888, and 2020/0401938, each of which is hereby incorporated by reference) is applied to predict the responsiveness of the patient to the administration of NSI-189.

In one embodiment of any of the methods described herein, from about 40 to about 120, 160, or 240 mg/day of NSI-189 or a pharmaceutically acceptable salt thereof is administered to the patient. For instance, from about 40 to about 120 mg, from about 60 to about 120 mg/day, from about 70 to about 120 mg/day, or from about 80 to about 100 mg/day of NSI-189 or a pharmaceutically acceptable salt thereof is administered to the patient. In a preferred embodiment, about 80 mg/day of NSI-189 or a pharmaceutically acceptable salt thereof is administered to the patient. In any of the methods described herein, the preferred administration route is orally.

In one embodiment of any of the aforementioned methods, the patient has previously been treated with one or more antidepressants (e.g., an SSRI, SNRI, mirtazapine, or bupropion) but failed to respond to them, and continues to be treated with the one or more antidepressants even after NSI-189 (or a pharmaceutically acceptable salt thereof) treatment is begun. In other words, the NSI-189 or a pharmaceutically acceptable salt thereof is provided as an adjunctive therapy to the one or more antidepressants (e.g., an SSRI, SNRI, mirtazapine, or bupropion). In one embodiment, the one or more antidepressants do not include a monoamine oxidase inhibitor (MAOI) or a tricyclic antidepressant. In another embodiment, the one or more antidepressants are selected from serotonin reuptake inhibitors, serotonin and norepinephrine reuptake inhibitors, mirtazapine, bupropion, and any combination of any of the foregoing. The patient may suffer from major depressive disorder. In one embodiment, 40 mg of the NSI-189 or a pharmaceutically acceptable salt thereof, such as NSI-189 phosphate, is orally administered twice daily.

In one embodiment of any of the aforementioned methods, the patient has bipolar depression and has previously been treated with one or more mood stabilizers, antipsychotic medications, or any combination of any of the foregoing but failed to respond to them, and continues to be treated with the one or more mood stabilizers, antipsychotic medications, or any combination of any of the foregoing even after NSI-189 (or a pharmaceutically acceptable salt thereof) treatment is begun. In other words, the NSI-189 or a pharmaceutically acceptable salt thereof is provided as an adjunctive therapy to the one or more mood stabilizers, antipsychotic medications, or any combination of any of the foregoing. In one embodiment, 40 mg of the NSI-189 or a pharmaceutically acceptable salt thereof, such as NSI-189 phosphate, is orally administered twice daily.

In one embodiment, the patient suffers from anhedonia. In another embodiment, the patient suffers from suicidality.

In another embodiment of any of the methods described herein, the patient suffers from both major depressive disorder and post-traumatic stress disorder.

Yet another embodiment is a system comprising:
at least one data processor; and
at least one memory storing instructions which, when executed by the at least one data processor, result in operations comprising:
(a) receiving data comprised of one or more neurophysiological measures (such as those described herein) in a patient;
(b) optionally, receiving data comprised of one or more indicators of cognitive impairment or poor cognition (such as those described herein, including impairment of learning and/or memory) in the patient;
(c) analyzing, using a multivariate model (e.g., a machine learning model), (i) the data comprised of one or more neurophysiological measures in the patient and (ii) optionally the data comprised of one or more indicators of cognitive impairment or poor cognition, to predict the responsiveness of the patient to NSI-189; and
(d) outputting a prediction of the responsiveness of the patient to NSI-189 based on the analyzed data.

Prior to step (c), the multivariate model (such as machine learning model) may be used to analyze data from prior patients receiving NSI-189 (or a pharmaceutically acceptable salt thereof) and one or more of their neurophysiological measures and optionally one of more of their indicators of cognitive impairment (such as impairment of learning and/or memory).

In one embodiment, the instructions result in operations further comprising outputting a recommendation to administer an effective amount of NSI-189 or a pharmaceutically acceptable salt thereof.

The neurophysiological measure can be electroencephalogram (EEG) recordings, such as EEG recordings. The electroencephalogram (EEG) recordings can measure power of one or more frequencies, relative power across frequencies, power ratios between frequencies, cordance, power envelope connectivity, coherence, imaginary coherence, phase locking value, phase lag index, weighted phase lag index, spatial covariance, cross-frequency coupling, aperiodic exponent, alpha peak frequency, spectrally-normalized spatial covariance, alpha peak frequency coherence, or information theoretical indices and entropy. In one embodiment, the EEG recording of the patient exhibits low power at the centro-parietal electrodes in the theta frequencies, low power at the centro-parietal electrodes in the alpha frequencies, low power at the frontal electrodes in the alpha frequencies, high aperiodic exponent at one or more posterior electrodes, or any combination of any of the foregoing.

The one or more indicators of cognitive impairment, slow or poor cognition, impaired learning and/or memory (such as impaired verbal memory), and/or difficulty making decisions can include one or more measurements from a simple reaction time task, a choice reaction time task, a one-back working memory task, verbal memory task, and a visual learning task, and a self-report questionnaire. In a preferred embodiment, the one or more indicators include measurement of learning and/or memory (e.g., VM-REACT), such as verbal memory. The indicators can also include those for learning and/or memory described herein. Other indicators include one or more measurements from a Mini Mental Status Exam (MMSE), Montreal Cognitive Assessment (MoCA), Repeatable Battery for the Assessment of Neuropsychological Status (RBANS), Dementia Rating Scale (DRS), Cambridge Neuropsychological Test Automated Batteries (CANTAB) and its subtests (i.e., Motor Screening, Matching to Sample Visual Search, Delayed Matching to Sample, Pattern Recognition Memory Immediate/Delayed, Spatial Recognition Memory, Paired Associate Learning, Spatial Span, Spatial Working Memory, Big Little Circle, Intra/Extradimensional Shift, Rapid Visual Processing, Reating Time, and Stockings of Cambridge), TabCAT and its subtests (i.e., dot counting, flanker, match, Running Dots, Set Shifting, Tempo, Favorites, Animal Fluency, Rapid Naming, and Quick Tap), NIH Examiner and its subtests (Dot Counting, N-Back, Flanker, Continuous Performance Test, Dysexecutive Errors, Set Shifting, Phonemic Fluency, Category Fluency, Unstructured Task, and Insight), NIH Toolbox and its subtests (Dimensional Change Card Sort Test, Face Name Associative Memory Exam Test, Flanker Inhibitory Control and Attention Test, List Sorting Working Memory Test, Oral Reading Recognition Test, Oral Symbol Digit Test, Pattern Comparison Processing Speed Test, Picture Sequence Memory Test, Picture Vocabulary Test, Rey Auditory Verbal Learning Test, Speeded Matching Test, and Visual Reasoning Test), Penn Computerized Neuropsychological Neurocognitive Battery and its subtests (Penn Conditional Exclusion Test, Penn Continuous Performance Test, Letter N-Back Task, Penn Word Memory Task, Penn Face Memory Task, Visual Object Learning Test, Penn Verbal Reasoning Test, Penn Matrix Reasoning Test, Penn Line Orientation Test, Penn Emotion Identification Test, Penn Emotion Differentiation Test, and Penn Age Differentiation Test), Cogstate battery and its subtests (Behavioral Pattern Separation Object Test, Continuous Paired Associate Learning Test, Detection Test, Face Name Associative Memory Exam, Finger Tapping Test, Groton Maze Learning Test, Identification Test, International Daily Symbol Substitution Test-Medicines, International Digit Symbol Substitution Test—Symbols, International Shopping List Test, One Back Test, One Card Learning Test, Psychomotor Vigilance Test, Social-Emotional Cognition Test, Sustained Attention Test, Sustained Attention to Response Test, and Two Back Test), Digit symbol substitution task, Oddball task, Flanker task, Wisconsin card sort task, Trail making task, Corsi Block task, Digit Span task, Reverse Digit Span task, Verbal Learning and Memory task, Verbal Fluency task, symbol digit modalities test, Continuous Performance Test (CPT), Wechsler Adult Intelligence Scale (WAIS) coding subtest, digit vigilance test, d2 test of attention, WAIS symbol search subtest, WAIS cancellation subtest, Neuropsychological Assessment Battery (NAB) Numbers and letters subtest, NAB Digit Span subtest, Ruff 2&7 selective attention test, Stroop Color/Word test, NAB mazes and other maze tests, Delis-Kaplan Executive Function System (D-KEFS) design fluency subtest, or Repeatable Battery for the Assessment of Neuropsychological Status (RBANS) coding subtest. The one or more indicators of cognitive impairment, slow or poor cognition or difficulty making decisions can be calculated as standardized scores (e.g., z-scores, T-scores, Standard Scores, Scaled Scores, Percentile rank, and Stanine scores) normalizing the patient against a healthy population. These standardized scores may be calculated based on measurements such as reaction time, accuracy, memory recall accuracy, items recalled, and variation in reaction time. In one embodiment, the one or more indicators of cognitive impairment, slow or poor cognition or difficulty making decisions are merged into a composite cognitive task performance score. In one embodiment, a composite of two or more scores regarding impaired learning and/or memory is used to access impaired learning and/or memory in a patient.

In one embodiment, machine learning or multivariate modeling is applied to predict the responsiveness of the patient to the administration of NSI-189.

In one embodiment, from about 10 to about 130 mg/day of NSI-189 or a pharmaceutically acceptable salt thereof is administered to the patient. For instance, from about 20 to about 120 mg/day, from about 80 to about 120 mg/day, or from about 10 to about 40 mg/day of NSI-189 or a pharmaceutically acceptable salt thereof is administered to the patient. In a preferred embodiment, about 80 mg/day of NSI-189 or a pharmaceutically acceptable salt thereof is administered to the patient.

In one embodiment in any of the methods described herein, measured reduced executive function and/or attention function can be used in lieu of objectively impaired learning and/or memory. For example, one embodiment is a method of treating major depressive disorder, PTSD, bipolar depression, or one or more symptoms thereof in a human patient having measured reduced executive function and/or attention function comprising orally administering to the patient from about 40 to about 240 mg of (4-benzylpiperazin-1-yl)-[2-(3-methylbutylamino)pyridin-3-yl]methanone or a pharmaceutically acceptable salt thereof daily.

BRIEF DESCRIPTION OF THE DRAWINGS

For a more complete understanding of the present invention, including features and advantages, reference is now made to the detailed description of the invention along with the accompanying figures.

FIG. 7 shows the mean, standard error of the mean (SEM) and p-values for t-tests comparing various cognitive measures between poor cognition patients (recall index scores of z≤-0.75) to good cognition patients (scores z>-0.75) in Example 2. Poor cognition patients, even when defined by a single measure such as learning and memory, nonetheless have poorer cognition (more negative z-scores) across a wide range of cognitive tests and domains. DSST=digit-symbol substitution task, RT=reaction time, FERT=facial emotion recognition test.

FIG. 8 also has a graph (C) of drug-placebo differences (plotted as Cohen's d values) for poor learning and memory patients in the second Phase 2 study and poor cognition patients in the first Phase 2 study relative to drug-placebo differences reported in all-comer depression populations receiving a range of approved antidepressants or agents used in augmentation of or adjunctively to antidepressants (e.g., antipsychotics).

DETAILED DESCRIPTION OF THE INVENTION

Figure 1:
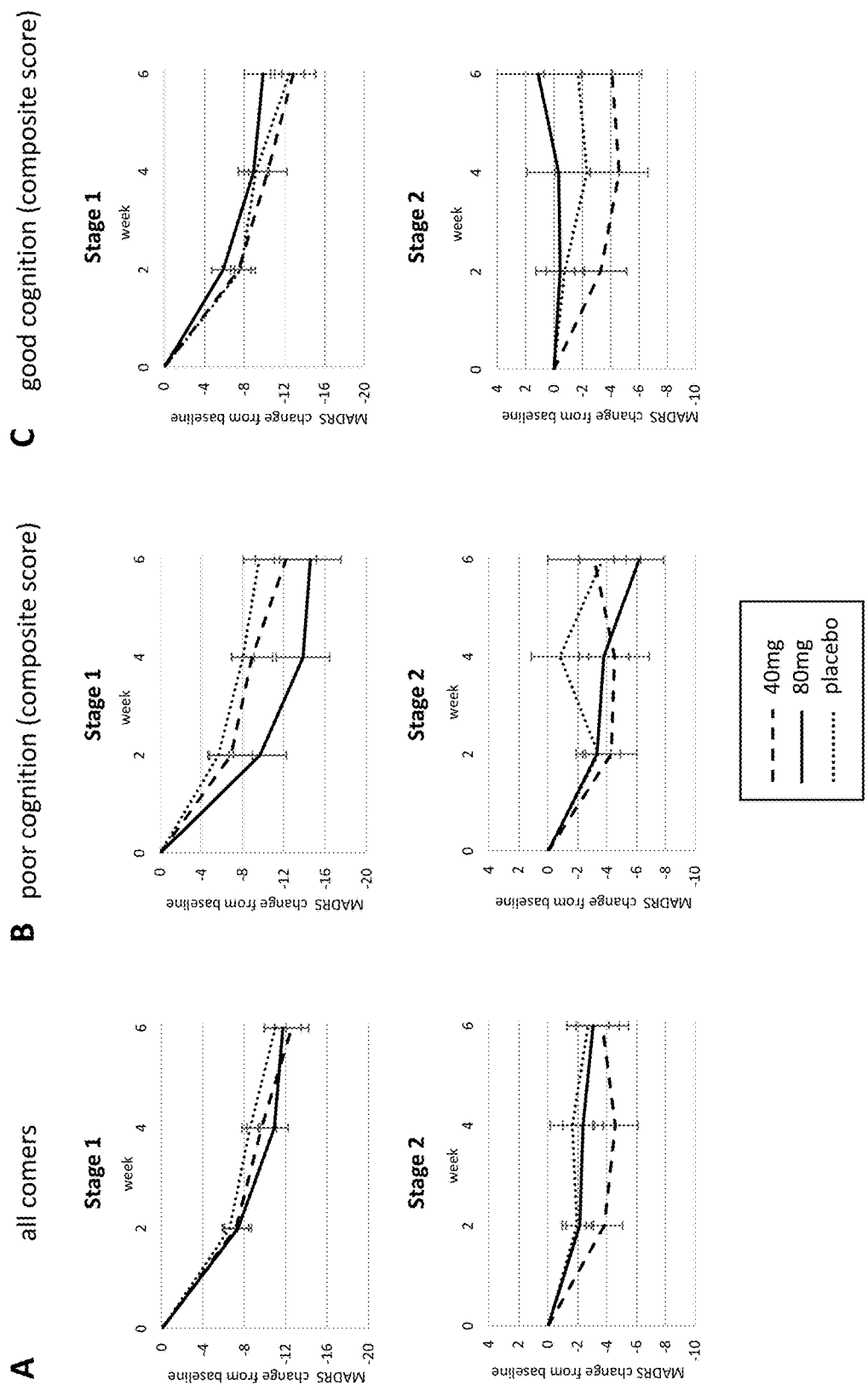
FIG. 1 has graphs showing the change in MADRS depression scores in Example 1 from baseline during stage 1 and stage 2 in (A) all patients (i.e., all-comers analysis), (B) poor cognition patients (as defined by the cognitive composite score being below the patient mean), and (C) good cognition patients (as defined by the cognitive composite score being above the patient mean) receiving placebo or 40 or 80 mg NSI-189.

Unless specifically stated or obvious from context, as used herein, the term "or" is understood to be inclusive.

Unless specifically stated or obvious from context, as used herein, the terms "a", "an", and "the" are understood to be singular or plural.

Ranges provided herein are understood to be shorthand for all of the values within the range.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term about.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

The term "monotherapy" refers to treatment with a single active agent.

Unless indicated otherwise, the term "NSI-189" refers to (4-benzylpiperazin-1-yl)-[2-(3-methylbutylamino)pyridin-3-yl]methanone, which has the structure:

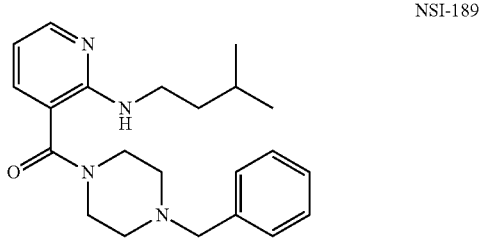 [SMILES: CC(C)CCNc1ncccc1C(=O)N1CCN(Cc2ccccc2)CC1]

NSI-189

NSI-189 can be synthesized as described in U.S. Pat. Nos. 7,560,553, 7,858,628, 9,278,933, and 9,572,807, each of which is incorporated by reference in its entirety. Pharmaceutically acceptable salts of NSI-189 include, but are not limited to, halides, maleates, succinates, nitrates, and phosphates. A preferred pharmaceutically acceptable salt of NSI-189 is (4-benzylpiperazin-1-yl)-[2-(3-methylbutylamino) pyridin-3-yl]methanone phosphate (such as (4-benzylpiperazin-1-yl)-[2-(3-methylbutylamino)pyridin-3-yl]methanone monophosphate also referred to as NSI-189 phosphate). NSI-189 or its pharmaceutically acceptable salt can be administered in the form of a dosage form containing one or more pharmaceutically acceptable excipients, such as an oral dosage form (e.g., a tablet, capsule, granules, or oral liquid).

The terms major depressive disorder, bipolar disorder (including bipolar I disorder and bipolar II disorder), post-traumatic stress disorder, substance use disorder and schizophrenia are intended to be as defined in the *Diagnostic and Statistical Manual of Mental Disorders, 5th Ed.* text revision ("DSM-5-TR"), American Psychiatric Association, 2022, which is hereby incorporated by reference. The term "bipolar depression" generally refers to depressive episodes associated with bipolar I or II disorder. Bipolar disorder with depression (BD-D) is based on SCID-5 (Structured Clinical Interview for DSM-5).

As used herein, the term "brain activity" or "brain activity levels" refer to measurable (e.g., quantifiable) neural activity. Measurable neural activity includes, but is not limited to, a magnitude of activity, a frequency of activity, a delay of activity, or a duration of activity. Brain activity levels may be measured (e.g., quantified) during periods in which no stimulus is presented. In embodiments, the brain activity level measured in the absence of a stimulus is referred to as a baseline brain activity level. This may be done with eyes closed or eyes open. Alternatively, brain activity levels may be measured (e.g., quantified) when one or more stimuli are delivered (e.g., an emotional conflict task). In embodiments, the brain activity level measured in the presence of a stimulus is referred to as a brain activity level response. Brain activity levels may be measured simultaneously or sequentially throughout the whole brain, or restricted to specific brain regions (e.g., frontopolar cortex, lateral prefrontal cortex, dorsal anterior cingulate, and anterior insula). In embodiments, the brain activity level is determined relative to a baseline brain activity level taken during a baseline period. The baseline period is typically a period during which a stimulus is not presented or has not been presented for a sufficient amount of time (e.g., great than at least 0.05, 0.1, 0.15, 0.25, 0.5, 1, 2, 3, 4, 5, 10, 15, 30, 60 seconds or more).

A brain activity level may also encompass evaluating functional brain region connectivity. For example, neural activity recorded in a plurality of brain regions may have a specific time course across brain regions that can be correlated to reveal a functional brain connectivity pattern (e.g., at a first time point a first brain regions shows an increase in neural activity and at a second time point a second brain region shows an increase in activity). Thus, in embodiments, a brain activity level is a measurement (e.g., quantification) of a time course of neural activity across a plurality of brain regions. In embodiments, a brain activity level is a sequence of brain region activity levels measured (e.g., quantified) across different brain regions over time. In embodiments, a brain activity level is a functional brain region connectivity pattern.

The term "electroencephalography (EEG)" refers to a non-invasive neurophysiological technique that uses an electronic monitoring device to measure and record electrical activity in the brain. The power and aperiodic exponent may be measured across central electrodes or fronto-centro-parietal electrodes. The reference to "low power" or "high power" in a given frequency range (such as the low gamma range (e.g., 31-50 Hz), 31-60 Hz, or 35-45 Hz)) refers to a power (e.g., calculated as a standardized score, such as a z-score) below or above, respectively, that of the $50^{th}$ percentile, or a lower or higher cutoff, of healthy individuals of similar demographics, such as based on similarity in age to patients. The term "low aperiodic exponent" refers to an aperiodic exponent (e.g., calculated as a standardized score, such as a z-score) below that of the $50^{th}$ percentile, or a lower cutoff, of healthy individuals of similar demographics, such as based on similarity in age to patients. For example, the subject may have a low alpha power or a low aperiodic exponent value below the $50^{th}$ percentile of a similar healthy subject with a z-score less than zero, less than $z=-0.25$, $z=-0.5$, $z=-0.75$, $z=-1$, or $z=-2$ (e.g., with a z-score of from about $-0.5$ or $-0.75$ to about $-1$ or about $-2$, or a z-score of from about $-0.75$ or $-1$ to about $-2$). In one embodiment, a patient is considered to have a low alpha power or a low aperiodic exponent value when the z-score is less than $-0.2$, $-0.25$, $-0.3$, $-0.35$, $-0.4$, $-0.45$, $-0.5$, $-0.55$, $-0.6$, $-0.65$, $-0.7$, $-0.75$, $-0.8$, $-0.85$, $-0.9$, $-0.95$, or $-1.0$. In another embodiment, a patient is considered to have a low alpha power or a low aperiodic exponent value when the z-score is less than $-1.2$, $-1.25$, $-1.3$, $-1.35$, $-1.4$, $-1.45$, $-1.5$, $-1.55$, $-1.6$, $-1.65$, $-1.7$, $-1.75$, $-1.8$, $-1.85$, $-1.9$, $-1.95$, or $-2.0$. In another embodiment, the subject may have a high gamma power above the $50^{th}$ percentile of a similar healthy subject with a z-score greater than zero, greater than $z=0.25$, $z=0.5$, $z=0.75$, $z=1$, or $z=2$ (e.g., with a z-score of from about 0.5 or 0.75 to about 1 or about 2, or a z-score of from about 0.75 or 1 to about 2). In one embodiment, a patient is considered to have a high gamma power when the z-score is greater than 0.2, 0.25, 0.3, 0.35, 0.4, 0.45, 0.5, 0.55, 0.6, 0.65, 0.7, 0.75, 0.8, 0.85, 0.9, 0.95, or 1.0. In another embodiment, a patient is considered to have a high gamma power when the z-score is greater than 1.2, 1.25, 1.3, 1.35, 1.4, 1.45, 1.5, 1.55, 1.6, 1.65, 1.7, 1.75, 1.8, 1.85, 1.9, 1.95, or 2.0.

Any reference to a standardized score herein can be calculated as a z-score, T-score, Standard Score, Scaled Score, Percentile rank, or Stanine score.

The terms "treat," "treatment," and "treating" in the context of the administration of a therapy to a patient refers to the reduction or inhibition of the progression and/or duration of a disease or condition, the reduction or amelioration of the severity of a disease or condition, and/or the amelioration of one or more symptoms thereof resulting from the administration of one or more therapies.

The term "administering" includes, but is not limited to, oral administration, administration as a suppository, topical contact, intravenous, transdermal, parenteral, intraperitoneal, intramuscular, intralesional, intrathecal, intranasal, rectal, percutaneous, or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. In embodiments, the administering does not include administration of any active agent other than the recited active agent. One preferred route of administration is the oral route.

An "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, delay, inhibition, suppression, or reduction of a symptom or symptoms of a disease or disorder, which could also be referred to as a "therapeutically effective amount." A "reduction" of a symptom or symptoms (and grammatical equivalents of this phrase) means decreasing of the severity or frequency of the symptom(s), or elimination of the symptom(s). An "effective amount" of a drug can be an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins). Dosages may be varied depending upon the requirements of the patient and the compound being employed. The dose administered to a patient, in the context of the present disclosure, should be sufficient to effect a beneficial therapeutic response in the patient over time. The size of the dose may also be determined by the existence, nature, and extent of any adverse side-effects. Determination of the proper dosage for a particular situation is within the skill of the practitioner.

To determine efficacy of treatment in psychiatric disorders (e.g., depression, major depression, bipolar depression, or post-traumatic stress disorder (PTSD)) questionnaires (e.g., self-reporting or clinician-administered questionnaires) may be used. Non-limiting examples of questionnaires useful for assessing treatment efficacy in psychiatric disorders (e.g., depression, major depression) include the Hamilton Rating Scale for Depression (HDRS); the Hamilton Rating Scale for Depression 17 item ($HDRS_{17}$ or HDRS-17); the 21 item HDRS ($HDRS_{21}$); the 24 item HDRS ($HDRS_{24}$); the Quick Inventory of Depressive Symptoms (QIDS); the Patient Health Questionnaire (PHQ-9); the Cognitive and Physical Functioning Questionnaire (CPFQ); the Mood and Symptom Questionnaire subscale scores for Anxious Arousal, Anhedonic Depression, and General Distress; the Montgomery-Asberg Depression Scale (MADRS); the Beck Depression Inventory; the Clinical Global Impressions (GCI) scale); and the Snaith-Hamilton Pleasure Scale (SHAPS). Questionnaires may be completed prior to, during, and following treatment, and changes in the scores may be used to determine treatment efficacy. In some embodiments, the $HDRS_{17}$ is used to determine treatment efficacy. In some embodiments, the HDRS is used to determine treatment efficacy. In some embodiments, the $HDRS_{21}$ is used to determine treatment efficacy. In embodiments, the $HDRS_{24}$ is used to determine treatment efficacy. In some embodiments, the QIDS is used to determine treatment efficacy. In some embodiments, the Mood and Symptom Questionnaire subscale scores for Anxious Arousal, Anhedonic Depression, and General Distress are used to determine treatment efficacy. In some embodiments, the MADRS is used to determine treatment efficacy. In embodiments, the Beck Depression Inventory is used to determine treatment efficacy. In some embodiments, the clinical global impression (CGI) scale is used to determine treatment efficacy. In some embodiments, treatment efficacy is determined by measuring (e.g., quantifying) a change in the $HDRS_6$, $MADRS_6$, or $HDRS_{17}$ score. In some embodiments, treatment efficacy is determined by measuring (e.g., quantifying) a change in the $HDRS_{21}$ score. In some embodiments, treatment efficacy is determined by measuring (e.g., quantifying) a change in the HDRS score. In some embodiments, treatment efficacy is determined by measuring (e.g., quantifying) a change in the $HDRS_{24}$ score. In some embodiments, treatment efficacy is determined by measuring (e.g., quantifying) a change in the QIDS score. In some embodiments, treatment efficacy is determined by measuring (e.g., quantifying) a change in the Mood and Symptom Questionnaire subscale scores for Anxious Arousal, Anhedonic Depression, and General Distress. In some embodiments, treatment efficacy is determined by measuring (e.g., quantifying) a change in the MADRS score. In embodiments, treatment efficacy is determined by measuring (e.g., quantifying) a change in the Beck Depression Inventory score. In some embodiments, treatment efficacy is determined by measuring (e.g., quantifying) a change in the CGI scale. A non-limiting example of a questionnaire useful for assessing treatment efficacy for PTSD is the Clinician-Administered PTSD Scale for DSM-5 (CAPS-5). In another embodiment, the questionnaire for assessing treatment efficacy of PTSD is the Clinician-Administered PTSD Scale for DSM-IV (CAPS-IV). In yet another embodiment, the questionnaire for assessing treatment efficacy of PTSD is a self-report, such as the PCL (PTSD Checklist) (e.g., the PTSD Checklist for DSM-5 (PCL-5)). In some embodiments, treatment efficacy is determined by measuring (e.g., quantifying) a score on a questionnaire as described herein during a baseline period prior to treatment to a score on a questionnaire as described herein reported 1, 2, 3, 4, 6, 8 or more weeks after commencing treatment or terminating treatment.

Treatment may result in a reduction of symptoms (e.g., a response) or in remission. In embodiments, a reduction in symptoms is referred to as a response. In embodiments, a response is a 50% or greater decrease in symptoms. A response (e.g., a 50% or greater decrease in symptoms) to treatment may be determined by measuring (e.g., quantifying) a change in a score as described herein, including embodiments thereof, on a questionnaire as described herein, including embodiments thereof. In embodiments, remission is a score of 7 or less at endpoint on the $HDRS_{17}$. In embodiments, remission is a score of 7 or less at endpoint on the HDRS. In embodiments, remission is a score of 10 or less on the $HDRS_{24}$. In embodiments, remission is a score of 5 or less on the QIDS. In embodiments, remission is a score of 10 or 9 or less on the MADRS. In embodiments, remission is a score of 4 or less on the PHQ9.

"Learning and/or memory" can be objectively assessed by one or more of the tests described herein, including the following tests: VM-REACT (Verbal memory recall computerized test), The Rey Auditory Verbal Learning Test, California Verbal Learning Test (including the CVLT-II and CVLT-3), California Verbal Learning Test—Short Form, California Verbal Learning Test—Children's Version, Hopkins Verbal Learning Test, Hopkins Verbal Learning Test—Revised, Philadelphia Verbal Learning Test, International Shopping List Test, Verbal section of the Repeatable Battery for the Assessment of Neuropsychological Status, Cerad Neuropsychological Assessment Battery Word List Task, Children's Auditory Verbal Learning Test, Children's Memory Scale, Bay Area Verbal Learning Test, Cogstate battery (which can include the following subtests: Behavioral Pattern Separation Object Test, Continuous Paired Associate Learning Test, Face Name Associative Memory Exam, Groton Maze Learning Test and its Delayed Recall and Delayed Reverse Recall versions, International Shopping List, One Card Learning Test), CANTAB (which can include the following subtests: Delayed Matching to Sample, Pattern Recognition Memory, Verbal Paired Associates, Paired Associates Learning, Verbal Recognition Memory), Penn Computerized Neurocognitive Battery (which can include the following subtests: Penn Word Memory Task, Penn Face Memory Task, Visual Object Learning Test), the NIH Toolbox and its subtests (Face Name Associative Memory Exam Test, Picture Sequence Memory Test, and Rey Auditory Verbal Learning Test), Neuropsychological Assessment Battery Memory Module (which can include the following subtests and their delayed recall and recognition components: List Learning, Shape Learning, Story Learning, and Daily Living Memory), WHO/UCLA Auditory Verbal Learning Test, Repeatable Battery for the Assessment of Neuropsychological Status (which includes the following subtests and their delayed recall and recognition components: List Learning, Story Memory, and Figure Recall), Wide Range Assessment of Memory and Learning (which includes the following subtests and their delayed recall and recognition components: Picture Memory, Design Learning, Story Memory, and Verbal Learning), Buschke Selective Reminding Test, Wechsler Memory Scale (which includes the following subtests and their delayed recall and recognition components: Logical Memory, Verbal Paired Associates, Designs, and Visual Reproduction), Woodcock-Johnson Long Term Retrieval factor (which includes the following subtests and their delayed recall and recognition components: Story Recall and Visual-Auditory Learning), Test of Memory and Learning (which includes the following subtests and their delayed recall and recognition components: Memory for Stories, Facial Memory, Word Selective Reminding, Visual Selective Reminding, Abstract Visual Memory, Object Recall, Visual Sequential Memory, Paired Recall, and Memory for Location), NEPSY (which includes the following subtests and their delayed recall and recognition components: List Memory, Memory for Designs, Memory for Faces, Memory for Names, Narrative Memory, Sentence Repetition, and Word List Interference), Brief Visuospatial Memory Test—Revised, Benton Visual Retention Test, Rey Osterreith Complex Figure Test, and any combination of any of the foregoing. The VM-REACT (Verbal Memory REcAll Computerized Test) is described in Naparstek et al., *J Psychiatr Res.*, 2019, 114:170-177 (PMID 31096177), which is hereby incorporated by reference. In one embodiment, the learning and/or memory ability of a patient is objectively assessed by the VM-REACT (Verbal memory recall computerized test).

Memory is often assessed by a recall index. The term "recall index" refers to a measure of accuracy of immediate and/or delayed recall of the learned material. For example, immediately after learning, recall can be assessed, and again after a delay (e.g., 20 minutes). Alternatively, only one of these conditions may be used to assess recall. Similarly, an irrelevant distractor learning trial may be given to further separate the learning whose memory is being assessed from the assessment of the memory per se. The recall index therefore encompasses one or more assessments of recall after learning has occurred.

The term "impaired learning and/or memory" refers to a subject having learning and/or memory, as measured by one or more tests, below that of the $50^{th}$ percentile, or a lower cutoff, of healthy subjects of similar demographics, such as based on similarity in age to patients (i.e., z-score<0). The z-score is an example of a standardized score that can be used to characterize subjects as "impaired". The z-score reflects a transformation of learning and/or memory performance relative to a healthy subject distribution, which may account for factors such as age, education and gender in that transformation. A z score below zero indicates performance for that subject that is below the $50^{th}$ percentile of similar healthy subjects, while a z score above zero indicates performance that is above the $50^{th}$ percentile of similar healthy subjects. For example, the subject may have a learning and/or memory score below the $50^{th}$ percentile of a similar healthy subject with a z-score less than zero, less than z=−0.25, z=−0.5, z=−0.75, z=−1, or z=−2 (e.g., with a z-score of from about −0.5 or −0.75 to about −1 or about −2, or a z-score of from about −0.75 or −1 to about −2). In one embodiment, a patient is considered to have impaired learning and/or memory when the z-score is less than −0.2, −0.25, −0.3, −0.35, −0.4, −0.45, −0.5, −0.55, −0.6, −0.65, −0.7, −0.75, −0.8, −0.85, −0.9, −0.95, or −1.0. In another embodiment, a patient is considered to have impaired learning and/or memory when the z-score is less than −1.2, −1.25, −1.3, −1.35, −1.4, −1.45, −1.5, −1.55, −1.6, −1.65, −1.7, −1.75, −1.8, −1.85, −1.9, −1.95, or −2.0. In one embodiment, impaired learning and/or memory is assessed (partly or wholly) based on recall index.

In one embodiment, a patient (such as one having major depressive disorder, a major depressive episode, bipolar depression, or post-traumatic stress disorder) is considered to have impaired learning and/or memory when the z-score as determined by VM-REACT is less than −0.5. In another embodiment, a patient (such as one having major depressive disorder, a major depressive episode, bipolar depression, or post-traumatic stress disorder) is considered to have impaired learning and/or memory when the z-score as determined by VM-REACT is less than −0.30. In yet another embodiment, a patient (such as one having major depressive disorder, a major depressive episode, bipolar depression, or post-traumatic stress disorder) is considered to have impaired learning and/or memory when the z-score as determined by VM-REACT is less than −0.35. In yet another embodiment, a patient (such as one having major depressive disorder, a major depressive episode, bipolar depression, or post-traumatic stress disorder) is considered to have impaired learning and/or memory when the z-score as determined by VM-REACT is less than −0.40. In yet another embodiment, a patient (such as one having major depressive disorder, a major depressive episode, bipolar depression, or post-traumatic stress disorder) is considered to have impaired learning and/or memory when the z-score as determined by VM-REACT is less than −0.45. In yet another embodiment, a patient (such as one having major depressive disorder, a major depressive episode, bipolar depression, or post-traumatic stress disorder) is considered to have impaired learning and/or memory when the z-score as determined by VM-REACT is less than −0.55. In yet another embodiment, a patient (such as one having major depressive disorder, a major depressive episode, bipolar depression, or post-traumatic stress disorder) is considered to have impaired learning and/or memory when the z-score as determined by VM-REACT is less than −0.60. In yet another embodiment, a patient (such as one having major depressive disorder, a major depressive episode, bipolar depression, or post-traumatic stress disorder) is considered to have impaired learning and/or memory when the z-score as determined by VM-REACT is less than −0.65. In yet another embodiment, a patient (such as one having major depressive disorder, a major depressive episode, bipolar depression, or post-traumatic stress disorder) is considered to have impaired learning and/or memory when the z-score as determined by VM-REACT is less than −0.70. In yet another embodiment, a patient (such as one having major depressive disorder, a major depressive episode, bipolar depression, or post-traumatic stress disorder) is considered to have impaired learning and/or memory when the z-score as determined by VM-REACT is less than −0.75.

The term "poor cognition" (or "cognitively poor"), unless otherwise defined, refers to a subject having cognitive function, as measured by one or more tests of cognitive function, below that of the $50^{th}$ percentile of healthy subjects of similar demographics, such as age (z-score<0). Z scores reflect a transformation of cognitive task performance relative to a healthy subject distribution, which may account for factors such as age, education and gender in that transformation. A z score below zero indicates performance for that subject that is below the $50^{th}$ percentile of similar healthy subjects, while a z score above zero indicates performance that is above the $50^{th}$ percentile of similar healthy subjects. For example, the subject may have a cognitive score below the $50^{th}$ percentile of a similar healthy subject with a z-score less than zero, less than $z=-0.25$, $z=-0.30$, $z=-0.35$, $z=-0.40$, $z=-0.45$, $z=-0.5$, $z=-0.75$, $z=-1$, or $z=-2$ (e.g., with a z-score of from about −0.5 or −0.75 to about −1 or about −2, or a z-score of from about −0.75 or −1 to about −2).

Cognition can be assessed by methods known in the art, including those described in DSM-5 (see, e.g., pages 593-595). For instance, cognition can be measured by a simple reaction time test, choice reaction time test, one back working memory task, visual learning task, learning and/or memory (such as verbal learning and/or memory), or any combination of any of the foregoing. In one embodiment, learning and/or memory is assessed. In one embodiment, the cognitive ability of a subject is measured with a Cogstate Brief Battery as described in Maruff et al., *Arch Clin Neuropsychol.* 2009, 24(2): 165-78, which is hereby incorporated by reference. Tests of cognition (such as to assess information processing speed, working memory, learning, and attention) include, but are not limited to, Digit symbol substitution task, Oddball task, Flanker task, Wisconsin card sort task, Trail making task, Corsi Block task, Digit Span task, Reverse Digit Span task, Verbal Learning and/or memory task, and Verbal Fluency task. Reduced information processing speed, slow decision making or difficulty making decisions may be diagnosed by tests that assess reaction times or performance under speed-based task instructions (e.g., reduced number of correct symbols in a digit symbol substitution task or reduced verbal fluency in a fixed amount of allotted time), such as those described in J. DeLuca and J. H. Kalmar, *Information Processing Speed in Clinical Populations*, Taylor & Francis Group (2008), which is hereby incorporated by reference. Decision making (including slow decision making and difficulty making decisions) can be assessed by the performance of tasks that assess the process of deciding in the face of competing alternatives (e.g., simulated gambling) (DSM-5, p. 593). Reductions in attention can be assessed by: (1) for sustained attention: maintenance of attention over time (e.g., pressing a button every time a tone is heard, and over a period of time), (2) for selective attention: maintenance of attention despite competing stimuli and/or distractors: hearing numbers and letters read and asked to count only letters, and (3) for divided attention: attending to two tasks within the same time period: rapidly tapping while learning a story being read. Processing speed can be quantified on any task by timing it (e.g., time to put together a design of blocks; time to match symbols with numbers; speed in responding, such as counting speed or serial 3 speed).

Reductions in working memory can be assessed by the ability to hold information for a brief period and to manipulate it (e.g., adding up a list of numbers, repeating a series of numbers or words backward or repeating a sequence of actions).

Reductions in memory can also be assessed by the following methods (in addition to the working memory assessment method described above):

(1) Immediate memory span: Ability to repeat a list of words, digits or sequence of actions.

(2) Learning and retention: Assesses the process of encoding new information (e.g., word lists (with the word list having the potential to also be repeated multiple times), a short story, or diagrams). Reduced acquisition and retention of new information may be diagnosed by tests that assess learning and memory (e.g., learning a list of words or symbols over a series of trials and recalling them following a 15- to 30-minute delay; learning a brief story or complex figure and recalling them following a 20- to 30-minute delay), such as those described in E. Strauss, E. M. S. Sherman, and O. Spreen (2006), A compendium of neuropsychological tests: Administration, norms, and commentary. (3rd Edition). Oxford University Press, New York, New York, which is hereby incorporated by reference. The aspects of recent memory that can be tested include 1) free recall (e.g. the person is asked to recall as many words, diagrams, or elements of a story as possible); 2) cued recall (e.g. semantic cues such as "List all the food items on the list" or "Name all of the children from the story" are provided to the subject); 3) recognition memory (e.g., "Was 'apple' on the list?" or "Did you see this diagram or figure?"); and 4) recall of an original list of items or words after presentation of a distractor list of items or words. It can also be assessed as a combination of different aspects of recent memory; for example, recall of an original list of items or words following a distractor list and free recall, such as those described in R. J. Ivnik, J. F. Malec, E. G. Tangalos, R. C. Petersen, E. Kokmen, and L. T. Kurland (1992), Mayo's Older Americans Normative Studies: Updated AVLT norms for ages 56 to 97, *The Clinical Neuropsychologist* 6, 83-104. Other aspects of memory that can be assessed include semantic memory (memory for facts), autobiographical and episodic memory (memory for personal events or people), and implicit (procedural) learning (unconscious learning of skills).

The term "slow cognition", unless otherwise defined, refers to a subject having slow cognitive function (longer time to respond), as measured by one or more tests of information processing speed (such as a simple reaction time test or choice reaction time test), below the $50^{th}$ percentile, or another cutoff, of a healthy subject of similar age (e.g., z-score<0).

Processing speed can be quantified on any task by timing it (e.g., time to put together a design of blocks; time to match symbols with numbers; speed in responding, such as counting speed or serial 3 speed).

Reduced learning and/or memory can be assessed by the methods described above for immediate memory span and learning and retention.

Reduced executive function can be assessed by tests that evaluate flexibility of thinking (e.g., alternating between numbers and letters in sequential order), abstract/conceptual reasoning and problem-solving (e.g., completing complex puzzles), planning (e.g., completing mazes), organization (e.g., categorizing a list of words based on semantic cues), working memory (e.g., holding and manipulating information held in one's mind), creativity, generativity, and initiation (e.g., spontaneously producing words that begin with a specific letter), impulse control and inhibition (e.g., purposefully suppressing automatic responses to test stimuli), and self-monitoring (e.g., checking answers to ensure accuracy), such as those described in E. Strauss, E. M. S. Sherman, and O. Spreen (2006), G. A. Gioia, P. K. Isquith, S. C. Guy, and L. Kenworthy (2015), Behavior Rating Inventory of Executive Function®, Second Edition (BRIEF®2). Lutz, FL: PAR Inc.; and Delis, D. C., Kaplan, E., & Kramer, J. H. (2001), Delis-Kaplan Executive Function System (D-KEFS), The Psychological Corporation, San Antonio, TX. Gioia G. A., Isquith P. K., Guy S. C., Kenworthy L. (2015).

In one embodiment, the cognitive impairment, poor or slow cognition or difficulty making decisions is due, at least in part, to reduced attention, memory, learning, working memory, or any combination of any of the foregoing.

As used herein, the terms "subject," "participant," and "patient" are used interchangeably and refer to a human patient unless indicated otherwise.

Suitable antidepressants for concurrent therapy include, but are not limited to, (i) serotonin and norepinephrine reuptake inhibitors (SNRIs) (such as venlafaxine, duloxetine, milnacipran, sibutramine, SEP-227162, or LY 2216684), (ii) selective serotonin reuptake inhibitors (SSRIs) (such as escitalopram, fluoxetine, fluvoxamine, sertraline, citalopram, vilazodone, and paroxetine), (iii) atypical antidepressants (such as agomelatine, mianserin, mirtazapine, nefazodone, opipramol, tianeptine, and trazodone), and (iv) norepinephrine and dopamine reuptake inhibitors (NDRIs) (such as bupropion, aminaptine, prolintane, dexmethylphenidate, and pipradrol). In one embodiment, the antidepressant is selected from SSRIs, SNRIs, mirtazapine, bupropion, or any combination of any of the foregoing. In another embodiment, the antidepressant is not a monoamine oxidase inhibitor (MAOI), a tricyclic antidepressant (TCA) (such as amitriptyline, imipramine, clomipramine, and desipramine), or ketamine.

Suitable mood stabilizers include, but are not limited to, lithium carbonate, divalproex sodium, valproic acid, valproate semisodium, sodium valproate, tiagabine, levetiracetam, lamotrigine, gabapentin, carbamazepine, oxcarbazepine, topiramate, zonisamide, aripiprazole, risperidone, olanzapine, quetiapine, asenapine, paliperidone, ziprasidone, lurasidone, lumateperone, cariprazine, verapamil, clonidine, propranolol, mexiletine, guanfacine and omega-3 fatty acids.

In certain embodiments of any of the methods described herein, the impairment in learning and/or memory is measured using one or more of the following learning and/or memory tests:

VM-REACT
Rey Auditory Verbal Learning Test
California Verbal Learning Test (including the CVLT-II and CVLT-3)
California Verbal Learning Test-Short Form
California Verbal Learning Test-Children's Version
Hopkins Verbal Learning Test-Revised
Neuropsychological Assessment Battery Memory Module, which includes the following subtests and their delayed recall and recognition components:
List Learning
Shape Learning
Story Learning
Daily Living Memory
WHO/UCLA Auditory Verbal Learning Test
Philadelphia Verbal Learning Test
Cerad Neuropsychological Assessment Battery Word List Task
Children's Auditory Verbal Learning Test
Children's Memory Scale
Bay Area Verbal Learning Test
International Shopping List Task
Cogstate Battery, which includes the following subtests and their delayed recall and recognition components:
Behavioral Pattern Separation Object Test
Continuous Paired Associate Learning Test
Face Name Associative Memory Exam Groton Maze Learning Test
International Shopping List
One Card Learning Test
CANTAB battery, which includes the following subtests and their delayed recall and
recognition components:
Delayed Matching to Sample
Pattern Recognition Memory
Verbal Paired Associates
Paired Associates Learning
Verbal Recognition Memory
Penn Computerized Neurocognitive Battery, which includes the following subtests and their
delayed recall and recognition components:
Penn Word Memory Task
Penn Face Memory Task
Visual Object Learning Test
NIH Toolbox, which includes the following subtests and their delayed recall and recognition
components:
Face Name Associative Memory Exam Test
Picture Sequence Memory Test
Rey Auditory Verbal Learning Test
Repeatable Battery for the Assessment of Neuropsychological Status, which includes the
following subtests and their delayed recall and recognition components:
List Learning
Story Memory
Figure Recall
Wide Range Assessment of Memory and Learning, which includes the following subtests
and their delayed recall and recognition components:
Picture Memory
Design Learning
Story Memory
Verbal Learning
Buschke Selective Reminding Test
Wechsler Memory Scale, which includes the following subtests and their delayed recall and
recognition components:
Logical Memory
Verbal Paired Associates
Designs
Visual Reproduction
Woodcock-Johnson Long Term Retrieval factor, which includes the following subtests and
their delayed recall and recognition components:
Story Recall
Visual-Auditory Learning
Test of Memory and Learning, which includes the following subtests and their delayed recall
and recognition components:
Memory for Stories
Facial Memory
Word Selective Reminding
Visual Selective Reminding
Abstract Visual Memory
Object Recall
Visual Sequential Memory
Paired Recall
Memory for Location
NEPSY, which includes the following subtests and their delayed recall and recognition
components:
List Memory
Memory for Designs
Memory for Faces
Memory for Names
Narrative Memory
Sentence Repetition
Word List Interference
Brief Visuospatial Memory Test-Revised
Benton Visual Retention Test
Rey Osterreith Complex Figure Test The term "advertising" refers to notifying, informing, and/or apprising one or more individuals of information (e.g., the efficacy of a pharmaceutical product containing (4-benzylpiperazin-1-yl)-[2-(3-methylbutylamino)pyridin-3-yl]methanone or a pharmaceutically acceptable salt thereof in the treatment of major depressive disorder, post-traumatic stress disorder, or one or more symptoms thereof in patients having impaired learning and/or memory), such as by mass media, including, but not limited to, newspaper, magazine, and internet advertisements, television commercials, and billboard signs. The term "advertising" as used herein also includes including a statement that a pharmaceutical product containing (4-benzylpiperazin-1-yl)-[2-(3-methylbutylamino)pyridin-3-yl]methanone or a pharmaceutically acceptable salt thereof can treat major depressive disorder, post-traumatic stress disorder, or one or more symptoms thereof in patients having impaired learning and/or memory in the labeling for the pharmaceutical product.

The term "marketing" refers to the act or process of selling a product (e.g., a pharmaceutical product containing (4-benzylpiperazin-1-yl)-[2-(3-methylbutylamino)pyridin-3-yl]methanone or a pharmaceutically acceptable salt thereof (e.g., its phosphate salt)), including, but not limited to, any offer for sale or sale of a product, as well as advertising. The marketing may be directed to, for example, doctors (such as psychiatrists or general practitioners) treating human subjects suffering from major depressive disorder, post-traumatic stress disorder, or one or more symptoms thereof. The marketing step may comprise the step of including a statement in the labelling for a pharmaceutical product containing (4-benzylpiperazin-1-yl)-[2-(3-methylbutylamino)pyridin-3-yl]methanone or a pharmaceutically acceptable salt thereof (e.g., its phosphate salt) can effectively treat major depressive disorder, post-traumatic stress disorder, or one or more symptoms thereof in a patient having impaired learning and/or memory.

In any of the methods described herein, the (4-benzylpiperazin-1-yl)-[2-(3-methylbutylamino)pyridin-3-yl]methanone or a pharmaceutically acceptable salt thereof (e.g., (4-benzylpiperazin-1-yl)-[2-(3-methylbutylamino)pyridin-3-yl]methanone phosphate) may be incorporated into a pharmaceutical product. The pharmaceutical product may be a therapeutic package which comprises (a) one or more dosage forms (e.g., tablets) of (4-benzylpiperazin-1-yl)-[2-(3-methylbutylamino)pyridin-3-yl]methanone or a pharmaceutically acceptable salt thereof (e.g., (4-benzylpiperazin-1-yl)-[2-(3-methylbutylamino)pyridin-3-yl]methanone phosphate), (b) a container that contains one or more of the dosage forms, and (c) written matter such as labelling directing the use of the dosage forms in the treatment of major depressive disorder, post-traumatic stress disorder, or one or more symptoms thereof in patients having impaired learning and/or memory.

The term "pharmaceutical product" refers to any pharmaceutical product containing (4-benzylpiperazin-1-yl)-[2-(3-methylbutylamino)pyridin-3-yl]methanone or a pharmaceutically acceptable salt thereof, such as (4-benzylpiperazin-1-yl)-[2-(3-methylbutylamino)pyridin-3-yl]methanone phosphate. The pharmaceutical product may contain one or dosage forms (e.g., tablets) of (4-benzylpiperazin-1-yl)-[2-(3-methylbutylamino)pyridin-3-yl]methanone or a pharmaceutically acceptable salt thereof (e.g., (4-benzylpiperazin-1-yl)-[2-(3-methylbutylamino)pyridin-3-yl]methanone phosphate).

Example 1—Phase 2 Clinical Trial With NSI-189

A retrospective analysis of the 220-patient phase 2 study of NSI-189 discussed above was performed (11). In the study, patients having major depressive disorder were randomized to receive a total daily dose of 40 mg or 80 mg of NSI-189 or placebo in stage 1 (first 6 weeks) of the clinical trial design. Patients receiving placebo and who failed to respond to placebo were then re-randomized to 40 mg, 80 mg or placebo in stage 2 (second 6 weeks) of the trial. The remaining patients continued their treatment for stage 2 of the trial. Treatment in either stage was given for six weeks. Patients were eligible for study participation if they were between the ages of 18-60 years, with current major depressive disorder of at least 8 weeks duration according to the DSM-5, as diagnosed by the Structured Clinical Interview for the DSM-5 clinical trial version (SCID-5-CT) during the screen and remote assessment visits, and if they were scored at least 20 at screen, remote assessment, and baseline visits on the Montgomery-Asberg Depression Rating Scale (MADRS). The phase 2 study collected cognitive task performance data prior to treatment, and then again after both stage 1 and stage 2 of the treatment protocol. The purpose of doing so was to determine whether treatment with this compound results in improvement in cognitive functioning, as measured by a variety of behavioral measures.

Prior to the inventor's retrospective analysis, there was no consideration as to using behavioral measures to predict treatment outcome nor was there any analysis conducted to this effect. There was no consideration of using cognitive performance as a predictor but only as an outcome measure. The analyses described herein focus on the four cognitive task measures included in the Cogstate battery, as these data are available as z-scores wherein each individual's performance was normalized to that in a large healthy population. The tasks in this battery included a simple reaction time (RT) task, a choice RT task, a one-back working memory task, and a visual learning task. Moreover, given the conversion to z-score, a composite cognitive task performance score could be computed by averaging the z-scores for each of the four tasks in the battery. Analyses focused on the MADRS primary outcome of the study. Statistical analyses focused on the complete trial (incorporating both stage 1 and stage 2 outcomes), using the SPCD analytic approach reported in the original study and thus aligned could be compared with the original statistical analysis plan. Mixed models repeated measures (MMRM) were used to predict change from baseline (at 2, 4, and 6 weeks) in clinical scores and included covariates for group (i.e., poor versus good cognition as defined by a given measure of interest), time, time x group, time x baseline MADRS and baseline MADRS. These covariates likewise were used in the original study, and thus results here can be compared with the all-comer results reported previously. Statistical significance was thus assessed on the primary outcome (MADRS change from baseline at 6 weeks across the SPCD design). The change in MADRS scores in the all comer (i.e. original sample) analysis is shown in FIG. 1(A) for comparison to subgroups as defined by cognitive task performance.

To examine the effect of baseline cognition on clinical outcomes, individuals were split at the mean of the average z-score across all tasks (thus a cognition composite score). This generates two groupings, which were termed poor cognition (below mean, negative z scores) or good cognition (above mean, positive z scores). The poor cognition group can also be termed to be cognitively impaired. The composite score mean at which the cut-off between good and poor cognition groups was performed was at z=−0.32, which corresponded to the median of this patient group (and by a negative z score, denoted that being below the median for a matched healthy population). Notably, this mean is in line with expectations of moderately-impaired cognitive task performance in depression in general (12, 13).

Surprisingly, it was found that while the original all-comer analysis failed to find statistical significance on the primary MADRS outcome, a robust and statistically significant effect was found for the 80 mg arm versus placebo on change in MADRS scores in the poor cognition group using the cognitive composite score (SPCD analysis p=0.014; FIG. 1B). This corresponds to a drug-placebo effect size of Cohen's d=0.58, which is approximately double the typical d~0.3 effect size of standard-of-care antidepressants in all-comer populations (31). Comparison of the 80 mg arm versus placebo in stage 1 of the trial also found statistical significance at week 2 (d=0.55, p=0.045), week 4 (d=0.7, p=0.01) and week 6 (d=0.59, p=0.03) with response being greater for 80 mg than placebo. Though the 40 mg group was visually intermediate in outcome to the 80 mg and placebo group, this effect was not significant (p=0.39; FIG. 1(B)). By contrast, no significant differences were found between either drug arm and placebo in the good cognition group (p=0.25, FIG. 1C). Thus, not only does cognitive task performance successfully differentially predict outcome between drug and placebo, this appears to be substantially stronger for the 80 mg treatment relative to 40 mg, which runs counter to expectations from prior treatment main effect analyses of the data as discussed above (11). This is also surprising since poor cognition was previously reported to be consistently predictive of poor response to SSRIs and SNRIs in multiple studies of depressed patients. Groves et al., *Front. Psychiatry* 9:382, 2018; Etkin et al., *Neuropsychopharmacology* 40(6): 1332-1342, 2015.

Figure 2:
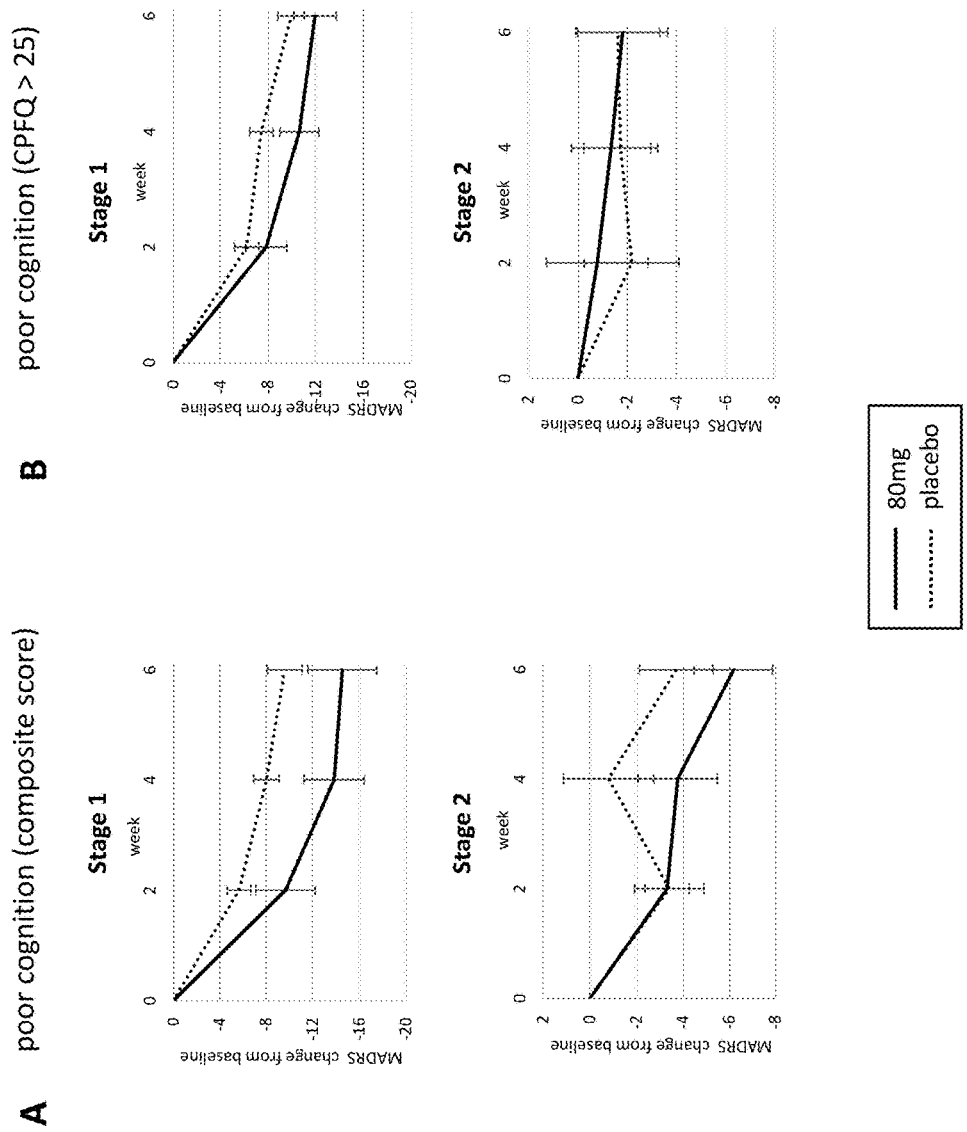
FIG. 2 has graphs showing the change in MADRS depression scores in Example 1 from baseline during stage 1 and stage 2 in (A) cognitively impaired patients as defined by the cognitive composite score being below the patient mean and (B) cognitively impaired patients as defined by a CPFQ score>25 receiving placebo or 80 mg NSI-189.

Whether poor cognition could be defined in an alternative manner was tested, namely by asking patients to rate their cognition on a self-report questionnaire. One such questionnaire is the Cognitive and Physical Functioning Questionnaire (CPFQ)(15). This scale is notable as it was featured in analyses for the antidepressant vortioxetine in its approval by both the FDA and the European Medicines Agency (EMA). In those analyses, poor subjective cognition was defined as a CPFQ score of >25, and thus whether cognitive impairment based on the CPFQ could identify individuals who preferentially benefit from treatment with 80 mg of NSI-189 was examined. As shown in FIG. 2, which contrasts poor cognition defined using the composite cognitive task performance score (as shown earlier) with that defined by the CPFQ, no difference is seen between treatment arms in patients with poor self-reported cognition. The difference between the 80 mg and placebo groups in CPFQ-defined poor cognition was comparable to that in the all-comer population. Thus, surprisingly, not only is poor objective cognition a predictor of better drug response, but this impairment must be measured through performance of cognitive tasks such as those used here. The objective measurement cannot be replaced by use of patient-reported assessment of their own cognitive symptoms. This furthermore did not depend on the cutoff used on the CPFQ to define poor cognition patients as multiple other cutoffs were used to define poor subjective cognition on the CPFQ and none were predictive of drug response.

While data from this Phase 2 trial demonstrated that patients with poor cognition respond better to NSI-189 than those with good cognition, the clinical sample was uninformative as to whether NSI-189 is more effective in poor cognition patients who had an insufficient response to a standard-of-care antidepressant. This is because only 18% of the patients receiving 80 mg of NSI-189 had an insufficient response to an adequate trial of an antidepressant according to the Antidepressant Treatment Response Questionnaire (ATRQ) in this Phase 2 sample.

Example 2—Phase 2 Clinical Trial With NSI-189 as Monotherapy or Adjunctive Treatment in Depression To determine whether poor cognition is a predictor of better response to 80 mg NSI-189 in both patients who were not receiving any other antidepressant treatments and patients who had an insufficient response to standard-of-care antidepressants, a large open-label Phase 2 clinical trial was conducted in which patients with MDD and/or PTSD were given 80 mg NSI-189 (as 40 mg BID) for up to 8 weeks. These patients also underwent a more comprehensive cognitive battery than in the prior Phase 2 study. As above, MMRM analyses were applied on MADRS change from baseline scores in MDD patients. This analysis included 90 patients, of whom 37 were receiving NSI-189 as monotherapy (i.e. no other concurrent antidepressant) and 53 were receiving it adjunctive to a standard-of-care antidepressant to which they had an insufficient response. The dose of the antidepressant (i.e. apart from NSI-189), if one was present at baseline, did not change during the trial. Of the overall sample, 61 had an insufficient response to at least one adequate trial of an antidepressant within the current episode, which included all patients receiving adjunctive NSI-189 as well as some receiving it as monotherapy. In this study, the current episode was determined by the either the prior two years, or the period within the prior two years since the last time at which two continuous months of euthymia occurred, whichever was shorter. Insufficient response to an antidepressant in the current episode was defined as less than a 50% reduction in symptoms (e.g., based on the total score on the MADRS or HDRS).

The overall sample using MMRMs that included core terms for time, baseline, group (i.e. poor versus good cognition as defined by a given measure of interest), time x group and time by baseline, as well as additional covariates for monotherapy/adjunctive use, time x monotherapy/adjunctive and time x group x monotherapy/adjunctive were first analyzed in order to control for the effects of NSI-189 treatment context within the overall analysis. All analyses used a z=−0.75 cutoff to identify poor cognition patients (with z-scores determined with reference to a separate healthy population) in order to ensure that poor cognition patients are impaired in those tasks. Approximately 40% of the MDD population in this study had cognition scores below the −0.75 cutoff, meaning that the poor cognition subpopulation makes up a significant and meaningful segment of the overall depression population. Moreover, as further detailed below, the relationship between degree of cognitive impairment (i.e. lower z-score) and better clinical outcome (i.e. greater MADRS change from baseline) is a continuous one, thereby supporting multiple cut-points to define poor cognition below z=0 (i.e., healthy mean score matched to patients' age and gender).

Figure 3:
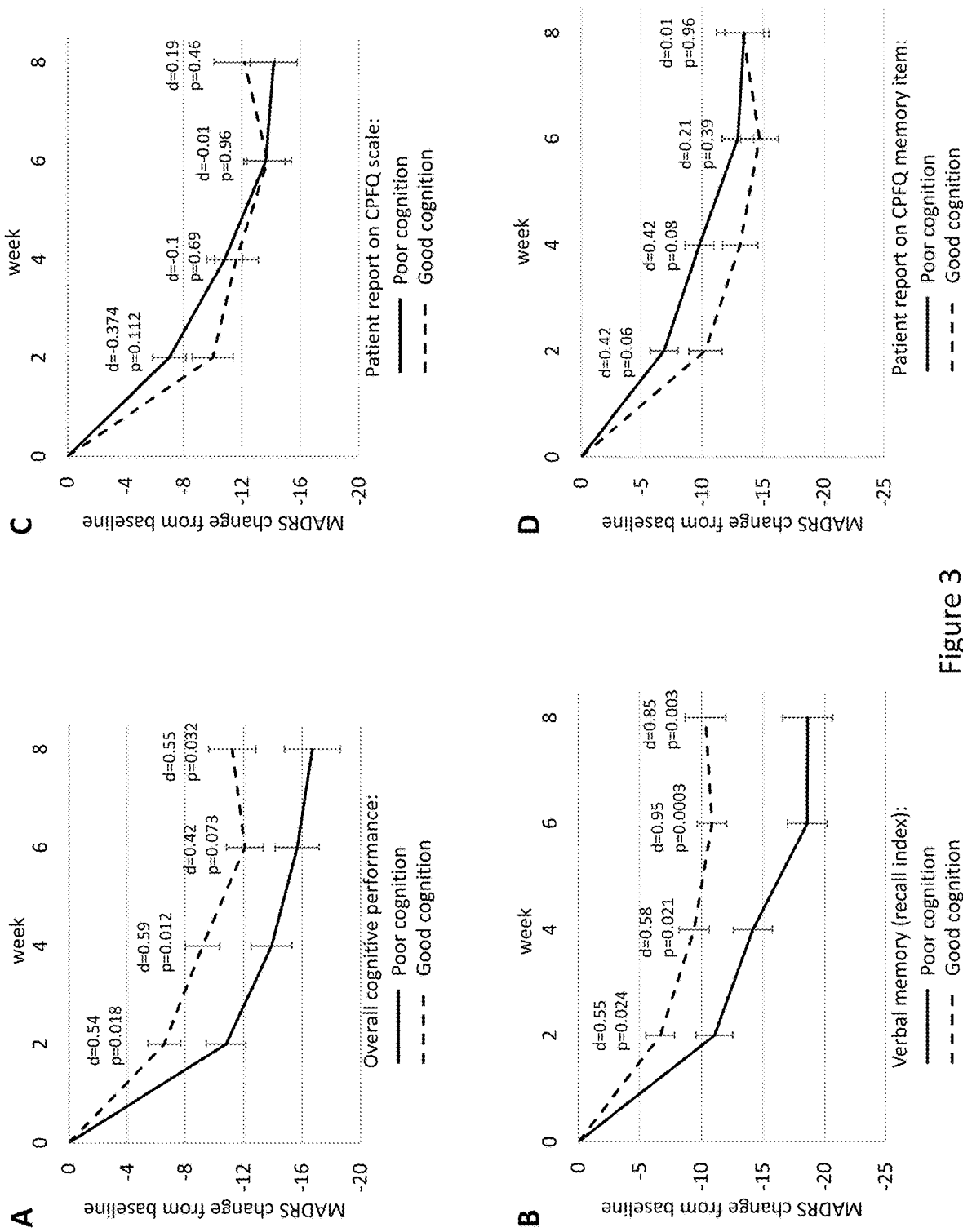
FIG. 3 has graphs showing the change in MADRS scores in Example 2 from baseline in (A) poor cognition patients as defined by the cognitive composite score of z≤−0.75 relative to good cognition patients (z>−0.75), (B) poor cognition patients as defined by poor memory recall of learned word lists (verbal memory recall index) scores of z≤-0.75 relative to good cognition patients (z>-0.75), (C) subjective poor cognition patients as defined by CPFQ scores>25 relative to good cognition patients (score≤25), and (D) subjective poor memory recall as defined by one item within the CPFQ scale (poor is moderate or greater diminishment, and good is minimal or less diminishment). Analyses control for monotherapy versus adjunctive use of NSI-189. Cohen's d's and p-values are shown on the graph.

An overall cognitive performance variable comprised of measures of executive function (digit-symbol substitution task, Wisconsin card sorting task, trail making task, Corsi blocks, verbal fluency), information processing speed (flanker task, choice RT, simple RT) and verbal learning and/or memory was analyzed. As seen in FIG. 3(A), poor cognition patients had a significantly better improvement in depressive symptoms (reduction in the MADRS score) to treatment with NSI-189, further supporting the findings from the re-analysis of the prior Phase 2 trial where a general measure of poor cognition that encompassed executive function, processing speed and learning was used.

The ability of poor cognition to predict better outcome on depressive symptoms was most strongly carried by verbal learning and/or memory. Learning and/or memory was assessed with a word list task, in which patients are given the word lists on five learning trials, and then memory is assessed through recall of those word lists immediately after learning and again after an approximately 20 minute delay (including after inclusion of a new distractor list of words). This computer-implemented task is named VM-REACT (Verbal memory recall computerized test) and is further described in Naparstek et al., *J Psychiatr Res.*, 2019, 114: 170-177 (PMID 31096177). Poor recall of these word lists predicted significantly better outcome for MDD. This is seen in FIG. 3(B), where recall was quantified using the recall index, which averages both immediate and delayed recall in the verbal learning and/or memory task into a single memory recall measure. Additionally, poor immediate recall predicted significantly better outcome for MDD at weeks six and eight (Cohen's d=0.48, p=0.022; Cohen's d=0.56, p=0.010, respectively), and poor delayed recall predicted significantly better outcome for MDD at weeks two (Cohen's d=0.43, p=0.028), four (Cohen's d=0.40, p=0.045), six (Cohen's d=0.67, p=0.001) and eight (Cohen's d=0.61, p=0.004). Moreover, much as was found in the re-analysis of the prior Phase 2 study, patient reported cognitive impairment (as assessed on the CPFQ scale) did not predict outcome. Using the same definition of poor cognition as above (i.e. CPFQ>25), there were no significant differences between patients with self-reported poor versus good cognition (FIG. 3(C)). Likewise, taking just the memory recall item from the CPFQ, which is the subjective patient-reported measure most analogous to the recall index measure in FIG. 3(B), moderate or greater subjective diminishment of memory recall was not predictive of outcome with NSI-189 (FIG. 3(D)). Thus, it is critical to directly assess cognition using standardized behavioral tasks.

Prediction of NSI-189 outcome by poor cognition, as defined by recall index, separately for patients receiving the drug as monotherapy, as an adjunct to an antidepressant to which they had an insufficient response, or as a function of whether they have had an insufficient response to an antidepressant in the current episode (regardless of monotherapy or adjunctive use of NSI-189) was analyzed. As shown in FIG. 4A and 4B, there was a similar magnitude and statistically significantly greater response to NSI-189 in poor cognition relative to good cognition patients in both the monotherapy and adjunctive treatment contexts. Thus, poor cognition predicts better depression symptom outcome with NSI-189 as adjunctive treatment in depression much as it does with NSI-189 as monotherapy—a conclusion not able to be drawn based on the prior Phase 2 study, which did not include adjunctive treatment. Likewise, patients were examined who had an insufficient response to at least one standard-of-care antidepressant treatment in the current depressive episode, a population that was too small in the prior Phase 2 study to be able to draw any conclusions from. As shown in FIG. 4C, poor cognition also predicted significantly better response to 80 mg NSI-189 in these patients. Thus, this new Phase 2 trial extended upon the prior Phase 2 trial by revealing novel evidence that NSI-189 is more effective for poor cognition patients that had an insufficient response to an antidepressant treatment in the current episode and either receive NSI-189 as monotherapy or adjunctively to that antidepressant. Additionally, this new trial extended upon the prior Phase 2 trial by showing that poor verbal memory recall as a measure of poor cognition (which was not previously assessed) is powerfully predictive of better response to NSI-189 regardless of whether the drug is used as a monotherapy or adjunctively to an antidepressant.

Figure 4:
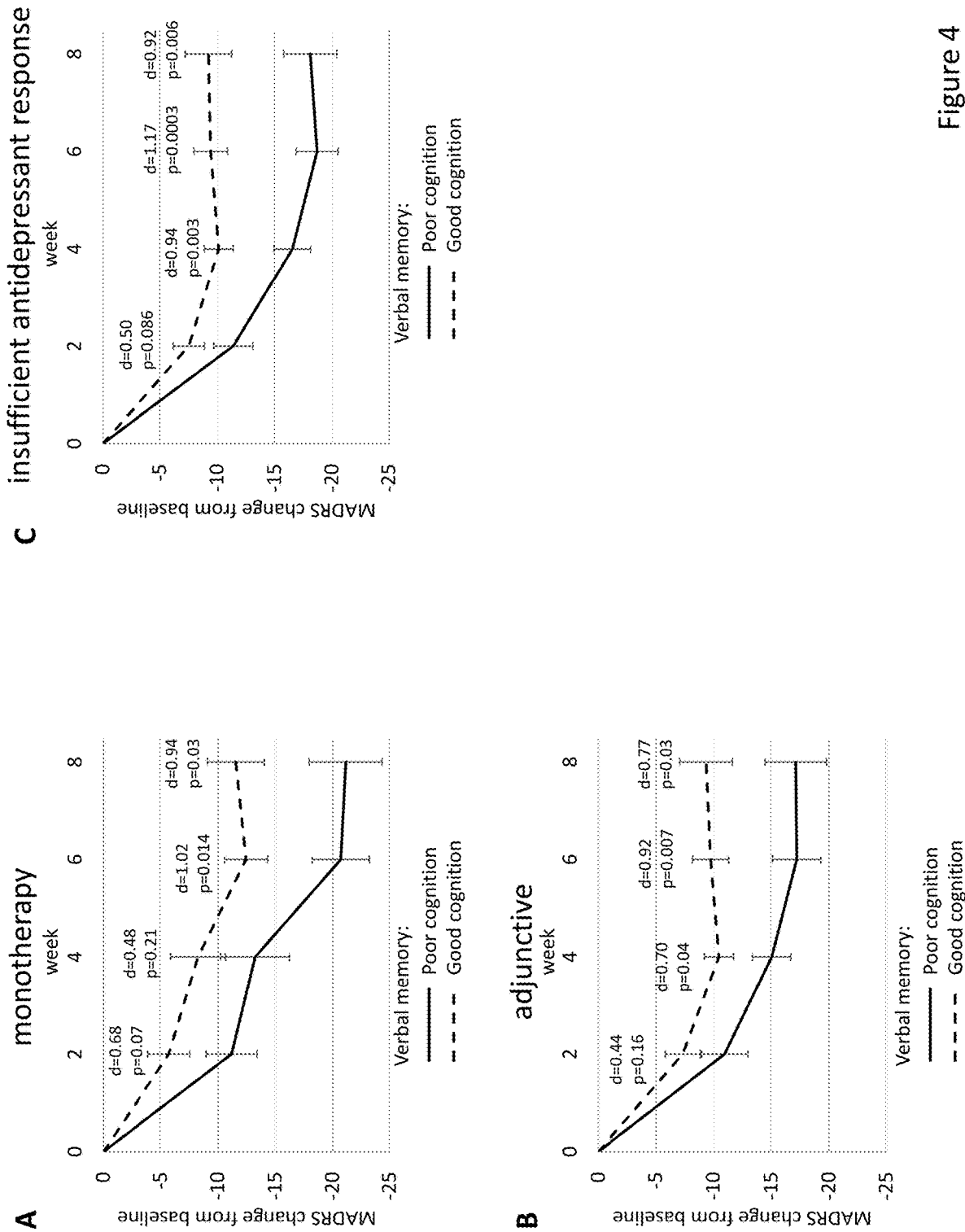
FIG. 4 has graphs showing the change in MADRS scores in Example 2 from baseline within the group receiving NSI-189 (A) as a monotherapy, (B) as an adjunctive therapy, or (C) who had an insufficient response to at least one antidepressant and are getting NSI-189 as monotherapy or adjunctively, comparing poor cognition patients as defined by poor learning and memory (low recall index) scores of z≤-0.75 to good cognition patients (z>-0.75). Cohen's d's and p-values are shown on the graph.
Figure 5:
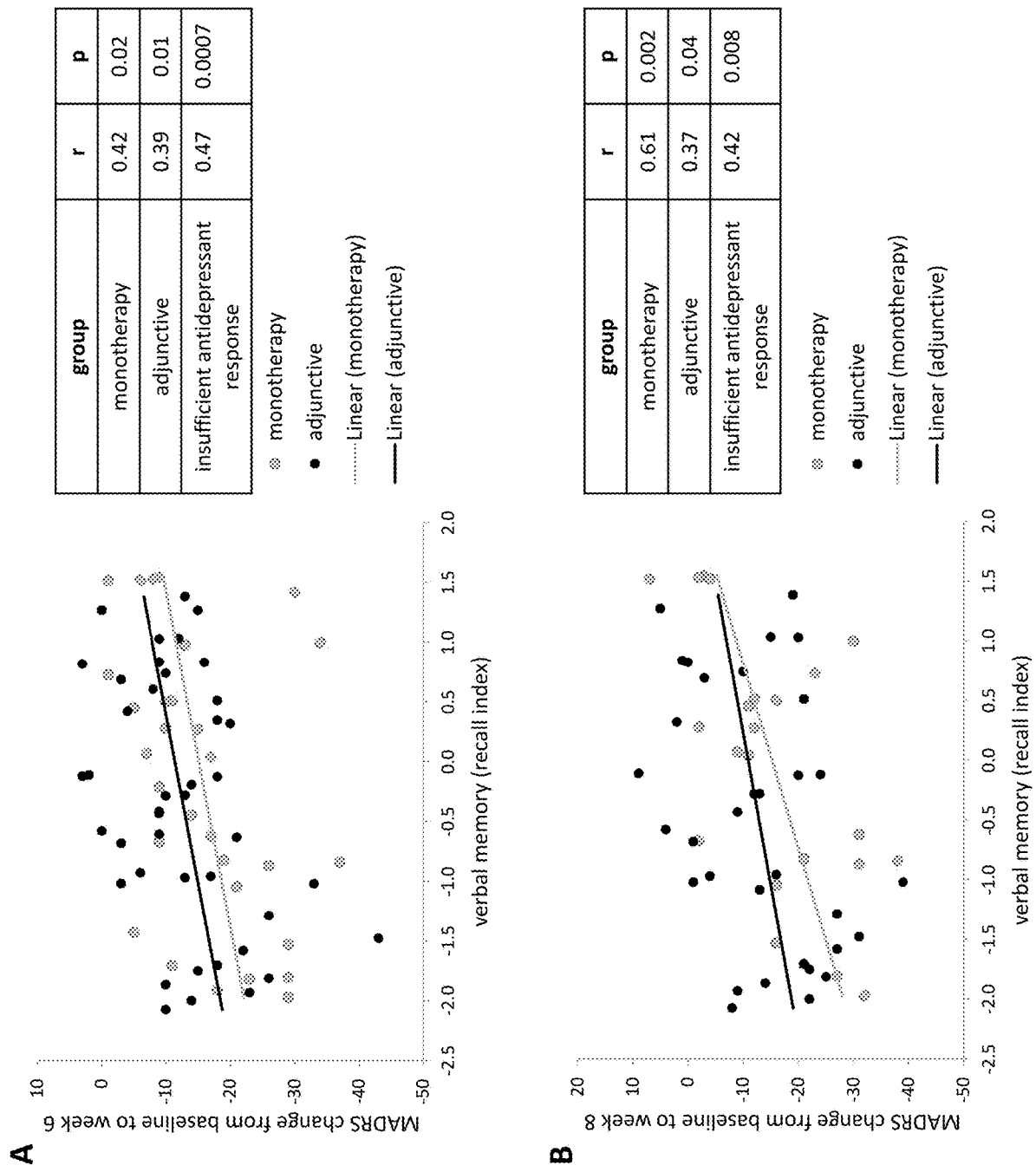
FIG. 5 has graphs showing a correlation between change in MADRS scores in Example 2 from baseline to (A) week 6 or (B) week 8 and learning and memory (recall index), showing a continuous relationship between the degree of cognitive impairment (more negative z scores) and the degree of treatment response (more negative change scores). Also shown are correlation coefficients (r) and p-values for correlations between learning and memory (low recall index) and MADRS change within the NSI-189 monotherapy group, the NSI-189 adjunctive therapy group and within a group of patients who had an insufficient response to at least one antidepressant and are getting NSI-189 as monotherapy or adjunctively.
Figure 6:
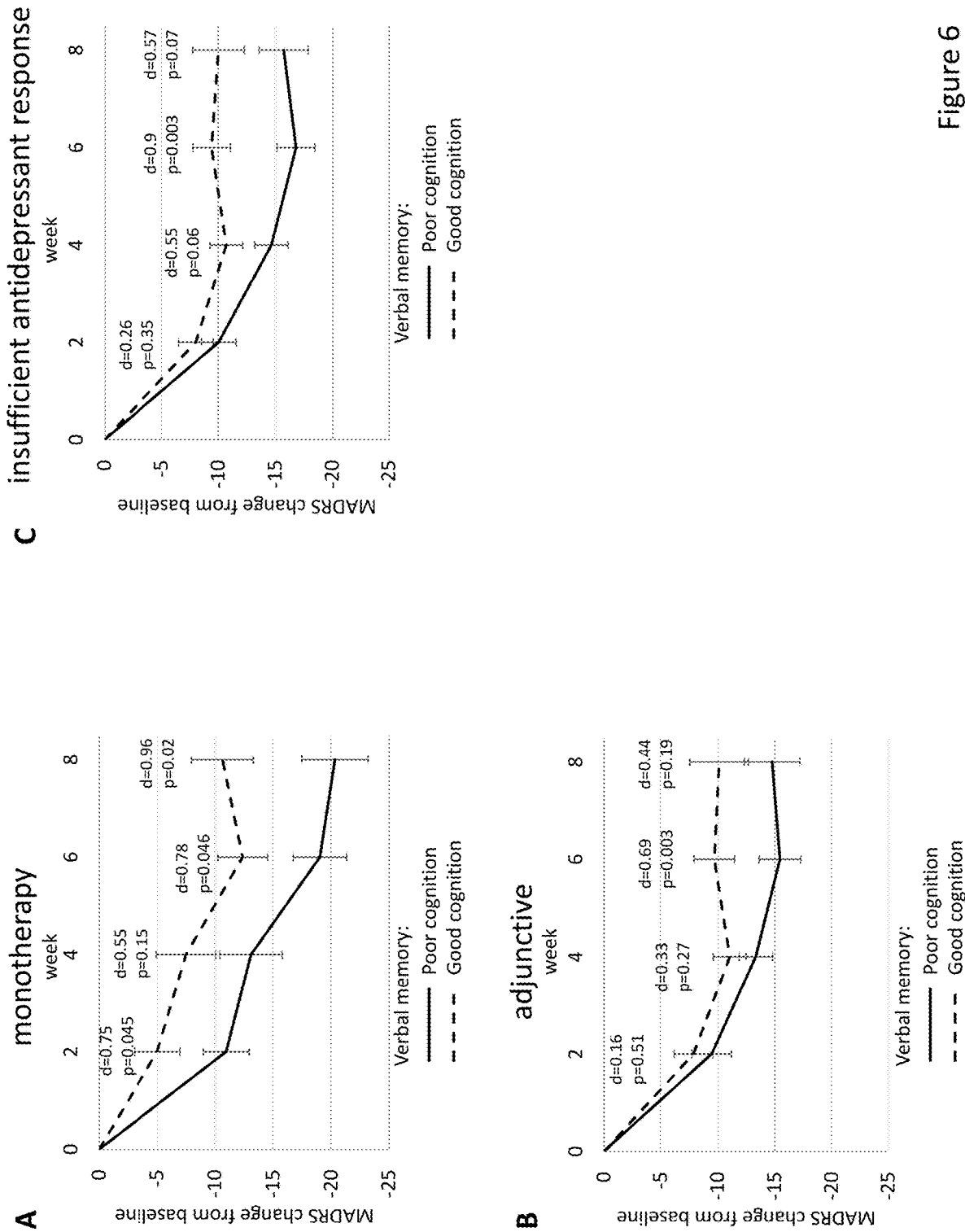
FIG. 6 has graphs showing the change in MADRS scores in Example 2 from baseline within the group receiving NSI-189 (A) as a monotherapy, (B) as an adjunctive therapy, or (C) who had an insufficient response to at least one antidepressant and are getting NSI-189 as monotherapy or adjunctively, comparing poor cognition patients as defined by learning and memory (low recall index) scores of z≤-0.418 to good cognition patients (z>-0.418). Cohen's d's and p-values are shown on the graph.

Moreover, though a cutoff of $z=-0.75$ was used to define poor cognition patients in the analyses above, the relationship between degree of cognitive impairment and degree of better depression treatment response is a continuous one. This is seen in correlations between change in MADRS scores from baseline to week 6 (FIG. 5(A)) or week 8 (FIG. 5(B)) and baseline learning and/or memory (recall index). As can be seen, there are significant correlations for each of these time points and each of the subpopulations examined (monotherapy, adjunctive, one or more insufficient treatment trials). Thus, poor cognition can be defined by any z-score on a cognitive metric below 0, which indicates the mean of a matched healthy population. The lower the z-score cutoff, the greater the expected NSI-189 clinical response of the thusly defined poor cognition patients. To illustrate this, in FIG. 6 the inventors show results similar to those in FIG. 4 whereby poor verbal memory predicts better outcome with NSI-189, however in FIG. 6 a cutoff of $z=-0.418$ is used instead of $z=-0.75$. The $z=-0.418$ cutoff corresponds to the median scores for patients in this study. As in FIG. 4, FIG. 6(A) shows patients receiving NSI-189 as monotherapy, FIG. 6(B) shows patients receiving NSI-189 adjunctively to an antidepressant to which they have had an insufficient response, and FIG. 6(C) shows patients receiving NSI-189 who had an insufficient response to an antidepressant in the current episode (which they may be still taking the antidepressant adjunctively or not).

Though the analyses above have focused on using poor learning and/or memory to define poor cognition patients, doing so defines patients with impairments across a broad range of cognitive and behavioral measures. As seen in FIG. 7, poor cognition patients as defined by poor learning and/or memory (recall index) are impaired relative to good cognition patients in a wide variety of cognitive tasks, including: verbal fluency (number of words generated in response to a cue), working memory on a Corsi Block test (maximum number of sequenced actions correctly replicated in a row after watching a sequence performed), executive function and information processing speed on a digit-symbol substitution task (number of correct conversion of symbols to matched digits based on a given symbol-digit mapping), executive function and information processing speed on a flanker task (congruent reaction time), information processing speed on choice or simple reaction time tasks, information processing speed on the trails A task (completion time), interference resolution on a flanker task or trails B task (reaction time and completion time, respectively), and accuracy of emotion recognition in a face emotion recognition task (accuracy overall as well as for angry, fearful or happy expressions). Learning and/or memory, however, has been found to be a better predictor of depression treatment response with NSI-189 than these other objective cognitive measures.

Figure 8:
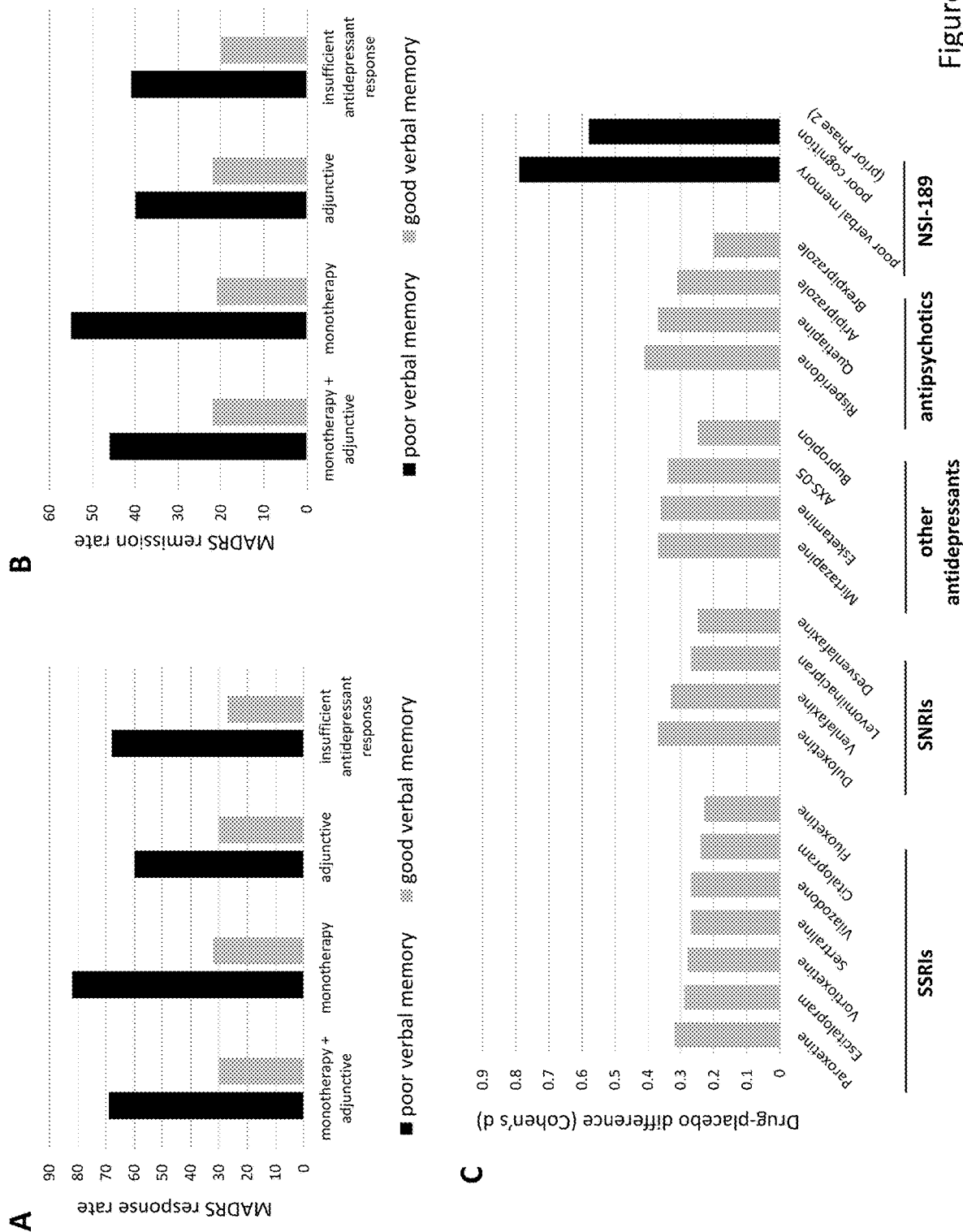
FIG. 8 has graphs of (A) response rates and (B) remission rates on the MADRS (defined as a 50% or greater reduction in symptoms from baseline to week 6) in poor versus good learning and memory (recall index) patients for various definitions of the clinical population in Example 2.

To further understand the clinical significance of the cognitive prediction of antidepressant outcome, plotted are response (FIG. 8(A)) and remission (FIG. 8(B)) rates amongst patients as a function of poor versus good learning and/or memory. As seen, response and remission rates are in poor learning and/or memory patients were consistently approximately double those of good learning and/or memory patients, regardless of how the clinical population was defined (i.e., overall depression, monotherapy, adjunctive, or one or more insufficient antidepressant treatment responses in the current episode). As an absolute level of response, the 60-82% response rates in poor learning and/or memory patients are strikingly higher than typical placebo response rates (~35% for monotherapy and ~20% for adjunctive therapy) (31-32), even considering the open label nature of this study. When considered from the context of ultimate clinical care, where a drug would be given in an open-label fashion, such high response rates serve as a contrast to current antidepressants where only one third to half of patients response to treatment (33-34).

The inventors next sought to understand the contrast between response to NSI-189 in poor cognition/poor learning and/or memory patients, and the typical response to antidepressants or antipsychotics when used adjunctively to an antidepressant that had yielded an insufficient treatment response. To do so, the presumed drug-placebo difference for these patients was calculated based on two pieces of data: 1) the known all-comer drug placebo difference from the prior Phase 2 study (Cohen's d~0.2), to which was added 2)

the enrichment observed in the second Phase 2 study between the poor learning and/or memory subpopulation relative to the overall depression population (expressed as Cohen's d). Shown in FIG. 8(C) is the calculated drug-placebo Cohen's d for poor learning and memory patients in the second Phase 2 study (d=0.79), as well as the Cohen's d found in poor cognition patients in the prior Phase 2 study when averaging Stage 1 and Stage 2 responses (d=0.58). These striking effects of the drug could be contrasted to the effect sizes derived from a wide variety of antidepressants and antipsychotics (used adjunctively) (31-32 and 35-38), which were typically roughly half of the magnitude of the response to NSI-189. These results demonstrate the striking clinical significance of the identification of poor cognition as a predictor of better response to NSI-189 in depression. Moreover, poor cognition has been shown to predict worse response to placebo, creating the possibility that in poor cognition patients (39), this estimated drug-placebo difference could be even larger if the placebo response is further reduced in poor relative to good cognition patients. Likewise, poor cognition predicts poor response to standard-of-care antidepressants (e.g. SSRIs and SNRIs) (40), creating a striking contrast with NSI-189 to which response is greater in patients with poor cognition.

Figure 9:
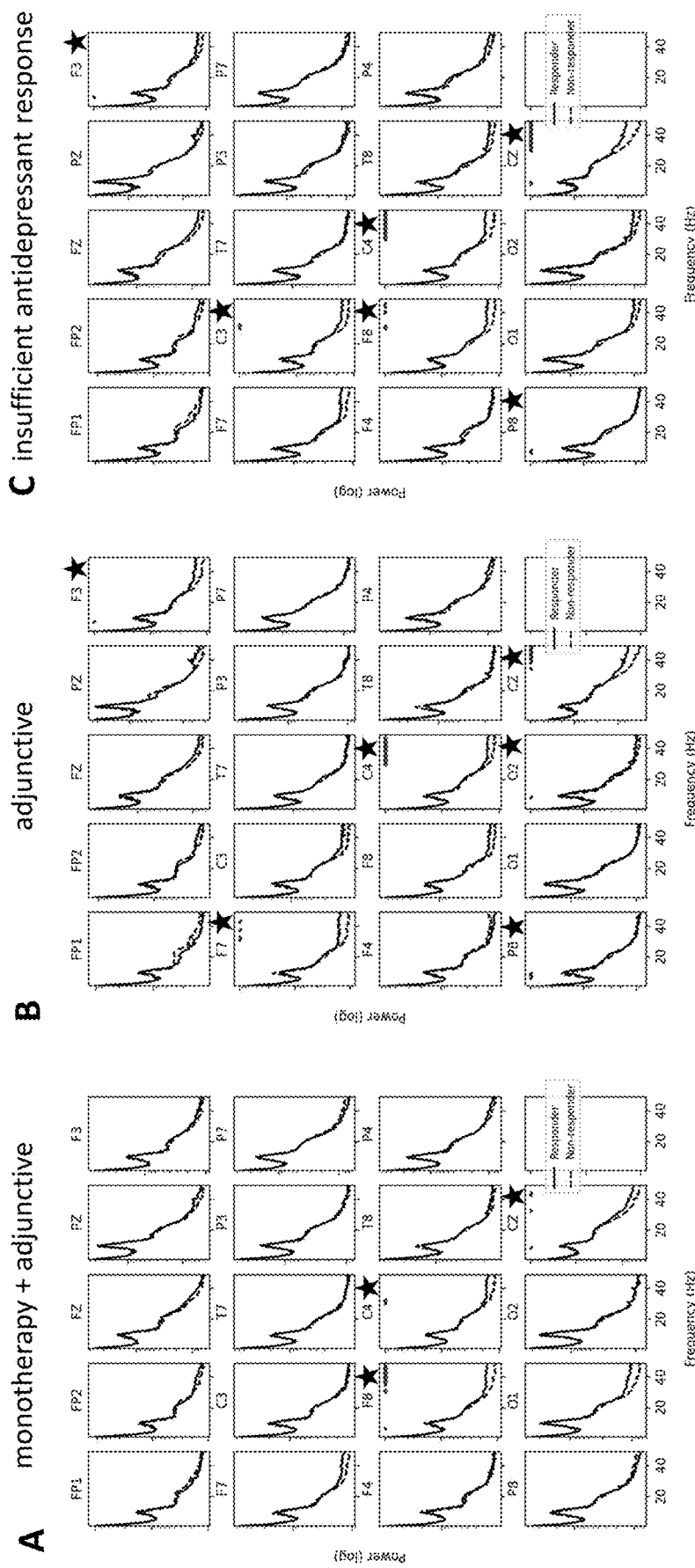
FIG. 9 has sets of graphs of EEG resting eyes closed power spectrum density plots in Example 2 comparing EEG power at different frequencies in responders (50% or greater decrease in MADRS scores from baseline) to non-responders to (A) NSI-189 (both monotherapy and adjunctive therapy), (B) who had received the drug adjunctively to an antidepressant to which they had an insufficient response, or (C) who had an insufficient response to an antidepressant in the current episode (and are getting NSI-189 as monotherapy or adjunctively to that antidepressant). Stars indicate channels with significant differences between groups (denoted as dots or lines in the upper part of each channel's panel for the corresponding frequency).

Next tested was whether signal derived from resting state electroencephalography (EEG) could predict treatment outcome with NSI-189. The power spectral density (PSD) distribution of the EEG data was examined. A schematic showing the EEG power spectral density is provided in FIGS. 1A and 1B in A. T. Hill et al., Dev. Cogn. Neurosci. 54:101076, 2022. As seen in FIG. 9(A) herein, PSDs at multiple channels indicate that depression symptom responders to NSI-189 have significantly higher power in the high beta frequency range (20-30 Hz) and low gamma range (31-50 Hz) (calculated over central electrodes). Additionally, responders have lower power in the alpha frequency range (8-12 Hz). The same pattern is seen in patients receiving adjunctive NSI-189 (FIG. 9(B)) and patients who have had an insufficient response to at least one antidepressant (FIG. 9(C)). This EEG pattern suggests that higher brain excitability (particularly the difference in power in the low gamma range) predicts better response to NSI-189.

Figure 10:
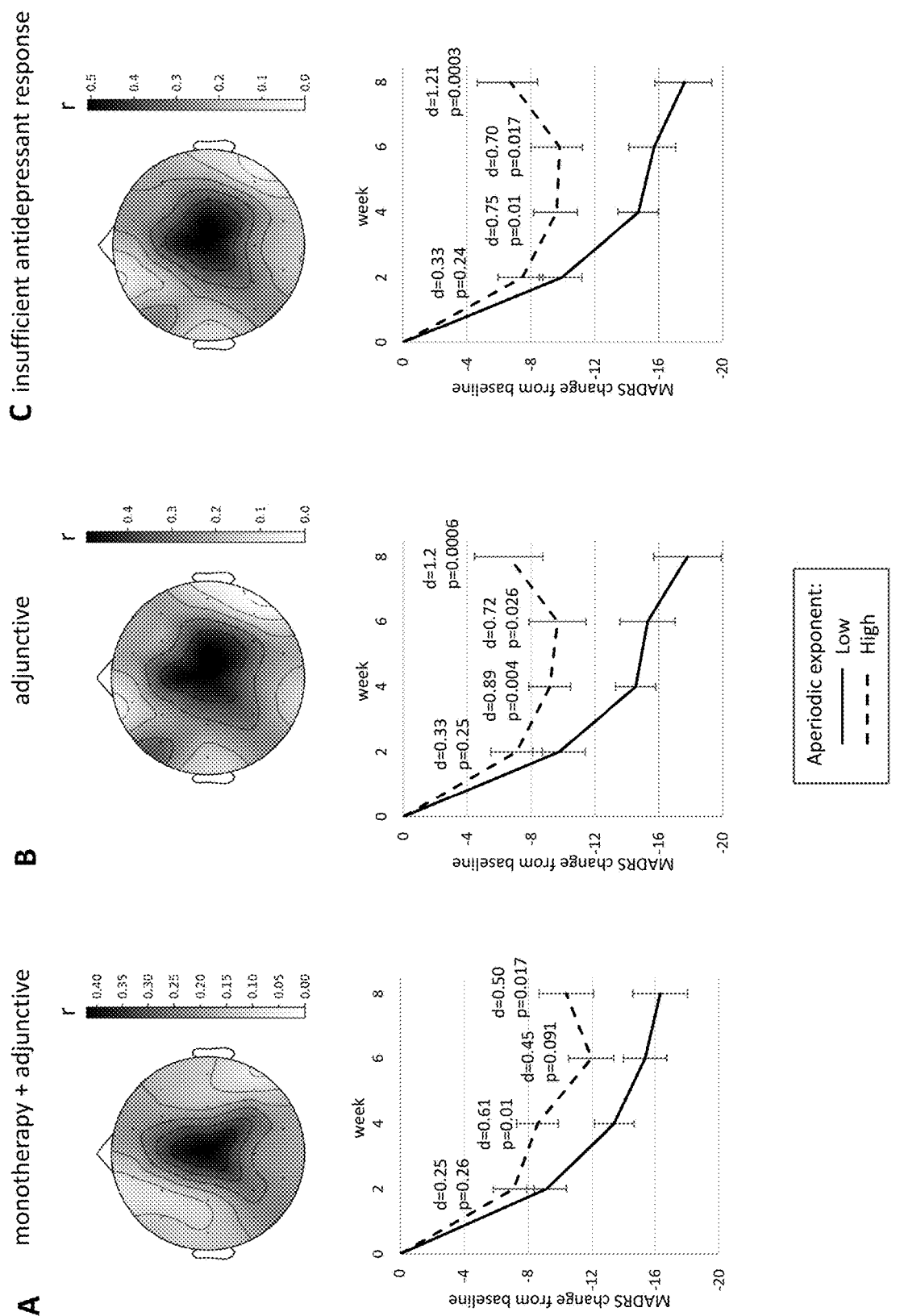
FIG. 10 has graphs showing the change in MADRS scores in Example 2 from baseline in patients receiving NSI-189 (A) as a monotherapy or adjunctive therapy, (B) adjunctively to an antidepressant to which they had an insufficient treatment response, or (C) who have had an insufficient response to an antidepressant in the current episode (regardless of whether they are receiving NSI-189 as monotherapy or adjunctively to that antidepressant), with a low aperiodic exponent (below the patient median value) versus those with a high aperiodic exponent. Analyses control for monotherapy versus adjunctive use of NSI-189. Cohen's d's and p-values are shown on the graph. The top-panel is an EEG topography plot of the channel-wise correlation between EEG resting eyes closed aperiodic exponent and percentage change from baseline in MADRS scores (a more positive correlation indicating better outcome for patients with smaller aperiodic exponents).

Another way of analyzing the PSD is through the observation that the background trend in the data can be quantified as a measure of background neural activity and has a 1/f relationship (where f is frequency). One way of quantifying this signal is termed the aperiodic exponent, which is estimated as the negative slope for the line of best fit over the 1-50 Hz range of the power spectral density in the log-log space (T. Donoghue, et al., Nat Neurosci, 23(12): 1655-1665 December 2020). Channel-wise correlation of the aperiodic exponent with treatment outcome (as percentage change in MADRS scores from baseline) was examined. FIG. 10(A) (top panel) shows that a positive correlation whereby lower aperiodic exponent (i.e. flatter PSDs) (calculated over the central electrodes) predicts better depression treatment outcome (more negative percent MADRS change from baseline). This relationship was particularly strong for central-parietal electrode locations. The bottom panel shows an MMRM analysis splitting the patient population at the median and examining prediction of change in MADRS from baseline, demonstrating significantly better depression outcome in low aperiodic exponent patients relative to high aperiodic exponent patients. Similar relationships were seen between lower aperiodic exponent and better depression treatment outcome in patients receiving adjunctive NSI-189 (FIG. 10(B)), as well as in patients who had an insufficient response to an antidepressant in the current episode (FIG. 10(C)).

Figure 11:
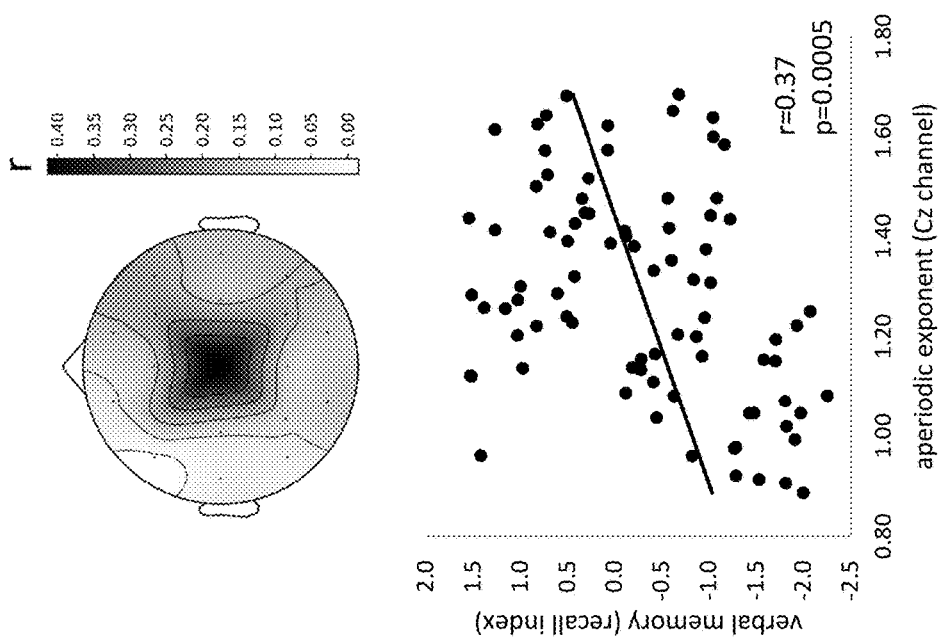
FIG. 11 shows the correlation between aperiodic exponent values and learning and memory performance (using recall index scores) in Example 2. The top-panel is an EEG topography plot of the channel-wise correlation between EEG resting eyes closed aperiodic exponent and recall index scores. A more positive correlation between aperiodic exponent values and learning and memory (recall index) indicates worse learning and/or memory for patients with smaller aperiodic exponents.

To understand the relationship between these EEG signals and memory recall index, either the channel-wise aperiodic exponent or power in the low gamma range were correlated with patients' recall index scores. As seen in FIG. 11, a larger aperiodic index (more steep power declines with higher frequencies in the PSD) was significantly correlated with greater recall index (better learning and/or memory). This is consistent with the findings above whereby better treatment outcome with NSI-189 is predicted by either a lower aperiodic exponent (more flat PSDs) and lower recall index scores, but furthermore relates the EEG and learning and/or memory signals to each other.

In summary, the findings from this Phase 2 study demonstrate that patients with either poor cognition (as measured by poor learning and memory recall) and/or greater brain excitability (as measured by lower aperiodic exponent or greater power in the low gamma range) have better depression treatment response to NSI-189, whether they received NSI-189 as a monotherapy, as an adjunct to an antidepressant to which they had an insufficient response, or in patients that have had an insufficient response in the current episode to an antidepressant drug regardless of whether NSI-189 is taken as a monotherapy or adjunctive to an antidepressant.

Example 3—Phase 2 Clinical Trial With NSI-189 in PTSD

To determine whether poor cognition is a predictor of better response to 80 mg NSI-189 in PTSD, the inventors next examined data from patients with PTSD from the open-label Phase 2 clinical trial above in Example 2. These patients underwent the same cognitive battery as patients with depression. As above, MMRM analyses were applied on the Clinician Administered PTSD Scale for DSM-5 (CAPS-5) change from baseline scores in PTSD patients. This analysis included 84 patients. All patients received 40 mg NSI-189 BID, as the depressed patients had above.

Figure 12:
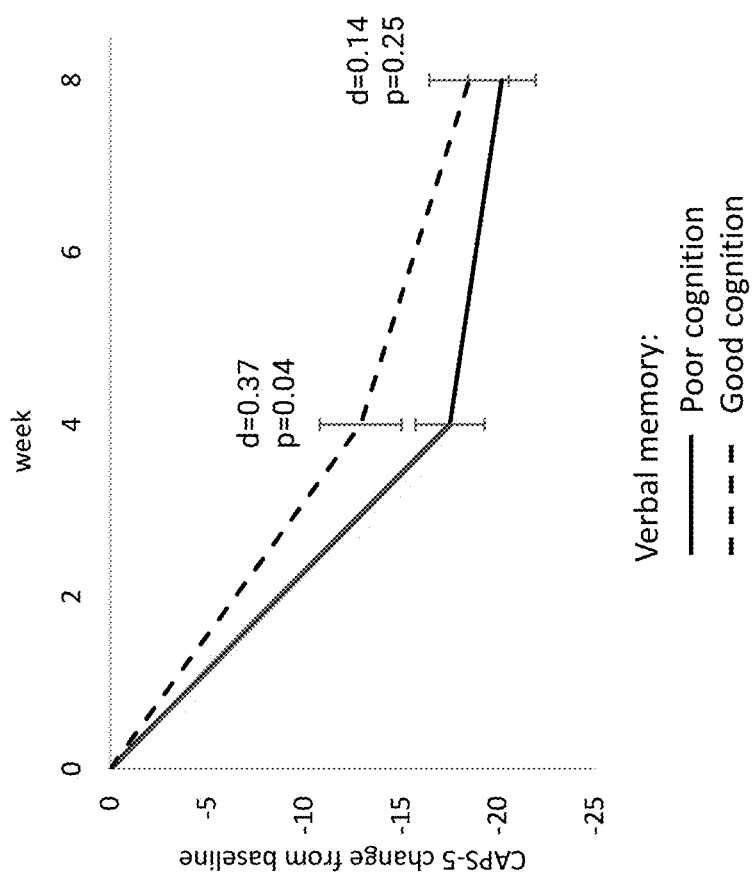
FIG. 12 is a graph showing the change in CAPS-5 scores in PTSD patients from Example 3 from baseline in poor cognition patients as defined by a recall index score of z≤-0.5 relative to good cognition patients (z>-0.5).

The overall sample using MMRMs that included core terms for time, baseline, group (i.e., poor versus good cognition as defined by a given measure of interest), time x group and time by baseline. The analyses shown in FIG. 12 used a z≤−0.5 cutoff on recall index scores in order to identify poor cognition patients (with z-scores determined with reference to a separate healthy population identically as for the depressed patients above). This cutoff ensured that poor cognition patients are impaired in this task. As seen in FIG. 12, a significant difference in outcome was observed at week 4, wherein patients with poor cognition had a significantly greater reduction in PTSD symptoms than those with good cognition.

Example 4—Clinical Trial With NSI-189

Figure 13:
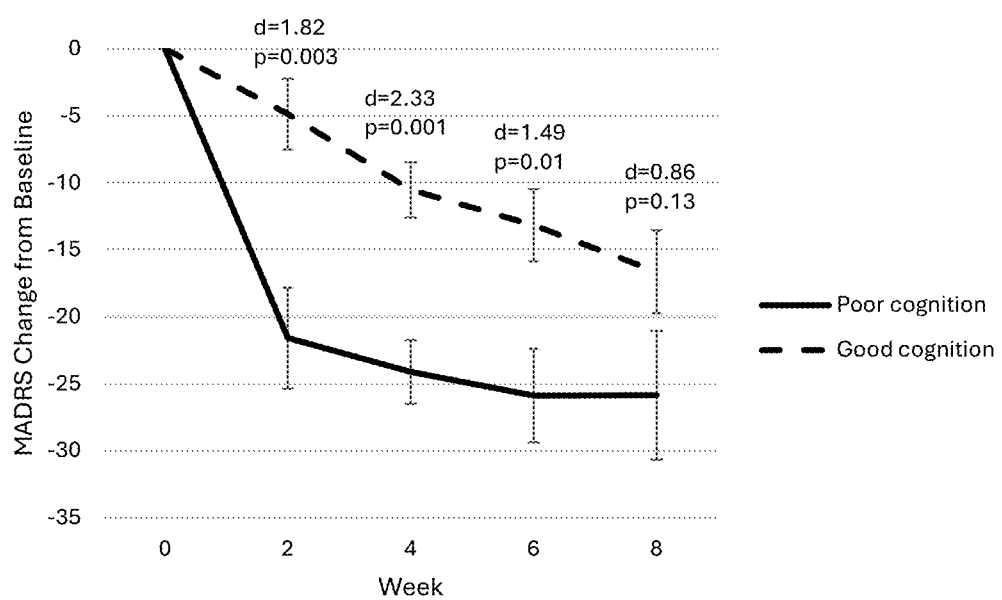
FIG. 13 is a graph of MADRS change from baseline over time in patients receiving NSI-189 with poor cognition as determined by poor verbal memory (z<-0.5) and patients with good cognition as determined by good verbal memory (z>-0.5), as described in Example 4.

To examine the reproducibility of the ability of poor cognition to identify NSI-189 responders, the inventors ran an additional trial, which included 20 subjects with moderate to severe depression (n=6 classified as poor cognition based on poor verbal memory (z<−0.5) and n=14 classified as good cognition (z>−0.5). All patients were treated with 80 mg (40 mg BID) NSI-189 and assessed using MADRS scales for eight weeks. An analysis of Covariance (ANCOVA, controlling for baseline depression severity) was used to analyze the data at each week. Poor cognition patients demonstrated a large and statistically significantly greater improvement across weeks 2, 4, and 6, with a trend at week 8. The results are shown in FIG. 13. These data demonstrate in an independent patient cohort that poor cognition, as determined by poor verbal memory capacity, is a predictor of better antidepressant response to NSI-189.

Example 5—Randomized, Double-Blind, Placebo-Controlled Study of NSI-189 With an Open-Label Extension in Adults With MDD This is a 6-week, multi-center, double-blind (DB), placebo-controlled study of NSI-189 40 mg BID (80 mg total daily dose) in approximately 266 adults with MDD coupled to an optional 7-week, open-label (OL) period. After a screening period of approximately 6 weeks (up to 40 days), eligible study participants will be randomized to either NSI-189 40 mg BID or a matched placebo (given adjunctively with an antidepressant or as a monotherapy) and followed for 6 weeks for the DB treatment period. The DB period consists of 5 study visits including Day 1 when study intervention is started. Any participant who completes the DB period and is tolerating the study intervention well may enter a 7-week OL period to receive NSI-189 40 mg BID with 4 additional visits. Of note, unblinding will not occur between the DB and OL periods, and the OL period will start the same day as the DB end-of-treatment (EOT) visit. After completion of study medication at the end of the OL period, or after the DB period for those who do not enter the OL period, or in the case of early discontinuation of study intervention, participants will have an end-of-treatment (EOT) visit followed by a safety follow-up visit approximately one week later.

The inclusion criteria for the patients:
Aged 18 to <71 years old and have a body mass index of 17-41
Diagnosed with MDD based on the SCID-5 and
Have moderate to severe MDD based on DSM-5 criteria items, as assessed by a score≥10 on the Patient Health Questionnaire (PHQ-9)
Have moderate to severe MDD as confirmed by a MADRS total score≥22 administered by the MGH-CTNI remote rater
Prior to treatment with NSI-189,
Not taking an antidepressant (other than low dose trazodone [≤100 mg/day] for sleep) or low dose tricyclic antidepressant (TCA) [≤25 mg/day]) or taking a stable dose of a single SSRI, SNRI, mirtazapine, or bupropion (only one antidepressant is allowed prior to treatment with NSI-189 except for the exceptions above) and:
have been on that medication for ≥6 weeks at an adequate dosage defined by the Antidepressant Treatment Response Questionnaire (ATRQ), and with no modification to the dose of the antidepressant for ≥2 weeks prior to treatment with NSI-189.
have <50% improvement in their depressive symptoms on the current antidepressant as assessed by the ATRQ
AND either:
have had a continuous period of remission (defined as not meeting DSM-5 MDD criteria) of at least 2 continuous months in the past 26 months, regardless of the number of failed antidepressants; OR
have not had a period of remission of at least 2 months in the past 26 months but within the past 24 months have not failed >3 antidepressants at an adequate dosage and duration (≥4 weeks) as defined by the ATRQ.

Exclusion criteria include:
1. Any of the following medical conditions:
   pregnant or breastfeeding or planning to become pregnant.
   severe impediment to vision, hearing, comprehension, and/or hand movement that interferes with study tasks such as completing tasks on a computer.
   clinically significant history or evidence of acute or unstable cardiovascular, respiratory, hepatic, renal, gastrointestinal, endocrine, neurological (such as in the past year: seizure, cerebral vascular disease, traumatic brain injury), immunological, or other major disease as determined by the site investigator. Stable, chronic medical illnesses are allowed.
   Gastric bypass, gastric lap band, or gastric sleeve procedure within the past year, or have current gastric dumping syndrome or other disorder of GI absorption, due to the potential inability to absorb the investigation intervention completely.
2. Concurrent use of any of the following at baseline (initial treatment with NSI-189):
   monoamine oxidase inhibitors (MAOIs)
   tricyclic antidepressants (TCAs)>25 mg/d
   mood stabilizers (anticonvulsants for non-psychiatric reasons may be allowed with Sponsor's permission)
   antipsychotic medications
   benzodiazepines, stimulants, or opiate pain medications greater than three days per week and unable to reduce use to 3 or fewer days per week on an as needed basis. Sedatives/hypnotics may be used daily except 24 hours before a biomarker assessment.
Note: Medications may be modified to meet inclusion criteria if clinically indicated. Medications should be discontinued long enough before screening and treatment with NSI-189 is initiated (at least 5 days) to ensure that there are no symptoms of withdrawal.
3. Are on more than one current antidepressant other than low-dose trazodone and/or TCA at screening.
4. Have received electroconvulsive therapy (ECT), deep brain stimulation (DBS), vagus nerve stimulation (VNS), or >2 treatments with ketamine and/or esketamine in the current depressive episode.
5. Receipt of any other central nervous system (CNS) investigational medication or investigational device within 6 months of the first study visit and more than one CNS interventional trial in the past 12 months. Non-CNS interventional trials or CNS observational trials may be allowed in the past 6 to 12 months after review with the Sponsor.
6. Prior participation in a study with NSI-189
7. Diagnosis of bipolar disorder or a psychotic disorder based on the SCID for DSM-5 or diagnosis of dementia based on history and patient interview.
8. Significant current PTSD symptoms based on SCID diagnosis of PTSD or history of PTSD and PCL-5>42 at Visit 1.
9. Positive urine toxicology (not including marijuana or documented prescription). One retest during screening is allowed. Current moderate or severe substance use disorder (SUD) (other than nicotine) determined by clinical assessment is exclusionary. Participants with a history of SUDs need to be in remission for at least 3 months prior to the start of the study.

10. Excessive use of alcohol defined by (on average) >21 standard drinks/week for males and >14 standard drinks/week for females.

11. Electrocardiograms (ECG) with QTcF interval duration>450 msec (males) or >470 msec (females) after at least 5 minutes in a supine, quiet resting position at screening or clinically significant irregular heartbeat (such as atrial fibrillation) or cardiac arrhythmia based on the screening ECG.

12. Active suicidal ideation as determined by the CHRT-SR12 score of 3 or 4 on items 11 or 12 at screening or investigator assessment based on results from the CHRT-C and clinical assessment at screening.

13. Known hypersensitivity to NSI-189, its components, or any of the excipients used in the formulation.

14. Any other condition and/or situation that the investigator believes may interfere with the safety of the participant, study conduct, or interpretation of study data.

15. No use of drugs of abuse except for limited amounts of cannabis (any form, up to 3 days per week and not meeting criteria for SUD) is permitted during study participation. Participants are asked to follow Centers for Disease Control and Prevention (CDC) recommendations for alcohol consumption: 1 standard drink per day (averaged over a week) for females and 2 standard drinks per day (averaged over a week) for males.

The primary objective is to assess efficacy of NSI-189 versus placebo on symptoms of MDD (as measured by change in MADRS total score during 6 weeks of treatment) in the subgroup of participants having a biomarker such as impaired verbal memory. One secondary objective is to assess efficacy in participants having a biomarker such as impaired verbal memory who are taking NSI-189 as a monotherapy. Other secondary objectives include assessment of efficacy of NSI-189 for symptoms of MDD in participants having a biomarker such as impaired verbal memory, as measured by patient-reported PHQ-9, CGI-S, and response and remission rates based on the MADRS.

Participants will be assessed using the following tests.

| Task | Cognitive Domain | Cognitive Function |
| --- | --- | --- |
| Typing Task | Attention | Motor Speed, Coordination |
| Verbal Fluency Task | Language | Verbal Fluency[1] |
| Simple Reaction Time Task | Attention | Motor Speed, Simple[2] |
| Choice Reaction Time Task | Attention | Processing Speed, Simple[3] |
| Digit Symbol Substitution Task | Attention | Processing Speed, Complex[4] |
| Corsi Block Task | Memory | Spatial Working Memory[5] |
| Verbal Memory Recall Task | Memory | Verbal Memory[6] |
| Facial Emotion Recognition Task | Attention | Social/Emotional Processing[7] |
| Trail Making Task | Executive Function | Cognitive Flexibility, Divided Attention[8] |
| Wisconsin Card Sort Task | Executive Function | Abstract Reasoning, Cognitive Flexibility[9] |
| Flanker Task (Erikson Flanking Arrows Task) | Executive Function | Response Inhibition, Complex[10] |
| Delay Discounting Task | Reward | Temporal Discounting[11] |
| Tapping Task | Coordination | Motor Speed, Coordination |

[1] Borkowski et al., Word fluency and brain damage, *Neuropsychologia*, 5(2):135-140, May 1967, doi: 10.1016/0028-3932(67)90015-2.
[2] Jain et al., A comparative study of visual and auditory reaction times on the basis of gender and physical activity levels of medical first year students, *Int J Appl Basic Med Res*. 2015, 5(2): 124-127. doi: 10.4103/2229-516X.157168
3 Armstrong LE et al., Mild dehydration affects mood in healthy young women, *J. Nutr.*, 142(2):382-8, February 2012, doi: 10.3945/jn.111.142000.
[4] Thorndike EL, A standardized group examination of intelligence independent of language, *J. Appl. Psychol.*, 3(1): 13-32, March 1919, doi: 10.1037/h0070037.
[5] Corsi PM, Human memory and the medial temporal region of the brain, *Diss Abstr Int*, vol. 34, 1973.
[6] Naparstek et al., Development of VM-REACT: Verbal memory RecAll computerized test, *J Psychiatr Res*, 114:170-177, July 2019, doi: 10.1016/j.jpsychires.2019.04.023
[7] Arnone et al., Early effects of mirtazapine on emotional processing, *Psychopharmacology (Berl).*, vol. 203, no. 4, pp. 685-691, May 2009, doi: 10.1007/s00213-008-1410-6.
[8] Reitan, The relation of the Trail Making Test to organic brain damage, *J Consult Psychol*, 1955; vol. 19(5), pp. 393-394.
[9] Grant and Berg, A behavioral analysis of degree of reinforcement and ease of shifting to new responses in a Weigl-type card-sorting problem, *J Exp Psychol*, vol. 38, no. 4, pp. 404-411, 1948, doi: 10.1037/h0059831.
[10] Eriksen, The Flankers task and response competition: A useful tool for investigating a variety of cognitive problems, *Vis. cogn.*,1995, vol. 2, no. 2-3, pp. 101-118.
[11] Koffarnus and Bickel, A 5-trial adjusting delay discounting task: accurate discount rates in less than one minute. *Exp Clin Psychopharmacol*, vol. 22, no. 3, pp. 222-8, June 2014, doi: 10.1037/a0035973.

Example 6—Randomized, Double-Blind, Placebo-Controlled Study Followed by an Open-Label Treatment of NSI-189 in Adults with Bipolar Disorder Currently Experiencing a Major Depressive Episode This is a 6-week, randomized, double-blind (DB), placebo-controlled study with an enrichment-marker stratification to compare antidepressant efficacy of NSI-189 40 mg BID (80 mg total daily dose) versus placebo in the marker-enriched group of adults with bipolar disorder with depression (BD-D) (defined as <50% improvement in depression symptoms) who are concurrently taking a mood stabilizer(s) followed by an optional 7-week open label (OL) period.

After a screening period of up to 5 weeks (35 days), eligible study participants will be randomized to either NSI-189 40 mg BID or a matched placebo for 6 weeks. To reduce risk of manic cycling, study interventions will be taken adjunctive to a concurrently prescribed mood stabilizer, including lithium, lamotrigine, or valproic acid alone or in combination as described above, and participants will be followed for 6 weeks for the DB treatment period. The DB period consists of 5 study visits including Day 1 when study intervention is started. Any participant who completes the DB period and is tolerating the study intervention may enter a 7-week OL period to receive NSI-189 40 mg BID with 4 additional visits. Of note, unblinding will not occur between the DB and OL periods, and the OL period will start the same day as the DB end-of-treatment (EOT) visit. After completion of study medication at the end of the OL period, after the DB period for those who do not enter the OL period, or in the case of early discontinuation of study intervention, participants will have an EOT visit followed by a safety follow-up visit approximately one week later.

The overall goal of the study is to demonstrate antidepressant efficacy of NSI-189 compared to placebo in patients with BD-D experiencing an MDE, with the primary outcome assessed in the marker-enriched subpopulation. To reduce bias during the study, all patients and site staff will be blinded to the information about the marker or marker status for individual patients. Moreover, both patients with and without the marker will be enrolled.

The inclusion criteria for the patients are as follows:
1. Participants must be aged 18 to <71 years old.
2. Have a diagnosis of bipolar disorder I (BD-I) or bipolar disorder (BD-II) as well as BD-D based on the SCID-5
   have a current major depressive disorder based on the SCID-5
   have a history of a manic and/or hypomanic episode(s) based on the SCID-5 but no manic, hypomanic, or mixed episode in the past 3 months
3. Have moderate to severe depressive symptoms based on:
   a score≥10 on the Patient Health Questionnaire (PHQ-9) at each of Visits 1 and 2
   have moderate to severe depressive symptoms as confirmed by a MADRS total score≥22 administered by the MGH-CTNI remote rater before Visit 2 and pass the SAFER interview
4. At screening (Visit 2):
   taking a stable dose of a mood stabilizer lithium (Li) or lamotrigine (LMG) or valproic acid (VPA, any form) at Visit 2, or combinations of Li+LMG or Li+VPA are allowed and:
     have been on that medication for ≥6 weeks at an adequate dosage, and with no modification to the dose of mood stabilizer(s) for ≥2 weeks prior to Visit 2.
       are on an adequate dose as determined by blood levels at Visit 1 or 2 of Li≥0.5 mmol/L or VPA≥50 mmol/L) or
       a dose of LMG≥200 mg/day
     have <50% improvement in their depressive symptoms on the current mood stabilizer,
5. Patient-specific Markers
   Complete all Visit 2 marker assessments:
     genetic testing may be refused by the participant, and the participant would be allowed to enroll.
     wearables may not be done if a participant does not have a smartphone or internet-connected tablet.
     Determined to be eligible based on a review of the markers and demographics collected during screening.

Note: During the study, the sponsor may screen fail participants based on enrichment marker status to have appropriate balance of populations.
6. Additionally, body mass index (BMI, kg/m$_2$)≥17 and ≤40

The exclusion criteria for the patients are as follows:
1. Any of the following medical conditions:
   pregnant or breastfeeding or planning to become pregnant.
   severe impediment to vision, hearing, comprehension, and/or handmovement that interferes with study tasks such as completing tasks on a computer.
   clinically significant history or evidence of acute or unstable cardiovascular, respiratory, hepatic, renal, gastrointestinal, endocrine, neurological (such as in the past year: seizure, cerebral vascular disease, traumatic brain injury), immunological, or other major disease as determined by the site investigator. Stable, chronic medical illnesses are allowed.
   gastric bypass or other disorder of GI absorption, due to the potential failure to metabolize and absorb the investigation intervention completely and safely.
2. Concurrent use of any of the following at the second screening visit (Visit 2):
   any antidepressant at any dose for any indication. Antidepressants need to be stopped at least 5 days prior to Visit 2 (other than low dose trazodone used for sleep (≤100 mg/day) or low dose tricyclic antidepressant (TCA≤25 mg/day)) which are allowed.
   antipsychotic medications (all antipsychotic medications need to be stopped at least 5 days before Visit 2)
   anticonvulsants other than lamotrigine (LMG) or valproic acid (VPA) as mood stabilizers or gabapentin for anxiety disorder
     Under limited circumstances and with sponsor permission, other anticonvulsants may be allowed for non-psychiatric reasons
   benzodiazepines, stimulants, or opiate pain medications greater than three days per week and unable to reduce use to 3 or fewer days per week on an as needed basis.
   Sedatives/hypnotics may be used daily except 24 hours before a marker assessment if started prior to Visit 1.
Note: Medications may be modified to meet inclusion criteria if clinically indicated. Medications should be discontinued long enough before Visit 2 (at least 5 days) to ensure that there are no symptoms of withdrawal.
3. Have received electroconvulsive therapy (ECT), deep brain stimulation (DBS), vagus nerve stimulation (VNS), or >2 treatments with ketamine and/or esketamine in the current depressive episode.
4. Receipt of any other central nervous system (CNS) investigational medication or investigational device within 6 months of the first study visit and more than one CNS interventional trial in the past 12 months. Non-CNS interventional trials or CNS observational trials may be allowed in the past 6 to 12 months after review with the Sponsor.
5. Prior participation in a study with NSI-189.
6. Diagnosis of a psychotic disorder (other than mania or depression) based on the SCID-5 or current psychotic symptoms.
7. Diagnosis of dementia based on history and patient interview.
8. Current symptoms of mania or hypomania defined by a YMRS>12 at Visits 1, 2, or 3 or meeting criteria for a current episode of mania or hypomania on the SCID.
9. Significant current PTSD symptoms based on SCID diagnosis of PTSD or history of PTSD and PCL-5>45 at Visit 1.
10. Positive urine toxicology (not including marijuana or documented prescription). One retest during screening is allowed. Current moderate or severe substance use disorder (SUD) (other than nicotine) determined by clinical assessment is exclusionary. Participants with a history of SUDs need to be in remission for at least 3 months prior to Visit 1.

11. Excessive use of alcohol defined by their weekly average standard drinks: >21 for males and >14 for females.
12. Electrocardiograms (ECG) with QTcF interval duration>450 msec (males) or >470 msec (females) after at least 5 minutes in a supine, quiet resting position at Visit 2 or clinically significant irregular heartbeat (such as atrial fibrillation) or cardiac arrhythmia based on the screening ECG.
13. Active suicidal ideation as determined by the CHRT-SR12 score of 3 or 4 on items 11 or 12 at Visit 2 or investigator assessment based on results from the CHRT-C and clinical assessment at Visits 1 and 2.
14. Known hypersensitivity to NSI-189, its components, or any of the excipients used in the formulation.
15. Any other condition and/or situation that the investigator believes may interfere with the safety of the participant, study conduct, or interpretation of study data.
16. No use of drugs of abuse except for limited amounts of cannabis (any form, up to 3 days per week and not meeting criteria for SUD) is permitted during study participation. Participants are asked to follow Centers for Disease Control and Prevention (CDC) recommendations for alcohol consumption: 1 standard drink per day (averaged over a week) for females and 2 standard drinks per day (averaged over a week) for males.

The primary objective is to assess efficacy of NSI-189 versus placebo in marker-defined patients with BD-D (I or II), as measured by change in MADRS total score during 6 weeks of treatment) (e.g., in the subgroup of participants having a biomarker such as impaired verbal memory). One secondary objective is to assess antidepressant efficacy in participants having a biomarker such as impaired verbal memory who are taking NSI-189 and have BD-D, as measured by patient-reported PHQ-9, CGI-S, and response and remission rates based on the MADRS.

Participants will be assessed using the following tests.

3. Carli M, Aringhieri S, Kolachalam S, Longoni B, Grenno G, Rossi M, Gemignani A, Fornai F, Maggio R, Scarselli M. Is adult hippocampal neurogenesis really relevant for the treatment of psychiatric disorders? Curr Neuropharmacol. 2020.
4. Park S C. Neurogenesis and antidepressant action. Cell Tissue Res. 2019; 377:95-106.
5. Tunc-Ozcan E, Peng C Y, Zhu Y, Dunlop S R, Contractor A, Kessler J A. Activating newborn neurons suppresses depression and anxiety-like behaviors. Nat Commun. 2019; 10:3768.
6. Serafini G. Neuroplasticity and major depression, the role of modern antidepressant drugs. World J Psychiatry. 2012; 2:49-57.
7. Levy M J F, Boulle F, Steinbusch H W, van den Hove D L A, Kenis G, Lanfumey L. Neurotrophic factors and neuroplasticity pathways in the pathophysiology and treatment of depression. Psychopharmacology (Berl). 2018; 235:2195-2220.
8. Allen B D, Acharya M M, Lu C, Giedzinski E, Chmielewski N N, Quach D, Hefferan M, Johe K K, Limoli C L. Remediation of Radiation-Induced Cognitive Dysfunction through Oral Administration of the Neuroprotective Compound NSI-189. Radiat Res. 2018; 189:345-353.
9. Bauman M D, Schumann C M, Carlson E L, Taylor S L, Vazquez-Rosa E, Cintron-Perez C J, Shin M K, Williams N S, Pieper A A. Neuroprotective efficacy of P7C3 compounds in primate hippocampus. Transl Psychiatry. 2018; 8:202.
10. Fava M, Johe K, Ereshefsky L, Gertsik L G, English B A, Bilello J A, Thurmond L M, Johnstone J, Dickerson B C, Makris N, Hoeppner B B, Flynn M, Mischoulon D, Kinrys G, Freeman M P. A Phase 1B, randomized, double blind, placebo controlled, multiple-dose escalation study of NSI-189 phosphate, a neurogenic compound, in depressed patients. Mol Psychiatry. 2016; 21:1372-1380.

| Task | Cognitive Domain | Cognitive Function |
|---|---|---|
| Typing Task | Attention | Motor Speed, Coordination |
| Verbal Fluency Task | Language | Verbal Fluency[1] |
| Simple Reaction Time Task | Attention | Motor Speed, Simple[2] |
| Choice Reaction Time Task | Attention | Processing Speed, Simple[3] |
| Digit Symbol Substitution Task | Attention | Processing Speed, Complex[4] |
| Corsi Block Task | Memory | Spatial Working Memory[5] |
| Verbal Memory Recall Task | Memory | Verbal Memory[6] |
| Facial Emotion Recognition Task | Attention | Social/Emotional Processing[7] |
| Trail Making Task | Executive Function | Cognitive Flexibility, Divided Attention[8] |
| Wisconsin Card Sort Task | Executive Function | Abstract Reasoning, Cognitive Flexibility[9] |
| Flanker Task (Erikson Flanking Arrows Task) | Executive Function | Response Inhibition, Complex[10] |
| Delay Discounting Task | Reward | Temporal Discounting[11] |

(The citations are to those referenced in the table in Example 5.)

REFERENCES

1. Rodrigues R S, Paulo S L, Moreira J B, Tanqueiro S R, Sebastiao A M, Diogenes M J, Xapelli S. Adult Neural Stem Cells as Promising Targets in Psychiatric Disorders. Stem Cells Dev. 2020; 29:1099-1117.
2. Zarate C A, Jr., Singh J, Manji H K. Cellular plasticity cascades: targets for the development of novel therapeutics for bipolar disorder. Biol Psychiatry. 2006; 59:1006-1020.
11. Papakostas G I, Johe K, Hand H, Drouillard A, Russo P, Kay G, Kashambwa R, Hoeppner B, Flynn M, Yeung A, Martinson M A, Fava M. A phase 2, double-blind, placebo-controlled study of NSI-189 phosphate, a neurogenic compound, among outpatients with major depressive disorder. Mol Psychiatry. 2020; 25:1569-1579.
12. Snyder H R. Major depressive disorder is associated with broad impairments on neuropsychological measures of executive function: a meta-analysis and review. Psychol Bull. 2013; 139:81-132.

13. Parkinson W L, Rehman Y, Rathbone M, Upadhye S. Performances on individual neurocognitive tests by people experiencing a current major depression episode: A systematic review and meta-analysis. J Affect Disord. 2020; 276:249-259.
14. Etkin A, Patenaude B, Song Y J, Usherwood T, Rekshan W, Schatzberg A F, Rush A J, Williams L M. A cognitive-emotional biomarker for predicting remission with antidepressant medications: a report from the iSPOT-D trial. Neuropsychopharmacology. 2015; 40:1332-1342.
15. Fava M, Iosifescu D V, Pedrelli P, Baer L. Reliability and validity of the Massachusetts general hospital cognitive and physical functioning questionnaire. Psychother Psychosom. 2009; 78:91-97.
16. Koenig A M, Bhalla R K, Butters M A. Cognitive functioning and late-life depression. J Int Neuropsychol Soc. 2014; 20:461-467.
17. Scott J C, Matt G E, Wrocklage K M, Crnich C, Jordan J, Southwick S M, Krystal J H, Schweinsburg B C. A quantitative meta-analysis of neurocognitive functioning in posttraumatic stress disorder. Psychol Bull. 2015; 141:105-140.
18. Hall M G, Hauson A O, Wollman S C, Allen K E, Connors E J, Stern M J, Kimmel C L, Stephan R A, Sarkissians S, Barlet B D, Grant I. Neuropsychological comparisons of cocaine versus methamphetamine users: A research synthesis and meta-analysis. Am J Drug Alcohol Abuse. 2018; 44:277-293.
19. Padilla-Coreano N, Canetta S, Mikofsky R M, Alway E, Passecker J, Myroshnychenko M V, Garcia-Garcia A L, Warren R, Teboul E, Blackman D R, Morton M P, Hupalo S, Tye K M, Kellendonk C, Kupferschmidt D A, Gordon J A. Hippocampal-Prefrontal Theta Transmission Regulates Avoidance Behavior. Neuron. 2019; 104:601-610 e604.
20. Egner T, Etkin A, Gale S, Hirsch J. Dissociable neural systems resolve conflict from emotional versus nonemotional distracters. Cereb Cortex 2008; 18:1475-84.
21. Xue S, Wang S, Kong X, Qiu J. Abnormal Neural Basis of Emotional Conflict Control in Treatment-Resistant Depression. Clin EEG Neurosci 2017; 48:103-10.
22. Xu M, Xu G, Yang Y. Neural Systems Underlying Emotional and Non-emotional Interference Processing: An ALE Meta-Analysis of Functional Neuroimaging Studies. Front Behav Neurosci 2016; 10:220.
23. Etkin A, Egner T, Peraza D M, Kandel E R, Hirsch J. Resolving emotional conflict: a role for the rostral anterior cingulate cortex in modulating activity in the amygdala. Neuron 2006; 51:871-82.
24. Maier M E, di Pellegrino G. Impaired conflict adaptation in an emotional task context following rostral anterior cingulate cortex lesions in humans. J Cogn Neurosci 2012; 24:2070-9.
25. Gyurak A, Patenaude B, Korgaonkar M S, Grieve S M, Williams L M, Etkin A. Frontoparietal Activation During Response Inhibition Predicts Remission to Antidepressants in Patients With Major Depression. Biol Psychiatry 2016; 79:274-81.
26. Williams L M, Korgaonkar M S, Song Y C, et al. Amygdala Reactivity to Emotional Faces in the Prediction of General and Medication-Specific Responses to Antidepressant Treatment in the Randomized iSPOT-D Trial. Neuropsychopharmacology 2015; 40:2398-408.
27. Johe et al., Ann Clin Psychiatry, 32(3): 182-196 (2020).
28. Amos et al., J Clin Psychiatry, 79(2): 17m11725, 2018.
29. Rush et al., N Engl J Med. 2006, 354: 1231-1242.
30. Chandler et al., Validation of the Massachusetts General Hospital Antidepressant Treatment History Questionnaire (ATRQ). CNS Neurosci. Ther., 2010; 16:322-5.
31. Cipriani et al., Lancet, 2018 Apr. 7, 391(10128): 1357-1366 (PMID 29477251).
32. Wen e., Braz J Med Biol Res, 2014 July, 47(7):605-16 (PMID 24919175).
33. Nelson, Am J Psychiatry, 2006 November, 163(11): 1864-6 (PMID 17074931).
34. Warden et al., Curr Psychiatry Rep, 2007 December; 9(6):449-59 (PMID 18221624).
35. Zhou et al., Int J Neuropsychopharmacol. 2015 May 25; 18 (11):pyv060 (PMID 26012350).
36. Papakostas et al., J Clin Psychiatry. 2020 May 26; 81(4):19r12889 (PMID 32459407).
37. Kishi et al., Int J Neuropsychopharmacol., 2019 Nov. 1; 22(11):698-709 (PMID 31350882).
38. Iosifescu et al., J Clin Psychiatry, 2022 May 30; 83(4): 21m14345 (PMID 35649167).
39. Ang et al., Psychol Med. 2020 Nov. 20; 1-9 (PMID 33213541).
40. Groves et al., Front Psychiatry, 2018 Aug. 28; 9:382 (PMID 30210368).
41. Levenberg et al., Gen Psychiatr. 2022, 35(4):e100760 (PMID 36035376).

All publications, patents and patent applications cited herein are hereby incorporated by reference as if set forth in their entirety herein. While this invention has been described with reference to illustrative embodiments, this description is not intended to be construed in a limiting sense. Various modifications and combinations of illustrative embodiments, as well as other embodiments of the invention, will be apparent to persons skilled in the art upon reference to the description. It is therefore intended that the appended claims encompass such modifications and enhancements.

The invention claimed is:

1. A method of treating bipolar depression in a human patient having objectively determined impaired learning and/or memory comprising orally administering to the patient from about 40 to about 240 mg of (4-benzylpiperazin-1-yl)-[2-(3-methylbutylamino)pyridin-3-yl]methanone or a pharmaceutically acceptable salt thereof daily.

2. The method of claim 1, wherein the patient has impaired learning and/or memory as objectively determined by poor immediate recall in a verbal memory test.

3. The method of claim 1, wherein the patient has impaired learning and/or memory as objectively determined by poor delayed recall in a verbal memory test.

4. The method of claim 1, wherein the (4-benzylpiperazin-1-yl)-[2-(3-methylbutylamino)pyridin-3-yl]methanone or a pharmaceutically acceptable salt thereof is administered such that, at steady state the $C_{max}$ for (4-benzylpiperazin-1-yl)-[2-(3-methylbutylamino)pyridin-3-yl]methanone is about 230 to about 630 ng/mL.

5. The method of claim 1, wherein the (4-benzylpiperazin-1-yl)-[2-(3-methylbutylamino)pyridin-3-yl]methanone or a pharmaceutically acceptable salt thereof is administered such that, at steady state the $AUC_{0-24}$ for (4-benzylpiperazin-1-yl)-[2-(3-methylbutylamino)pyridin-3-yl]methanone is about 1400 to about 3200 hr·ng/mL.

6. The method of claim 1, wherein the (4-benzylpiperazin-1-yl)-[2-(3-methylbutylamino)pyridin-3-yl]methanone or a pharmaceutically acceptable salt thereof is administered such that, at steady state the $AUC_{0-tau}$ for (4-benzylpiperazin-1-yl)-[2-(3-methylbutylamino)pyridin-3-yl]methanone is about 1200 to about 2050 hr·ng/ml.

7. The method of claim 1, wherein about 60 to about 100 mg of (4-benzylpiperazin-1-yl)-[2-(3-methylbutylamino)pyridin-3-yl]methanone or a pharmaceutically acceptable salt thereof is administered daily.

8. The method of claim 7, wherein about 40 mg of (4-benzylpiperazin-1-yl)-[2-(3-methylbutylamino)pyridin-3-yl]methanone or a pharmaceutically acceptable salt thereof is administered twice daily.

9. The method of claim 1, wherein the patient is treated with (4-benzylpiperazin-1-yl)-[2-(3-methylbutylamino)pyridin-3-yl]methanone or a pharmaceutically acceptable salt thereof as a monotherapy.

10. The method of claim 1, wherein the patient is concurrently treated with a mood stabilizer in addition to (4-benzylpiperazin-1-yl)-[2-(3-methylbutylamino)pyridin-3-yl]methanone or a pharmaceutically acceptable salt thereof.

11. The method of claim 10, wherein the mood stabilizer is selected from lithium carbonate, divalproex sodium, valproic acid, valproate semisodium, sodium valproate, tiagabine, levetiracetam, lamotrigine, gabapentin, carbamazepine, oxcarbazepine, topiramate, zonisamide, aripiprazole, risperidone, olanzapine, quetiapine, asenapine, paliperidone, ziprasidone, lurasidone, lumateperone, cariprazine, verapamil, clonidine, propranolol, mexiletine, guanfacine and omega-3 fatty acids.

12. The method of claim 10, wherein the mood stabilizer is selected from lithium, lamotrigine, valproic acid, and any combination of any of the foregoing.

13. A method of treating a major depressive episode in a human patient with bipolar disorder with depression comprising:
(a) objectively assessing whether the patient has impaired learning and/or memory; and
(b) upon an assessment from step (a) that the patient has impaired learning and/or memory, initiating oral administration to the patient of from about 40 to about 240 mg of (4-benzylpiperazin-1-yl)-[2-(3-methylbutylamino)pyridin-3-yl]methanone or a pharmaceutically acceptable salt thereof daily.

14. The method of claim 13, wherein about 40 mg of (4-benzylpiperazin-1-yl)-[2-(3-methylbutylamino)pyridin-3-yl]methanone or a pharmaceutically acceptable salt thereof is administered twice daily.

15. A method of treating a major depressive episode in a human patient with bipolar disorder with depression comprising:
(a) objectively assessing whether the patient has impaired learning and/or memory; and
(b) upon an assessment from step (a) that the patient has impaired learning and/or memory, (i) initiating oral administration to the patient of from about 40 to about 240 mg of (4-benzylpiperazin-1-yl)-[2-(3-methylbutylamino)pyridin-3-yl]methanone or a pharmaceutically acceptable salt thereof daily, and (ii) administering a mood stabilizer.

16. A method of treating a major depressive episode in a human patient with bipolar disorder with depression who has been and is currently undergoing treatment with a mood stabilizer, the method comprising:
(a) objectively assessing whether the patient has impaired learning and/or memory; and
(b) upon an assessment from step (a) that the patient has impaired learning and/or memory, (i) initiating oral administration to the patient of from about 40 to about 240 mg of (4-benzylpiperazin-1-yl)-[2-(3-methylbutylamino)pyridin-3-yl]methanone or a pharmaceutically acceptable salt thereof daily, and (ii) continuing administration of the mood stabilizer.

17. The method of claim 16, wherein the mood stabilizer is selected from lithium carbonate, divalproex sodium, valproic acid, valproate semisodium, sodium valproate, tiagabine, levetiracetam, lamotrigine, gabapentin, carbamazepine, oxcarbazepine, topiramate, zonisamide, aripiprazole, risperidone, olanzapine, quetiapine, asenapine, paliperidone, ziprasidone, lurasidone, lumateperone, cariprazine, verapamil, clonidine, propranolol, mexiletine, guanfacine and omega-3 fatty acids.

18. The method of claim 16, wherein the mood stabilizer is selected from lithium, lamotrigine, valproic acid, and any combination of any of the foregoing.

19. The method of claim 16, wherein the patient suffers from bipolar I disorder.

20. The method of claim 16, wherein the patient suffers from bipolar II disorder.

* * * * *